(12) United States Patent
Lv et al.

(10) Patent No.: US 8,729,280 B2
(45) Date of Patent: May 20, 2014

(54) FIVE CRYSTAL FORMS, METHODS OF PREPARATION, PHARMACEUTICAL COMPOSITIONS AND APPLICATIONS OF XLF-III-43

(75) Inventors: Yang Lv, Beijing (CN); Xiaoguang Chen, Beijing (CN); Ping Xie, Beijing (CN); Li Zhang, Beijing (CN); Cheng Wang, Beijing (CN)

(73) Assignee: Institute of Mataria Medica, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 13/131,492

(22) PCT Filed: Nov. 28, 2009

(86) PCT No.: PCT/CN2009/075196
§ 371 (c)(1),
(2), (4) Date: Sep. 12, 2011

(87) PCT Pub. No.: WO2010/060387
PCT Pub. Date: Jun. 3, 2010

(65) Prior Publication Data
US 2011/0319401 A1 Dec. 29, 2011

(30) Foreign Application Priority Data
Nov. 28, 2008 (CN) .......................... 2008 1 0227626

(51) Int. Cl.
C07D 311/00 (2006.01)

(52) U.S. Cl.
USPC .......................................... 549/289

(58) Field of Classification Search
USPC .......................................... 589/289
See application file for complete search history.

(56) References Cited

U.S. PATENT DOCUMENTS 8,338,401 B2  12/2012  Xu et al.

FOREIGN PATENT DOCUMENTS

| CN | 1506359 A | 6/2004 |
|---|---|---|
| CN | 1829506 A | 9/2006 |

OTHER PUBLICATIONS

Sheng, L. et al., "A HPLC Method for Determination of Nicousamide in Dog Plasma and its Application to Pharmacokinectic Studies" Journal of Chromatography B (2007) pp. 99-103, vol. 854.
Sheng, L. et al., "Pharmacokinetics of Nicousamide in Rats" Journal of Shanxi Medical University (Jul. 2007) pp. 599-603, vol. 38, No. 7, together with English-language abstract.
Sheng, L. et al., "Metabolism of Nicousamide in Rat and Human Liver in vitro" Acta Pharmaceutica Sinica (Sep. 12, 2008) pp. 912-916, vol. 403, No. 9, together with English language abstract.
International Search Report dated Feb. 11, 2010 issued in corresponding International Application No. PCT/CN2009/075196.
Li, H. et al., "Nicousamide Blocks the Effects of Advanced Glycation End Products on Renal Cells" European Journal of Pharmacology (Jan. 15, 2012) pp. 455-459, vol. 674.
Li, H. et al., "XLF-III-43, a Novel Coumarin-Aspirin Compound, Prevents Diabetic Nephropathy in Rats via Inhibiting Advanced Glycation End Products" European Journal of Pharmacology (Feb. 10, 2010) pp. 340-347, vol. 627.

*Primary Examiner* — Nizal Chandrakumar
(74) *Attorney, Agent, or Firm* — Scully, Scott, Murphy & Presser, P.C.

(57) ABSTRACT

This invention discloses that the five crystal forms of XLF-III-43 can be used as crude drugs. The invention also relates to the preparation methods of the five crystal forms of XLF-III-43 as crude drugs, to the applications of the sterling of the five crystal forms of XLF-III-43 and mixed crystals in different proportions as medicinally active components to develop various kinds of medicines and compound medicines. In addition, this invention also relates to applying the crystal samples of XLF-III-43 as crude drugs to treat kidney dysfunction, cardiocerebral vessel diseases, hypertension, type II diabetic mellitus, complications of hypertension and diabetic mellitus, tumor, precancerosis, edema, and achieves therapeutic effects by enhancing blood drug levels resulted from effects of crystal forms in the processes of treating all kinds of diseases.

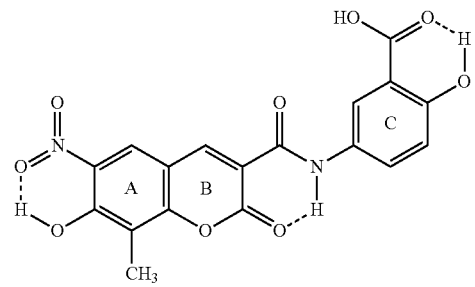

7 Claims, 21 Drawing Sheets

Figure 1:
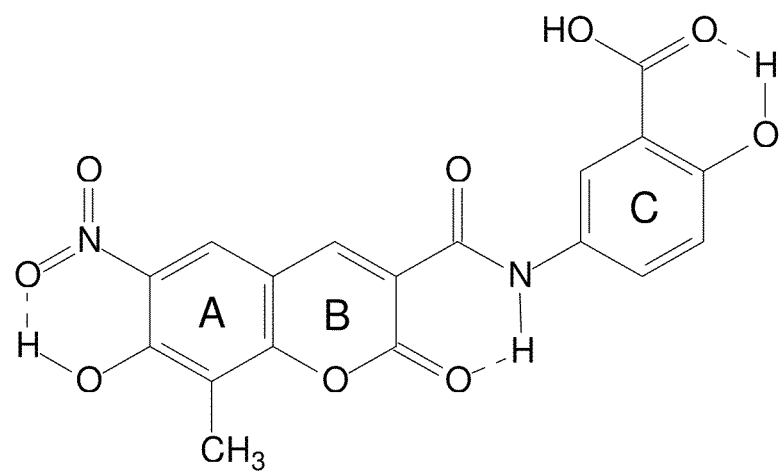

FIVE CRYSTAL FORMS, METHODS OF PREPARATION, PHARMACEUTICAL COMPOSITIONS AND APPLICATIONS OF XLF-III-43

FIELD OF THE INVENTION

The invention relates to taking the five crystalline forms of compound, XLF-III-43, as crude drug, the preparation methods of the five crystalline forms of XLF-III-43, taking the sterling of the five crystalline forms and mixed crystals with different proportions as active component and developing various kinds of medicines and pharmaceutical compositions. In addition, the invention also relates to applications that taking the crystal samples of XLF-III-43 as crude drugs to treat kidney dysfunction, cardiocerebral vessel diseases, hypertension, type II diabetic mellitus, complications of hypertension and diabetic mellitus, tumor, precancerosis, edema and so on, and in the processes of treating this diseases, improve blood drug level with the effects resulted from crystalline forms and gain therapeutic actions

BACKGROUND

XLF-III-43:3-(3'-carboxy-4'-hydroxy-anilino-carbo-)-6-nitro-7-hydroxy-8-methyl-coumarin)

Below is the structure of the compound:

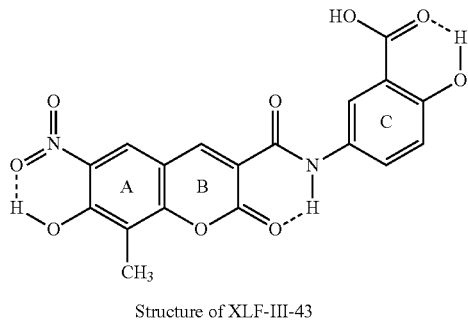

Structure of XLF-III-43

In Chinese patents CN1506359 (patent number) and CN1829506 (patent number), there is the record of invention of new Diarbarone derivatives, its preparation methods, pharmaceutical compositions and applications. In the record, it refers to the preparation methods of XLF-III-43 and its derivatives, applications of pharmaceutical compositions including these compounds in treating kidney dysfunction, hypertension, cardiocerebral vessel diseases, hypertension, type II diabetic mellitus, tumor, precancerosis, edema.

DETAILED DESCRIPTION

The first purpose of the invention: providing the solid samples of the crystalline forms of XLF-III-43, form I, form II, form III, form IV, form V.

The second purpose of the invention: providing the preparation methods of the solid samples of crystalline forms of XLF-III-43, form I, form II, form III, form IV, form V.

The third purpose of the invention: providing multiple pharmaceutical preparations of tablet, capsule, pill, injection, and several sustained release preparations and controlled release preparations, which are made from pharmaceutical compositions comprising one sterling of the five crystalline forms of XLF-III-43, form I, form II, form III, form IV, form V, or one of mixed crystals with different proportions, as crude drugs, and one or multiple medicine excipients.

The forth purpose of the invention: providing the variations of blood drug level and improved therapeutic actions resulted from the differences of crystalline forms of XLF-III-43 when take the sterling of five crystalline forms of XLF-III-43, form I, form II, form III, form IV, form V, and mixed crystals with different proportions as crude drugs in treating kidney dysfunction, cardiocerebral vessel diseases, hypertension, type II diabetic mellitus, complications of hypertension and diabetic mellitus, tumor, precancerosis, edema.

The fifth purpose of the invention: providing medicines and pharmaceutical compositions which take the samples of the five crystalline forms of XLF-III-43, type I, type II, type III, type IV, type V, and mixed crystals with different proportions as active components and are used in treating kidney dysfunction, kidney dysfunction, cardiocerebral vessel diseases, hypertension, type II diabetic mellitus, complications of hypertension and diabetic mellitus, tumor, precancerosis and edema.

In order to accomplish the purposes of the invention, these technical programs are applied:

The Morphological Characteristics of Crystalline Form I of XLF-III-43:

1. When taking X-ray single crystal diffraction to analyze the structure, the solid substance of crystalline form I of XLF-III-43 show the symmetry of triclinic system, the space group is P1, and the cell parameters are, a=13.666 Å, b=14.091 Å, c=14.370 Å, $\alpha$=98.95°, $\beta$=116.03°, $\gamma$=99.98°.

Figure 2:
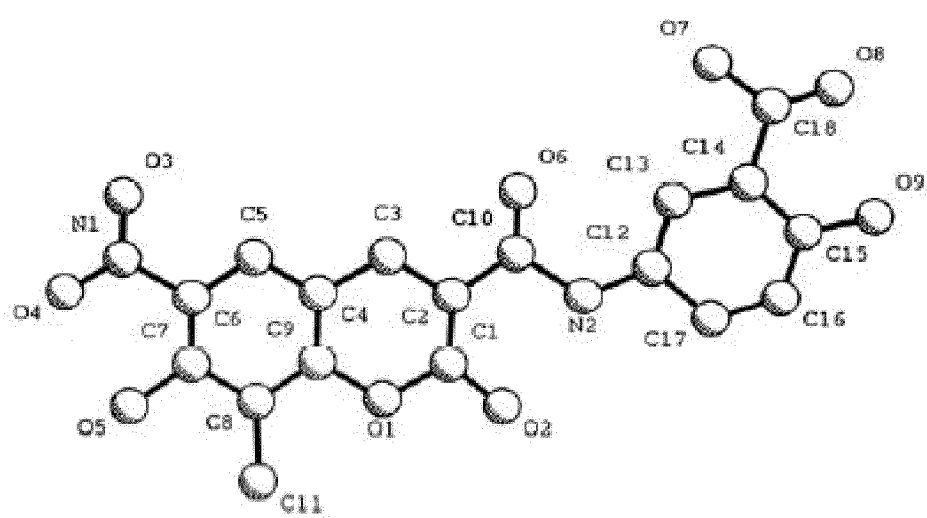
Figure 3:
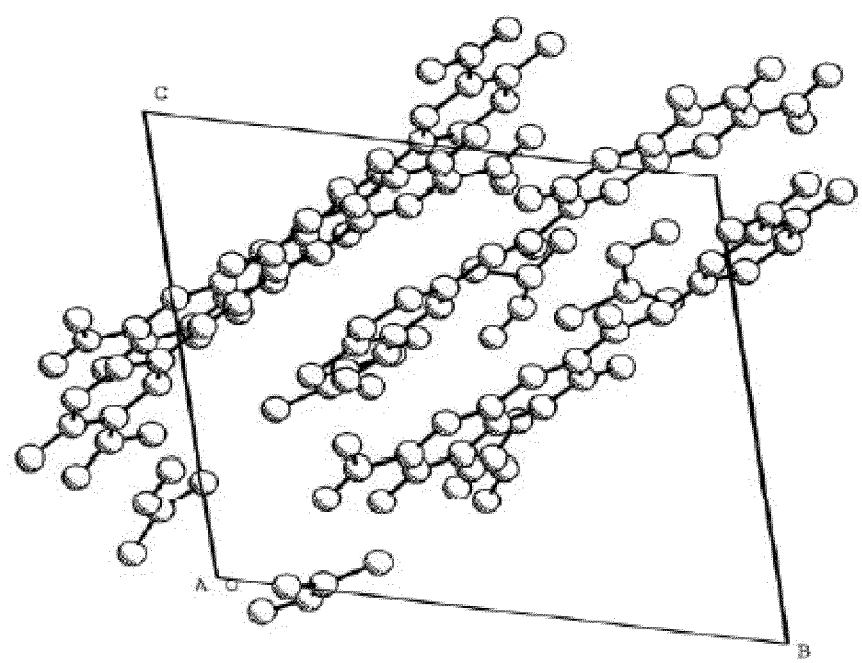

In solid substance sample of crystalline form I, except the molecular of XLF-III-43, $C_{18}H_{12}N_2O_9$, the crystallized solvent molecular of N,N'-dimethyl formamide also exists. In crystalline state, there are 4 molecular of XLF-III-43 and 5.5 molecular of DMF in one asymmetric unit. The proportion of the moleculars of XLF-III-43 and N,N'-dimethyl formamide is 4.0 to 5.5. FIG. 1 shows the molecular structure of XLF-III-43. FIG. 2 shows the tereochemical structure projection of the molecular of XLF-III-43. FIG. 3 shows the accumulation projection of the crystal unit of crystalline form I of XLF-III-43. Table 1 shows the non-hydrogen atomic coordinate parameters of crystalline form I of XLF-III-43. Table 2 shows the bond length values of bonding atoms of crystalline form I of XLF-III-43. Table 3 shows bond angle values of bonding atoms of crystalline form I of XLF-III-43.

TABLE 1

Non-hydrogen atomic coordinate parameters of the sample of crystalline form I of XLF-III-43 (relative coordinate)

| Atom | x | y | z | Biso |
|---|---|---|---|---|
| O1 | .7563(6) | .6301(5) | .4529(6) | 3.7(4) |
| O2 | .8149(7) | .7826(6) | .5610(7) | 5.7(5) |
| O3 | .9169(7) | .2699(6) | .3202(8) | 5.8(5) |
| O4 | .7375(8) | .2177(7) | .2015(7) | 6.1(5) |
| O5 | .5978(6) | .3151(6) | .2088(6) | 4.4(4) |
| O6 | 1.1541(6) | .7763(6) | .6727(7) | 5.1(5) |
| O7 | 1.4623(6) | 1.0161(6) | .8889(6) | 5.1(5) |
| O8 | 1.4948(7) | 1.1622(6) | 1.0082(7) | 4.9(5) |
| O9 | 1.3232(7) | 1.2225(6) | .9994(7) | 4.8(5) |
| N1 | .8212(8) | .2833(7) | .2763(8) | 4.7(6) |
| N2 | 1.0343(8) | .8692(6) | .6928(8) | 3.9(5) |
| C1 | .8478(10) | .7107(9) | .5269(9) | 4.3(7) |
| C2 | .9578(8) | .7054(8) | .5634(8) | 3.3(6) |
| C3 | .9797(9) | .6210(7) | .5174(8) | 2.9(6) |
| C4 | .8836(8) | .5373(8) | .4394(8) | 3.1(5) |
| C5 | .9004(9) | .4532(8) | .3942(9) | 3.7(6) |

TABLE 1-continued

Non-hydrogen atomic coordinate parameters of the sample of crystalline form I of XLF-III-43(relative coordinate)

| Atom | x | y | z | Biso |
|---|---|---|---|---|
| C6 | .8029(9) | .3791(7) | .3184(8) | 3.0(6) |
| C7 | .6972(9) | .3868(8) | .2872(9) | 3.5(6) |
| C8 | .6792(9) | .4726(9) | .3329(9) | 3.5(6) |
| C9 | .7746(9) | .5446(7) | .4065(9) | 3.1(6) |
| C10 | 1.0598(10) | .7829(7) | .6403(8) | 3.3(6) |
| C11 | .5604(9) | .4832(9) | .3037(11) | 4.8(7) |
| C12 | 1.1168(9) | .9511(7) | .7692(8) | 3.1(5) |
| C13 | 1.2317(9) | .9727(7) | .8129(8) | 3.3(6) |
| C14 | 1.3017(8) | 1.0640(8) | .8909(8) | 2.9(6) |
| C15 | 1.2586(8) | 1.1345(7) | .9276(8) | 2.7(5) |
| C16 | 1.1452(10) | 1.1131(8) | .8786(9) | 4.1(7) |
| C17 | 1.0729(8) | 1.0292(8) | .8039(9) | 4.1(6) |
| C18 | 1.4309(8) | 1.0897(8) | .9340(9) | 3.8(6) |
| O1' | .9263(6) | .2625(5) | .8033(6) | 3.4(4) |
| O2' | .8668(6) | .1159(6) | .6893(7) | 5.0(5) |
| O3' | .7659(6) | .6233(7) | .9373(6) | 6.9(6) |
| O4' | .9406(9) | .6832(7) | 1.0424(9) | 7.4(7) |
| O5' | 1.0859(7) | .5851(6) | 1.0308(6) | 4.5(4) |
| O6' | .5259(7) | .1128(6) | .5886(7) | 4.9(5) |
| O7' | .2272(7) | −.0761(6) | .2952(6) | 4.9(5) |
| O8' | .1949(7) | −.2217(6) | .1871(7) | 5.4(6) |
| O9' | .3601(8) | −.2989(6) | .2147(7) | 5.7(6) |
| N1' | .8588(8) | .6163(6) | .9670(8) | 4.1(6) |
| N2' | .6486(8) | .0452(7) | .5471(8) | 4.1(5) |
| C1' | .8416(9) | .1879(8) | .7204(9) | 3.5(6) |
| C2' | .7294(9) | .1914(7) | .6893(9) | 3.1(6) |
| C3' | .7045(9) | .2721(8) | .7359(9) | 3.5(6) |
| C4' | .8002(9) | .3560(8) | .8177(8) | 3.2(6) |
| C5' | .7879(9) | .4447(7) | .8612(9) | 3.5(6) |
| C6' | .8753(9) | .5209(8) | .9254(9) | 3.7(6) |
| C7' | .9888(10) | .5140(8) | .9623(10) | 4.3(7) |
| C8' | 1.0073(9) | .4293(8) | .9184(8) | 3.3(6) |
| C9' | .9155(8) | .3495(7) | .8475(8) | 2.9(5) |
| C10' | .6276(9) | .1139(7) | .6061(8) | 3.2(6) |
| C11' | 1.1265(9) | .4092(10) | .9517(10) | 4.7(6) |
| C12' | .5698(9) | −.0403(7) | .4589(8) | 3.1(6) |
| C13' | .4540(10) | −.0515(8) | .4067(9) | 3.9(6) |
| C14' | .3831(9) | −.1379(8) | .3220(9) | 3.6(6) |
| C5" | .3140(10) | .0037(8) | .6013(9) | 4.0(7) |
| C6" | .2107(10) | −.0736(7) | .5258(8) | 3.4(6) |
| C7" | .1040(8) | −.0646(7) | .4979(8) | 3.2(6) |
| C8" | .0894(10) | .0267(8) | .5440(9) | 3.7(6) |
| C9" | .1908(9) | .0955(8) | .6167(8) | 3.3(6) |
| C10" | .4795(9) | .3328(8) | .8640(9) | 3.9(6) |
| C11" | −.0254(10) | .0309(7) | .5203(10) | 4.7(7) |
| C12" | .5342(10) | .4863(8) | 1.0047(10) | 4.2(7) |
| C13" | .6478(9) | .4981(8) | 1.0585(8) | 3.2(5) |
| C14" | .7195(10) | .5872(8) | 1.1427(9) | 3.7(6) |
| C15" | .6709(10) | .6576(8) | 1.1691(9) | 4.0(7) |
| C16" | .5569(12) | .6466(10) | 1.1154(10) | 5.6(8) |
| C17" | .4826(10) | .5593(9) | 1.0328(10) | 4.5(7) |
| C18" | .8433(10) | .5963(10) | 1.2052(10) | 4.7(7) |
| O1''' | 1.3437(6) | .8142(7) | 1.0119(6) | 4.2(4) |
| O2''' | 1.2844(6) | .6656(6) | .9054(7) | 5.0(5) |
| O3''' | 1.1780(7) | 1.1705(6) | 1.1440(8) | 5.8(5) |
| O4''' | 1.3565(7) | 1.2310(6) | 1.2537(7) | 5.3(5) |
| O5''' | 1.4997(6) | 1.1307(5) | 1.2528(6) | 4.2(4) |
| O6''' | .9429(6) | .6593(6) | .8041(7) | 4.3(5) |
| O7''' | .6379(6) | .4236(6) | .5748(7) | 4.9(5) |
| O8''' | .6041(6) | .2855(6) | .4629(6) | 4.2(4) |
| O9''' | .7739 | .2251 | .4633 | 4.3(4) |
| N1''' | 1.2731(9) | 1.1642(7) | 1.1797(8) | 4.4(6) |
| N2''' | 1.0571(6) | .5819(6) | .7735(6) | 2.9(4) |
| C1''' | 1.2573(8) | .7327(8) | .9344(9) | 3.5(6) |
| C2''' | 1.1390(8) | .7410(6) | .9019(8) | 2.6(5) |
| C3''' | 1.1263(8) | .8209(8) | .9425(9) | 3.5(6) |
| C4''' | 1.2145(9) | .9032(8) | 1.0234(9) | 3.5(6) |
| C5''' | 1.2013(8) | .9957(8) | 1.0675(8) | 3.0(6) |
| C6''' | 1.2935(9) | 1.0738(8) | 1.1433(9) | 3.7(6) |
| C7''' | 1.4097(9) | 1.0635(8) | 1.1804(8) | 3.6(6) |
| C8''' | 1.4234(8) | .9738(7) | 1.1325(8) | 3.1(6) |
| C9''' | 1.3278(8) | .8980(7) | 1.0563(8) | 3.1(5) |
| C10''' | 1.0409(8) | .6528(8) | .8132(9) | 3.6(6) |
| C11''' | 1.5417(9) | .9660(9) | 1.1681(10) | 4.4(7) |
| C12''' | .9817(9) | .4885(8) | .6926(9) | 3.4(6) |
| C13''' | .8623(8) | .4737(7) | .6512(8) | 2.6(5) |
| C14''' | .7911(9) | .3833(8) | .5746(8) | 3.3(5) |
| C15''' | .8381(10) | .3138(8) | .5443(8) | 3.9(7) |
| C16''' | .9604(9) | .3291(9) | .5824(9) | 4.0(6) |
| C17''' | 1.0270(10) | .4214(8) | .6586(10) | 4.2(7) |
| C18''' | .6711(9) | .3654(8) | .5312(9) | 3.5(6) |
| O1A | .0310(8) | −.0529(7) | .2239(9) | 7.7(7) |
| N1A | −.1542(8) | −.0842(7) | .1334(8) | 4.8(6) |
| C1A | −.0611(11) | −.1047(10) | .1456(12) | 5.6(8) |
| C2A | −.1542(13) | .0006(14) | .2061(14) | 8.7(11) |
| C3A | −.2647(11) | −.1460(11) | .0309(12) | 6.5(8) |
| O1B | .0644(7) | .5005(8) | .2366(7) | 7.8(6) |
| N1B | .2589(9) | .5253(8) | .3317(9) | 5.4(6) |
| C1B | .1594(13) | .5432(10) | .3118(13) | 6.8(10) |
| C2B | .3643(12) | .5824(10) | .4163(11) | 5.7(8) |
| C3B | .2648(13) | .4524(14) | .2581(13) | 8.5(11) |
| O1C | .6696(7) | .0718(7) | −.0628(9) | 6.7(6) |
| N1C | .8368(9) | .1892(7) | .0121(9) | 5.1(6) |
| C1C | .7251(11) | .1590(10) | −.0211(11) | 5.4(8) |
| C2C | .8923(12) | .2935(12) | .0733(11) | 6.3(9) |
| C3C | .8944(11) | .1236(13) | −.0018(15) | 7.8(12) |
| O1D | .2299(9) | .5584(9) | .5949(11) | 7.0(8) |
| N1D | .4015(10) | .6422(10) | .7376(10) | 4.9(6) |
| C1D | .3022(17) | .6196(12) | .6684(12) | 7.3(14) |
| C2D | .4334(18) | .5449(15) | .7385(15) | 7.5(13) |
| C3D | .4784(14) | .7112(13) | .8238(14) | 5.4(10) |
| O1E | .8726(10) | .8983(9) | .8691(11) | 5.6(8) |
| N1E | .6987(11) | .8162(10) | .7331(10) | 3.8(7) |
| C1E | .8079(13) | .8123(13) | .8080(14) | 4.3(10) |
| C2E | .6525(22) | .8852(20) | .7209(21) | 8.8(19) |
| C3E | .6440(16) | .7036(14) | .6594(16) | 5.2(11) |
| O1F | .4299(7) | .3734(7) | .5319(9) | 7.2(6) |
| N1F | .2665(9) | .2528(8) | .4453(8) | 5.1(6) |
| C1F | .3746(10) | .2860(10) | .4833(10) | 5.0(7) |
| C2F | .1947(14) | .1504(11) | .3806(13) | 7.2(11) |
| C3F | .1949(15) | .3246(14) | .4538(17) | 9.6(14) |

TABLE 2

The bond length values of the sample of crystalline form I of XLF-III-43 (Å)

| Bonding atoms | Bond length |
|---|---|
| O(1)—C(1) | 1.554(15) |
| O(1)—C(9) | 1.364(12) |
| O(2)—C(1) | 1.229(15) |
| O(3)—N(1) | 1.200(13) |
| O(4)—N(1) | 1.391(15) |
| O(5)—C(7) | 1.564(15) |
| O(5)—Ho(5) | .848(19) |
| O(6)—C(10) | 1.167(14) |
| O(7)—C(18) | 1.307(14) |
| O(7)—Ho(7) | .785(18) |
| O(8)—C(18) | 1.338(16) |
| O(8)—Ho(9) | 1.617(18) |
| O(9)—C(15) | 1.479(14) |
| O(9)—Ho(9) | 1.072(18) |
| N(1)—C(6) | 1.461(14) |
| N(2)—C(10) | 1.455(13) |
| N(2)—C(12) | 1.530(16) |
| N(2)—Hn(2) | 1.124(19) |
| C(1)—C(2) | 1.372(17) |
| C(2)—C(3) | 1.372(15) |
| C(2)—C(10) | 1.626(18) |
| C(3)—C(4) | 1.625(16) |
| C(3)—H(3) | 1.105(19) |
| C(4)—C(5) | 1.331(15) |
| C(4)—C(9) | 1.363(16) |
| C(5)—C(6) | 1.553(17) |
| C(5)—H(5) | 1.132(19) |

TABLE 2-continued

The bond length values of the sample of crystalline form I of XLF-III-43 (Å)

| Bonding atoms | Bond length |
|---|---|
| C(6)—C(7) | 1.321(16) |
| C(7)—C(8) | 1.364(16) |
| C(8)—C(9) | 1.512(18) |
| C(8)—C(11) | 1.505(16) |
| C(11)—H(11A) | 1.070(30) |
| C(11)—H(11B) | 1.080(30) |
| C(11)—H(11C) | 1.096(22) |
| C(12)—C(13) | 1.429(16) |
| C(12)—C(17) | 1.381(15) |
| C(13)—C(14) | 1.554(17) |
| C(13)—H(13) | 1.085(18) |
| C(14)—C(15) | 1.311(13) |
| C(14)—C(18) | 1.615(16) |
| C(15)—C(16) | 1.400(17) |
| C(16)—C(17) | 1.486(19) |
| C(16)—H(16) | 1.107(19) |
| C(17)—H(17) | 1.083(22) |
| O(1')—C(1') | 1.503(15) |
| O(1')—C(9') | 1.324(12) |
| O(2')—C(1') | 1.159(13) |
| O(3')—N(1') | 1.149(15) |
| O(4')—N(1') | 1.386(15) |
| O(4')—Ho(5') | 1.639(19) |
| O(5')—C(7') | 1.505(16) |
| O(5')—Ho(5') | 1.114(19) |
| O(6')—C(10') | 1.299(14) |
| O(7')—C(18') | 1.235(14) |
| O(7')—Ho(7') | 1.033(20) |
| O(8')—C(18') | 1.351(16) |
| O(9')—C(15') | 1.485(17) |
| O(9')—Ho(9') | 1.029(21) |
| N(1')—C(6') | 1.444(14) |
| N(2')—C(10') | 1.302(14) |
| N(2')—C(12') | 1.597(15) |
| N(2')—Hn(2') | 1.077(20) |
| C(1')—C(2') | 1.407(16) |
| C(2')—C(3') | 1.348(15) |
| C(2')—C(10') | 1.640(17) |
| C(3')—C(4') | 1.643(17) |
| C(3')—H(3') | 1.113(19) |
| C(4')—C(5') | 1.355(15) |
| C(4')—C(9') | 1.447(15) |
| C(5')—C(6') | 1.467(18) |
| C(5')—H(5') | 1.067(19) |
| C(6')—C(7') | 1.416(17) |
| C(7')—C(8') | 1.340(15) |
| C(8')—C(9') | 1.548(17) |
| C(8')—C(11') | 1.530(16) |
| C(11')—H(11'A) | 1.079(24) |
| C(11')—H(11'B) | 1.101(23) |
| C(11')—H(11'C) | 1.07(3) |
| C(12')—C(13') | 1.417(17) |
| C(12')—C(17') | 1.253(16) |
| C(13')—C(14') | 1.548(18) |
| C(13')—H(13') | 1.078(18) |
| C(14')—C(15') | 1.317(16) |
| C(14')—C(18') | 1.514(18) |
| C(15')—C(16') | 1.448(20) |
| C(16')—C(17') | 1.496(20) |
| C(16')—H(16') | 1.143(19) |
| C(17')—H(17') | 1.076(22) |
| O(1")—C(1") | 1.582(15) |
| O(1")—C(9") | 1.390(13) |
| O(2")—C(1") | 1.152(14) |
| O(3")—N(1") | 1.258(15) |
| O(4")—N(1") | 1.351(16) |
| O(4")—Ho(5") | 1.532(18) |
| O(5")—C(7") | 1.526(15) |
| O(5")—Ho(5") | .964(19) |
| O(6")—C(10") | 1.155(14) |
| O(7")—C(18") | 1.277(16) |
| O(7")—Ho(7") | .861(24) |
| O(8")—C(18") | 1.360(17) |
| O(9")—C(15") | 1.509(15) |
| O(9")—Ho(9") | .942(23) |
| N(1")—C(6") | 1.393(15) |
| N(2")—C(10") | 1.318(14) |
| N(2")—C(12") | 1.537(17) |
| N(2")—Hn(2") | 1.108(20) |
| C(1")—C(2") | 1.496(16) |
| C(2")—C(3") | 1.270(14) |
| C(2")—C(10") | 1.700(17) |
| C(3")—C(4") | 1.552(17) |
| C(3")—H(3") | 1.077(19) |
| C(4")—C(5") | 1.379(16) |
| C(4")—C(9") | 1.341(16) |
| C(5")—C(6") | 1.622(18) |
| C(5")—H(5") | 1.148(20) |
| C(6")—C(7") | 1.340(16) |
| C(7")—C(8") | 1.408(17) |
| C(8")—C(9") | 1.540(17) |
| C(8")—C(11") | 1.455(18) |
| C(11")—H(11"A) | 1.130(30) |
| C(11")—H(11"B) | 1.060(22) |
| C(11")—H(11"C) | 1.110(30) |
| C(12")—C(13") | 1.395(17) |
| C(12")—C(17") | 1.360(15) |
| C(13")—C(14") | 1.578(17) |
| C(13")—H(13") | 1.134(19) |
| C(14")—C(15") | 1.293(15) |
| C(14")—C(18") | 1.521(18) |
| C(15")—C(16") | 1.404(20) |
| C(15")—Ho(9") | 1.679(25) |
| C(16")—C(17") | 1.563(20) |
| C(16")—H(16") | 1.093(20) |
| C(17")—H(17") | 1.127(22) |
| O(1"')—C(1"') | 1.547(15) |
| O(1"')—C(9"') | 1.321(13) |
| O(2"')—C(1"') | 1.103(13) |
| O(3"')—N(1"') | 1.177(14) |
| O(4"')—N(1"') | 1.395(14) |
| O(5"')—C(7"') | 1.436(15) |
| O(5"')—Ho(5"') | .822(18) |
| O(6"')—C(10"') | 1.294(13) |
| O(7"')—C(18"') | 1.169(13) |
| O(7"')—Ho(7"') | .931(19) |
| O(8"')—C(18"') | 1.387(15) |
| O(9"')—C(15"') | 1.524(12) |
| O(9"')—Ho(9"') | .889(17) |
| N(1"')—C(6"') | 1.372(15) |
| N(2"')—C(10"') | 1.147(14) |
| N(2"')—C(12"') | 1.618(15) |
| N(2"')—Hn(2"') | 1.081(18) |
| C(1"')—C(2"') | 1.476(14) |
| C(2"')—C(3"') | 1.230(15) |
| C(2"')—C(10"') | 1.722(16) |
| C(3"')—C(4"') | 1.583(18) |
| C(3"')—H(3"') | 1.099(19) |
| C(4"')—C(5"') | 1.405(16) |
| C(4"')—C(9"') | 1.415(15) |
| C(5"')—C(6"') | 1.556(18) |
| C(5"')—H(5"') | 1.056(19) |
| C(6"')—C(7"') | 1.451(16) |
| C(7"')—C(8"') | 1.399(16) |
| C(8"')—C(9"') | 1.554(16) |
| C(8"')—C(11"') | 1.474(16) |
| C(11"')—H(11"'A) | 1.066(24) |
| C(11"')—H(11"'B) | 1.120(30) |
| C(11"')—H(11"'C) | 1.088(23) |
| C(12"')—C(13"') | 1.471(16) |
| C(12"')—C(17"') | 1.279(16) |
| C(13"')—C(14"') | 1.554(16) |
| C(13"')—H(13"') | 1.116(19) |
| C(14"')—C(15"') | 1.294(16) |
| C(14"')—C(18"') | 1.482(16) |
| C(15"')—C(16"') | 1.517(18) |
| C(16"')—C(17"') | 1.548(19) |
| C(16"')—H(16"') | 1.072(19) |

TABLE 2-continued

The bond length values of the sample of crystalline form I of XLF-III-43 (Å)

| Bonding atoms | Bond length |
| --- | --- |
| C(17''')—H(17''') | 1.109(22) |
| O(1A)—C(1A) | 1.368(19) |
| N(1A)—C(1A) | 1.254(16) |
| N(1A)—C(2A) | 1.467(19) |
| N(1A)—C(3A) | 1.689(19) |
| C(1A)—Hc(1A) | 1.104(24) |
| C(2A)—Hc(2AA) | 1.080(30) |
| C(2A)—Hc(2AB) | 1.150(30) |
| C(2A)—Hc(2AC) | 1.070(30) |
| C(3A)—Hc(3AA) | 1.130(30) |
| C(3A)—Hc(3AB) | 1.096(24) |
| C(3A)—Hc(3AC) | 1.049(20) |
| O(1B)—C(1B) | 1.331(21) |
| N(1B)—C(1B) | 1.291(19) |
| N(1B)—C(2B) | 1.528(20) |
| N(1B)—C(3B) | 1.375(19) |
| C(1B)—Hc(1B) | 1.084(24) |
| C(2B)—Hc(2BA) | 1.107(24) |
| C(2B)—Hc(2BB) | 1.060(30) |
| C(2B)—Hc(2BC) | 1.107(22) |
| C(3B)—Hc(3BA) | 1.160(30) |
| C(3B)—Hc(3BB) | 1.100(30) |
| C(3B)—Hc(3BC) | .992(23) |
| O(1C)—C(1C) | 1.348(19) |
| N(1C)—C(1C) | 1.422(19) |
| N(1C)—C(2C) | 1.579(20) |
| N(1C)—C(3C) | 1.252(20) |
| C(1C)—Hc(1C) | 1.143(20) |
| C(2C)—Hc(2CA) | 1.094(24) |
| C(2C)—Hc(2CB) | 1.070(30) |
| C(2C)—Hc(2CC) | 1.087(23) |
| C(3C)—Hc(3CA) | 1.060(30) |
| C(3C)—Hc(3CB) | 1.080(30) |
| C(3C)—Hc(3CC) | 1.160(30) |
| O(1D)—C(1D) | 1.270(30) |
| N(1D)—C(1D) | 1.300(30) |
| N(1D)—C(2D) | 1.472(24) |
| N(1D)—C(3D) | 1.448(24) |
| C(1D)—Hc(1D) | 1.146(21) |
| O(1E)—C(1E) | 1.423(25) |
| N(1E)—C(1E) | 1.426(22) |
| N(1E)—C(2E) | 1.180(30) |
| N(1E)—C(3E) | 1.740(30) |
| C(1E)—Hc(1E) | 1.188(23) |
| C(2E)—Hc(2EA) | 1.130(30) |
| C(2E)—Hc(2EB) | 1.180(40) |
| C(2E)—Hc(2EC) | 1.100(30) |
| C(3E)—Hc(3EA) | 1.120(30) |
| C(3E)—Hc(3EB) | 1.040(30) |
| C(3E)—Hc(3EC) | 1.120(30) |
| O(1F)—C(1F) | 1.357(18) |
| N(1F)—C(1F) | 1.380(18) |
| N(1F)—C(2F) | 1.639(20) |
| N(1F)—C(3F) | 1.450(18) |
| C(1F)—Hc(1F) | 1.104(19) |
| C(2F)—Hc(2FA) | 1.070(30) |
| C(2F)—Hc(2FB) | 1.079(25) |
| C(2F)—Hc(2FC) | 1.090(30) |
| C(3F)—Hc(3FA) | 1.100(30) |
| C(3F)—Hc(3FB) | 1.090(30) |
| C(3F)—Hc(3FC) | 1.110(30) |

TABLE 3

The bond angle values of the sample of crystalline form I of XLF-III-43 (°)

| Bonding atoms | Bond angle |
| --- | --- |
| C(1)—O(1)—C(9) | 124.7(9) |
| C(7)—O(5)—Ho(5) | 115.0(16) |
| C(18)—O(7)—Ho(7) | 127.9(20) |
| C(15)—O(9)—Ho(9) | 103.8(13) |
| O(3)—N(1)—O(4) | 127.1(9) |
| O(3)—N(1)—C(6) | 109.6(10) |
| O(4)—N(1)—C(6) | 123.2(9) |
| C(10)—N(2)—C(12) | 125.3(9) |
| C(10)—N(2)—Hn(2) | 116.7(15) |
| C(12)—N(2)—Hn(2) | 118.0(13) |
| O(1)—C(1)—O(2) | 114.9(11) |
| O(1)—C(1)—C(2) | 126.8(10) |
| O(2)—C(1)—C(2) | 117.9(12) |
| C(1)—C(2)—C(3) | 110.1(11) |
| C(1)—C(2)—C(10) | 131.7(10) |
| C(3)—C(2)—C(10) | 118.0(9) |
| C(2)—C(3)—C(4) | 122.3(9) |
| C(2)—C(3)—H(3) | 120.6(15) |
| C(4)—C(3)—H(3) | 117.0(14) |
| C(3)—C(4)—C(5) | 124.7(10) |
| C(3)—C(4)—C(9) | 125.7(9) |
| C(5)—C(4)—C(9) | 109.6(11) |
| C(4)—C(5)—C(6) | 120.9(10) |
| C(4)—C(5)—H(5) | 121.9(16) |
| C(6)—C(5)—H(5) | 117.2(14) |
| N(1)—C(6)—C(5) | 121.0(9) |
| N(1)—C(6)—C(7) | 109.7(10) |
| C(5)—C(6)—C(7) | 129.1(9) |
| O(5)—C(7)—C(6) | 130.3(10) |
| O(5)—C(7)—C(8) | 119.2(10) |
| C(6)—C(7)—C(8) | 110.5(11) |
| C(7)—C(8)—C(9) | 120.1(10) |
| C(7)—C(8)—C(11) | 112.8(11) |
| C(9)—C(8)—C(11) | 127.1(10) |
| O(1)—C(9)—C(4) | 110.0(10) |
| O(1)—C(9)—C(8) | 120.1(9) |
| C(4)—C(9)—C(8) | 129.8(9) |
| O(6)—C(10)—N(2) | 112.3(11) |
| O(6)—C(10)—C(2) | 130.7(9) |
| N(2)—C(10)—C(2) | 116.0(9) |
| C(8)—C(11)—H(11A) | 112.2(14) |
| C(8)—C(11)—H(11B) | 111.8(13) |
| C(8)—C(11)—H(11C) | 103.4(15) |
| H(11A)—C(11)—H(11B) | 108.3(20) |
| H(11A)—C(11)—H(11C) | 109.6(18) |
| H(11B)—C(11)—H(11C) | 111.5(19) |
| N(2)—C(12)—C(13) | 136.6(9) |
| N(2)—C(12)—C(17) | 115.2(10) |
| C(13)—C(12)—C(17) | 108.1(10) |
| C(12)—C(13)—C(14) | 128.3(8) |
| C(12)—C(13)—H(13) | 117.7(16) |
| C(14)—C(13)—H(13) | 114.1(15) |
| C(13)—C(14)—C(15) | 122.6(10) |
| C(13)—C(14)—C(18) | 127.3(8) |
| C(15)—C(14)—C(18) | 110.1(10) |
| O(9)—C(15)—C(14) | 123.2(10) |
| O(9)—C(15)—C(16) | 129.1(8) |
| C(14)—C(15)—C(16) | 107.5(10) |
| C(15)—C(16)—C(17) | 133.4(9) |
| C(15)—C(16)—H(16) | 113.0(16) |
| C(17)—C(16)—H(16) | 113.6(16) |
| C(12)—C(17)—C(16) | 120.0(11) |
| C(12)—C(17)—H(17) | 118.4(16) |
| C(16)—C(17)—H(17) | 121.6(15) |
| O(7)—C(18)—O(8) | 127.2(10) |
| O(7)—C(18)—C(14) | 103.8(10) |
| O(8)—C(18)—C(14) | 128.5(9) |
| C(1')—O(1')—C(9') | 130.6(8) |
| C(7')—O(5')—Ho(5') | 113.3(13) |
| C(18')—O(7')—Ho(7') | 113.1(15) |
| C(15')—O(9')—Ho(9') | 121.9(14) |
| O(3')—N(1')—O(4') | 125.2(9) |
| O(3')—N(1')—C(6') | 108.7(10) |
| O(4')—N(1')—C(6') | 125.3(10) |
| C(10')—N(2')—C(12') | 130.7(9) |
| C(10')—N(2')—Hn(2') | 115.0(15) |
| C(12')—N(2')—Hn(2') | 114.2(14) |

TABLE 3-continued

The bond angle values of the sample of crystalline form I of XLF-III-43 (°)

| Bonding atoms | Bond angle |
|---|---|
| O(1')—C(1')—O(2') | 121.1(10) |
| O(1')—C(1')—C(2') | 123.2(9) |
| O(2')—C(1')—C(2') | 114.7(12) |
| C(1')—C(2')—C(3') | 113.0(11) |
| C(1')—C(2')—C(10') | 129.6(9) |
| C(3')—C(2')—C(10') | 117.4(9) |
| C(2')—C(3')—C(4') | 121.0(10) |
| C(2')—C(3')—H(3') | 120.8(16) |
| C(4')—C(3')—H(3') | 118.2(15) |
| C(3')—C(4')—C(5') | 128.1(10) |
| C(3')—C(4')—C(9') | 124.2(9) |
| C(5')—C(4')—C(9') | 107.5(10) |
| C(4')—C(5')—C(6') | 126.3(10) |
| C(4')—C(5')—H(5') | 117.7(16) |
| C(6')—C(5')—H(5') | 115.9(15) |
| N(1')—C(6')—C(5') | 124.9(10) |
| N(1')—C(6')—C(7') | 107.6(10) |
| C(5')—C(6')—C(7') | 127.4(9) |
| O(5')—C(7')—C(6') | 132.4(10) |
| O(5')—C(7')—C(8') | 118.2(11) |
| C(6')—C(7')—C(8') | 109.2(11) |
| C(7')—C(8')—C(9') | 123.6(10) |
| C(7')—C(8')—C(11') | 115.9(11) |
| C(9')—C(8')—C(11') | 120.1(9) |
| O(1')—C(9')—C(4') | 106.9(10) |
| O(1')—C(9')—C(8') | 127.5(9) |
| C(4')—C(9')—C(8') | 125.5(9) |
| O(6')—C(10')—N(2') | 114.0(11) |
| O(6')—C(10')—C(2') | 128.4(9) |
| N(2')—C(10')—C(2') | 117.6(9) |
| C(8')—C(11')—H(11'A) | 109.2(14) |
| C(8')—C(11')—H(11'B) | 106.7(14) |
| C(8')—C(11')—H(11'C) | 106.6(13) |
| H(11'A)—C(11')—H(11'B) | 106.0(18) |
| H(11'A)—C(11')—H(11'C) | 114.3(20) |
| H(11'B)—C(11')—H(11'C) | 113.8(20) |
| N(2')—C(12')—C(13') | 129.3(8) |
| N(2')—C(12')—C(17') | 120.5(11) |
| C(13')—C(12')—C(17') | 109.9(11) |
| C(12')—C(13')—C(14') | 126.5(9) |
| C(12')—C(13')—H(13') | 117.2(17) |
| C(14')—C(13')—H(13') | 116.1(16) |
| C(13')—C(14')—C(15') | 122.1(11) |
| C(13')—C(14')—C(18') | 127.2(10) |
| C(15')—C(14')—C(18') | 110.4(11) |
| O(9')—C(15')—C(14') | 123.6(12) |
| O(9')—C(15')—C(16') | 127.3(10) |
| C(14')—C(15')—C(16') | 109.1(12) |
| C(15')—C(16')—C(17') | 126.4(10) |
| C(15')—C(16')—H(16') | 115.9(16) |
| C(17')—C(16')—H(16') | 117.6(16) |
| C(12')—C(17')—C(16') | 125.8(12) |
| C(12')—C(17')—H(17') | 119.2(18) |
| C(16')—C(17')—H(17') | 114.8(15) |
| O(7')—C(18')—O(8') | 123.2(12) |
| O(7')—C(18')—C(14') | 106.1(11) |
| O(8')—C(18')—C(14') | 128.8(10) |
| C(1")—O(1")—C(9") | 124.1(8) |
| C(7")—O(5")—Ho(5") | 112.3(15) |
| C(18")—O(7")—Ho(7") | 77.4(14) |
| C(15")—O(9")—Ho(9") | 83.1(16) |
| O(3")—N(1")—O(4") | 127.1(10) |
| O(3")—N(1")—C(6") | 109.0(11) |
| O(4")—N(1")—C(6") | 122.9(10) |
| C(10")—N(2")—C(12") | 128.2(10) |
| C(10")—N(2")—Hn(2") | 114.3(15) |
| C(12")—N(2")—Hn(2") | 117.4(14) |
| O(1")—C(1")—O(2") | 114.7(10) |
| O(1")—C(1")—C(2") | 121.3(9) |
| O(2")—C(1")—C(2") | 123.2(11) |
| C(1")—C(2")—C(3") | 108.7(10) |
| C(1")—C(2")—C(10") | 123.6(9) |
| C(3")—C(2")—C(10") | 127.7(9) |
| C(2")—C(3")—C(4") | 129.6(10) |
| C(2")—C(3")—H(3") | 116.3(16) |
| C(4")—C(3")—H(3") | 114.1(15) |
| C(3")—C(4")—C(5") | 127.4(10) |
| C(3")—C(4")—C(9") | 125.4(9) |
| C(5")—C(4")—C(9") | 107.0(11) |
| C(4")—C(5")—C(6") | 120.8(10) |
| C(4")—C(5")—H(5") | 119.0(16) |
| C(6")—C(5")—H(5") | 120.1(15) |
| N(1")—C(6")—C(5") | 118.9(10) |
| N(1")—C(6")—C(7") | 112.2(11) |
| C(5")—C(6")—C(7") | 128.8(10) |
| O(5")—C(7")—C(6") | 126.1(10) |
| O(5")—C(7")—C(8") | 124.0(9) |
| C(6")—C(7")—C(8") | 109.9(11) |
| C(7")—C(8")—C(9") | 118.6(10) |
| C(7")—C(8")—C(11") | 108.8(11) |
| C(9")—C(8")—C(11") | 132.1(10) |
| O(1")—C(9")—C(4") | 110.7(10) |
| O(1")—C(9")—C(8") | 114.7(9) |
| C(4")—C(9")—C(8") | 134.7(10) |
| O(6")—C(10")—N(2") | 119.2(11) |
| O(6")—C(10")—C(2") | 121.3(10) |
| N(2")—C(10")—C(2") | 119.5(10) |
| C(8")—C(11")—H(11"A) | 114.3(12) |
| C(8")—C(11")—H(11"B) | 117.9(16) |
| C(8")—C(11")—H(11"C) | 105.1(15) |
| H(11"A)—C(11")—H(11"B) | 108.3(19) |
| H(11"A)—C(11")—H(11"C) | 104.2(19) |
| H(11"B)—C(11")—H(11"C) | 105.7(17) |
| N(2")—C(12")—C(13") | 131.3(9) |
| N(2")—C(12")—C(17") | 114.3(11) |
| C(13")—C(12")—C(17") | 114.4(12) |
| C(12")—C(13")—C(14") | 127.3(10) |
| C(12")—C(13")—H(13") | 117.4(15) |
| C(14")—C(13")—H(13") | 115.2(15) |
| C(13")—C(14")—C(15") | 118.8(11) |
| C(13")—C(14")—C(18") | 126.3(9) |
| C(15")—C(14")—C(18") | 114.7(12) |
| O(9")—C(15")—C(14") | 120.5(12) |
| O(9")—C(15")—C(16") | 125.2(10) |
| C(14")—C(15")—C(16") | 114.3(12) |
| C(15")—C(16")—C(17") | 128.6(10) |
| C(15")—C(16")—H(16") | 115.2(17) |
| C(17")—C(16")—H(16") | 116.0(17) |
| C(12")—C(17")—C(16") | 116.5(12) |
| C(12")—C(17")—H(17") | 119.0(16) |
| C(16")—C(17")—H(17") | 124.4(14) |
| O(7")—C(18")—O(8") | 126.0(12) |
| O(7")—C(18")—C(14") | 103.6(11) |
| O(8")—C(18")—C(14") | 129.0(11) |
| C(1''')—O(1''')—C(9''') | 128.4(8) |
| C(7''')—O(5''')—Ho(5''') | 111.2(17) |
| C(18''')—O(7''')—Ho(7''') | 118.2(17) |
| C(15''')—O(9''')—Ho(9''') | 108.4(15) |
| O(3''')—N(1''')—O(4''') | 128.1(9) |
| O(3''')—N(1''')—C(6''') | 109.6(10) |
| O(4''')—N(1''')—C(6''') | 122.1(10) |
| C(10''')—N(2''')—C(12''') | 135.2(9) |
| C(10''')—N(2''')—Hn(2''') | 113.5(15) |
| C(12''')—N(2''')—Hn(2''') | 111.3(14) |
| O(1''')—C(1''')—O(2''') | 119.3(10) |
| O(1''')—C(1''')—C(2''') | 121.7(8) |
| O(2''')—C(1''')—C(2''') | 118.9(11) |
| C(1''')—C(2''')—C(3''') | 108.9(10) |
| C(1''')—C(2''')—C(10''') | 122.6(8) |
| C(3''')—C(2''')—C(10''') | 128.2(9) |
| C(2''')—C(3''')—C(4''') | 129.6(10) |
| C(2''')—C(3''')—H(3''') | 114.7(16) |
| C(4''')—C(3''')—H(3''') | 115.7(15) |
| C(3''')—C(4''')—C(5''') | 130.5(10) |
| C(3''')—C(4''')—C(9''') | 123.2(9) |
| C(5''')—C(4''')—C(9''') | 106.0(10) |
| C(4''')—C(5''')—C(6''') | 126.9(9) |
| C(4''')—C(5''')—H(5''') | 116.5(16) |
| C(6''')—C(5''')—H(5''') | 116.6(15) |
| N(1''')—C(6''')—C(5''') | 123.0(10) |

TABLE 3-continued

The bond angle values of the sample of crystalline form I of XLF-III-43 (°)

| Bonding atoms | Bond angle |
|---|---|
| N(1''')—C(6''')—C(7''') | 112.0(11) |
| C(5''')—C(6''')—C(7''') | 125.0(10) |
| O(5''')—C(7''')—C(6''') | 128.5(10) |
| O(5''')—C(7''')—C(8''') | 122.9(9) |
| C(6''')—C(7''')—C(8''') | 108.6(11) |
| C(7''')—C(8''')—C(9''') | 124.1(9) |
| C(7''')—C(8''')—C(11''') | 107.5(10) |
| C(9''')—C(8''')—C(11''') | 128.5(9) |
| O(1''')—C(9''')—C(4''') | 108.1(10) |
| O(1''')—C(9''')—C(8''') | 122.7(9) |
| C(4''')—C(9''')—C(8''') | 129.2(9) |
| O(6''')—C(10''')—N(2''') | 115.7(11) |
| O(6''')—C(10''')—C(2''') | 117.2(9) |
| N(2''')—C(10''')—C(2''') | 125.8(9) |
| C(8''')—C(11''')—H(11'''A) | 115.6(15) |
| C(8''')—C(11''')—H(11'''B) | 113.6(12) |
| C(8''')—C(11''')—H(11'''C) | 105.8(15) |
| H(11'''A)—C(11''')—H(11'''B) | 107.7(20) |
| H(11'''A)—C(11''')—H(11'''C) | 106.6(17) |
| H(11'''B)—C(11''')—H(11'''C) | 107.0(19) |
| N(2''')—C(12''')—C(13''') | 125.6(9) |
| N(2''')—C(12''')—C(17''') | 119.0(10) |
| C(13''')—C(12''')—C(17''') | 115.3(11) |
| C(12''')—C(13''')—C(14''') | 125.3(9) |
| C(12''')—C(13''')—H(13''') | 115.0(15) |
| C(14''')—C(13''')—H(13''') | 119.8(14) |
| C(13''')—C(14''')—C(15''') | 118.9(11) |
| C(13''')—C(14''')—C(18''') | 126.8(12) |
| C(15''')—C(14''')—C(18''') | 114.3(11) |
| O(9''')—C(15''')—C(14''') | 122.6(11) |
| O(9''')—C(15''')—C(16''') | 120.3(9) |
| C(14''')—C(15''')—C(16''') | 116.7(11) |
| C(15''')—C(16''')—C(17''') | 121.8(9) |
| C(15''')—C(16''')—H(16''') | 119.5(17) |
| C(17''')—C(16''')—H(16''') | 118.8(16) |
| C(12''')—C(17''')—C(16''') | 121.9(11) |
| C(12''')—C(17''')—H(17''') | 117.5(16) |
| C(16''')—C(17''')—H(17''') | 120.5(14) |
| O(7''')—C(18''')—O(8''') | 120.8(11) |
| O(7''')—C(18''')—C(14''') | 109.6(11) |
| O(8''')—C(18''')—C(14''') | 128.7(11) |
| C(1A)—N(1A)—C(2A) | 113.8(12) |
| C(1A)—N(1A)—C(3A) | 119.3(11) |
| C(2A)—N(1A)—C(3A) | 126.4(10) |
| O(1A)—C(1A)—N(1A) | 121.3(12) |
| O(1A)—C(1A)—Hc(1A) | 118.8(15) |
| N(1A)—C(1A)—Hc(1A) | 119.8(17) |
| N(1A)—C(2A)—Hc(2AA) | 112.8(21) |
| N(1A)—C(2A)—Hc(2AB) | 110.4(18) |
| N(1A)—C(2A)—Hc(2AC) | 108.6(14) |
| Hc(2AA)—C(2A)—Hc(2AB) | 104.7(16) |
| Hc(2AA)—C(2A)—Hc(2AC) | 113.0(23) |
| Hc(2AB)—C(2A)—Hc(2AC) | 107.0(24) |
| N(1A)—C(3A)—Hc(3AA) | 112.1(17) |
| N(1A)—C(3A)—Hc(3AB) | 110.8(15) |
| N(1A)—C(3A)—Hc(3AC) | 105.8(17) |
| Hc(3AA)—C(3A)—Hc(3AB) | 103.9(19) |
| Hc(3AA)—C(3A)—Hc(3AC) | 110.8(18) |
| Hc(3AB)—C(3A)—Hc(3AC) | 113.6(21) |
| C(1B)—N(1B)—C(2B) | 127.7(12) |
| C(1B)—N(1B)—C(3B) | 112.2(13) |
| C(2B)—N(1B)—C(3B) | 119.4(11) |
| O(1B)—C(1B)—N(1B) | 131.4(13) |
| O(1B)—C(1B)—Hc(1B) | 116.6(17) |
| N(1B)—C(1B)—Hc(1B) | 111.7(18) |
| N(1B)—C(2B)—Hc(2BA) | 110.5(16) |
| N(1B)—C(2B)—Hc(2BB) | 113.3(18) |
| N(1B)—C(2B)—Hc(2BC) | 103.4(17) |
| Hc(2BA)—C(2B)—Hc(2BB) | 108.2(20) |
| Hc(2BA)—C(2B)—Hc(2BC) | 111.1(20) |
| Hc(2BB)—C(2B)—Hc(2BC) | 110.2(18) |
| N(1B)—C(3B)—Hc(3BA) | 107.1(19) |
| N(1B)—C(3B)—Hc(3BB) | 115.3(16) |
| N(1B)—C(3B)—Hc(3BC) | 113.6(20) |
| Hc(3BA)—C(3B)—Hc(3BB) | 101.2(21) |
| Hc(3BA)—C(3B)—Hc(3BC) | 105.8(20) |
| Hc(3BB)—C(3B)—Hc(3BC) | 112.4(24) |
| C(1C)—N(1C)—C(2C) | 124.6(11) |
| C(1C)—N(1C)—C(3C) | 115.1(13) |
| C(2C)—N(1C)—C(3C) | 120.0(13) |
| O(1C)—C(1C)—N(1C) | 131.5(11) |
| O(1C)—C(1C)—Hc(1C) | 117.1(16) |
| N(1C)—C(1C)—Hc(1C) | 111.4(17) |
| N(1C)—C(2C)—Hc(2CA) | 112.9(17) |
| N(1C)—C(2C)—Hc(2CB) | 111.4(17) |
| N(1C)—C(2C)—Hc(2CC) | 105.2(17) |
| Hc(2CA)—C(2C)—Hc(2CB) | 107.6(21) |
| Hc(2CA)—C(2C)—Hc(2CC) | 109.4(19) |
| Hc(2CB)—C(2C)—Hc(2CC) | 110.3(19) |
| N(1C)—C(3C)—Hc(3CA) | 111.8(20) |
| N(1C)—C(3C)—Hc(3CB) | 109.6(19) |
| N(1C)—C(3C)—Hc(3CC) | 109.5(15) |
| Hc(3CA)—C(3C)—Hc(3CB) | 111.2(19) |
| Hc(3CA)—C(3C)—Hc(3CC) | 106.3(22) |
| Hc(3CB)—C(3C)—Hc(3CC) | 108.3(23) |
| C(1D)—N(1D)—C(2D) | 95.2(15) |
| C(1D)—N(1D)—C(3D) | 147.9(13) |
| C(2D)—N(1D)—C(3D) | 114.0(14) |
| O(1D)—C(1D)—N(1D) | 150.2(14) |
| O(1D)—C(1D)—Hc(1D) | 107.6(21) |
| N(1D)—C(1D)—Hc(1D) | 102.0(21) |
| C(1E)—N(1E)—C(2E) | 124.8(20) |
| C(1E)—N(1E)—C(3E) | 110.1(13) |
| C(2E)—N(1E)—C(3E) | 125.1(19) |
| O(1E)—C(1E)—N(1E) | 119.9(14) |
| O(1E)—C(1E)—Hc(1E) | 123.2(18) |
| N(1E)—C(1E)—Hc(1E) | 116.8(20) |
| N(1E)—C(2E)—Hc(2EA) | 116.9(23) |
| N(1E)—C(2E)—Hc(2EB) | 112.5(24) |
| N(1E)—C(2E)—Hc(2EC) | 118.0(30) |
| Hc(2EA)—C(2E)—Hc(2EB) | 100.4(23) |
| Hc(2EA)—C(2E)—Hc(2EC) | 105.3(25) |
| Hc(2EB)—C(2E)—Hc(2EC) | 100.7(25) |
| N(1E)—C(3E)—Hc(3EA) | 113.6(17) |
| N(1E)—C(3E)—Hc(3EB) | 119.1(21) |
| N(1E)—C(3E)—Hc(3EC) | 102.0(18) |
| Hc(3EA)—C(3E)—Hc(3EB) | 108.6(23) |
| Hc(3EA)—C(3E)—Hc(3EC) | 103.6(22) |
| Hc(3EB)—C(3E)—Hc(3EC) | 108.4(20) |
| C(1F)—N(1F)—C(2F) | 135.2(11) |
| C(1F)—N(1F)—C(3F) | 114.7(13) |
| C(2F)—N(1F)—C(3F) | 109.7(13) |
| O(1F)—C(1F)—N(1F) | 133.5(11) |
| O(1F)—C(1F)—Hc(1F) | 112.9(16) |
| N(1F)—C(1F)—Hc(1F) | 113.6(17) |
| N(1F)—C(2F)—Hc(2FA) | 109.8(18) |
| N(1F)—C(2F)—Hc(2FB) | 108.1(16) |
| N(1F)—C(2F)—Hc(2FC) | 106.3(18) |
| Hc(2FA)—C(2F)—Hc(2FB) | 110.7(22) |
| Hc(2FA)—C(2F)—Hc(2FC) | 111.1(19) |
| Hc(2FB)—C(2F)—Hc(2FC) | 110.8(22) |
| N(1F)—C(3F)—Hc(3FA) | 115.4(18) |
| N(1F)—C(3F)—Hc(3FB) | 115.4(17) |
| N(1F)—C(3F)—Hc(3FC) | 106.7(17) |
| Hc(3FA)—C(3F)—Hc(3FB) | 104.8(22) |
| Hc(3FA)—C(3F)—Hc(3FC) | 106.4(21) |
| Hc(3FB)—C(3F)—Hc(3FC) | 107.5(22) |

2. When taking X-ray powder diffraction analysis (CuK$_\alpha$ irradiation), the solid substance of crystalline form I of XLF-III-43 shows diffraction peak position: 2-Theta values (°) or d values (Å), and relative intensity of diffraction peak: values of peak height (Height %). Below is the characteristic peak values of solid substances in crystalline state (Table 4, FIG. 4).

TABLE 4

The characteristic peak values of X-ray powder diffraction of the sample of crystal form I of XLF-III-43

| Peak | 2-Theta | d (Å) | Height % |
|---|---|---|---|
| 1 | 13.3940 | 6.60 | 19 |
| 2 | 12.4622 | 7.09 | 11 |
| 3 | 11.8693 | 7.45 | 9 |
| 4 | 11.8162 | 7.48 | 8 |
| 5 | 10.6137 | 8.33 | 7 |
| 6 | 10.3712 | 8.53 | 69 |
| 7 | 7.0528 | 12.55 | 6 |
| 8 | 6.4666 | 13.69 | 42 |
| 9 | 6.3173 | 14.02 | 14 |
| 10 | 6.0474 | 14.65 | 7 |
| 11 | 5.9081 | 14.99 | 10 |
| 12 | 5.8471 | 15.15 | 3 |
| 13 | 5.7734 | 15.35 | 5 |
| 14 | 5.6435 | 15.70 | 19 |
| 15 | 5.3781 | 16.48 | 12 |
| 16 | 5.3446 | 16.59 | 12 |
| 17 | 5.3069 | 16.71 | 8 |
| 18 | 4.5269 | 19.61 | 13 |
| 19 | 4.4480 | 19.96 | 11 |
| 20 | 4.1832 | 21.24 | 16 |
| 21 | 4.0347 | 22.03 | 4 |
| 22 | 3.9313 | 22.62 | 4 |
| 23 | 3.8921 | 22.85 | 5 |
| 24 | 3.8448 | 23.13 | 3 |
| 25 | 3.8195 | 23.29 | 4 |
| 26 | 3.6530 | 24.37 | 3 |
| 27 | 3.5837 | 24.84 | 11 |
| 28 | 3.5433 | 25.13 | 3 |
| 29 | 3.5379 | 25.17 | 30 |
| 30 | 3.5214 | 25.29 | 10 |
| 31 | 3.4694 | 25.68 | 3 |
| 32 | 3.3660 | 26.48 | 23 |
| 33 | 3.3338 | 26.74 | 3 |
| 34 | 3.3220 | 26.84 | 100 |
| 35 | 3.0567 | 29.21 | 18 |
| 36 | 2.9501 | 30.30 | 3 |

3. In the DSC spectrum of the solid substance of crystalline form I of XLF-III-43 (FIG. 5), there are a peak of heat absorption with the transition value at about 121° C., and a peak of heat emission with the transition value at about 342° C.

4. In the infrared absorption spectrum of the solid substance of crystalline form I of XLF-III-43 (FIG. 6), there are absorption peaks at 3564.6, 3341.8, 3296.2, 3084.9, 2930.4, 1917.2, 1721.1, 1670.8, 1621.7, 1557.0, 1536.1, 1486.8, 1444.4, 1385.3, 1313.6, 1302.0, 1286.3, 1238.7, 1196.5, 1117.8, 1071.4, 1016.6, 965.1, 912.5, 849.9, 830.5, 791.1, 763.7, 746.9, 727.1, 674.7, 620.8, 578.9, 557.7, 527.6, 508.4, 460.0, 436.8 cm$^{-1}$, and the main characteristic absorption peaks of the solid substance of crystalline form I of XLF-III-43 are the peaks at 3341.8, 3296.2, 2930.4, 1917.2, 1721.1, 1670.8, 1557.0, 1385.3, 1302.2, 1238.7, 1196.5, 912.5, 849.9, 791.1, 620.8, 436.8 cm$^{-1}$.

According to crystalline form I of XLF-III-43 of the invention, optimize almost sterling of crystalline form I of XLF-III-43 as medicine active component (nearly don't include any other crystalline form of XLF-III-43. However, the invention also includes crystalline form I of XLF-III-43 which mixed with one or several other crystalline forms of XLF-III-43. If medicine active component is the mixture of crystalline form I of XLF-III-43 and other crystalline forms of XLF-III-43, the component should be optimized to include 50% of crystalline form I of XLF-III-43 at least, then optimize to include 70% of crystalline form I of XLF-III-43 at least, then 80%, 90%, 95%, at last greatest optimize to include 98% of crystalline form I of XLF-III-43 at least.

The invention also includes one pharmaceutical composition which contains crystalline form I of XLF-III-43 and vehicle which is acceptable in pharmacodynamics.

The invention also provides the preparation method of crystalline form I of XLF-III-43:

(a) Take the sample of XLF-III-43 into single or mixed solvent and heat to dissolve completely, then in the environment of in temperature scope of 65° C. to 75° C., relative humidity of below 90%, recryst for 24 to 90 hours, then obtain the solid substance sample of crystalline form I.

(b) Separate the solid substance sample of crystalline form I of XLF-III-43 from the solution.

(c) Dry the solid substance until the surface solvent is removed.

Solvent system could be single or mixed solvents. For example, the solvents could be DMF or mixed solvents that can mix with DMF. The single solvents that could be mixed with DMF are selected from methanol, ethanol, 95% ethanol, ammonia water, hydrochloric acid, and water. The optimized solvents are DMF, ethanol, 95% ethanol and DMF is the best.

Mixed solvents are selected from combinations of methanol, ethanol, 95% ethanol, DMF, ammonia water, hydrochloric acid, and water (combinations of two kinds of single solvents or more) with different matching proportions. The optimized mixed solvent is the mixture of DMF and water.

Temperature scope is 65° C. to 75° C., optimizing 67° C. to 74° C., greatest optimizing 68° C. to 72° C.

The relative humidity scope is below 90%, optimizing below 70%, preferably optimizing below 50%, greatest optimizing below 40%.

The crystalling time is from 24 to 90 hours, optimizing 48 to 80 hours, greatest optimizing 72 hours.

The Morphological Characteristics of Crystalline Form II of XLF-III-43:

1. When taking X-ray single crystal diffraction to analyze the structure, the solid substance of crystalline form II of XLF-III-43 shows the symmetry of monoclinic system, the space group is P2$_1$, and the cell parameters are, a=7.205 Å, b=32.723 Å, c=8.081 Å, α=90°, β=87.77°, γ=90°.

Figure 7:
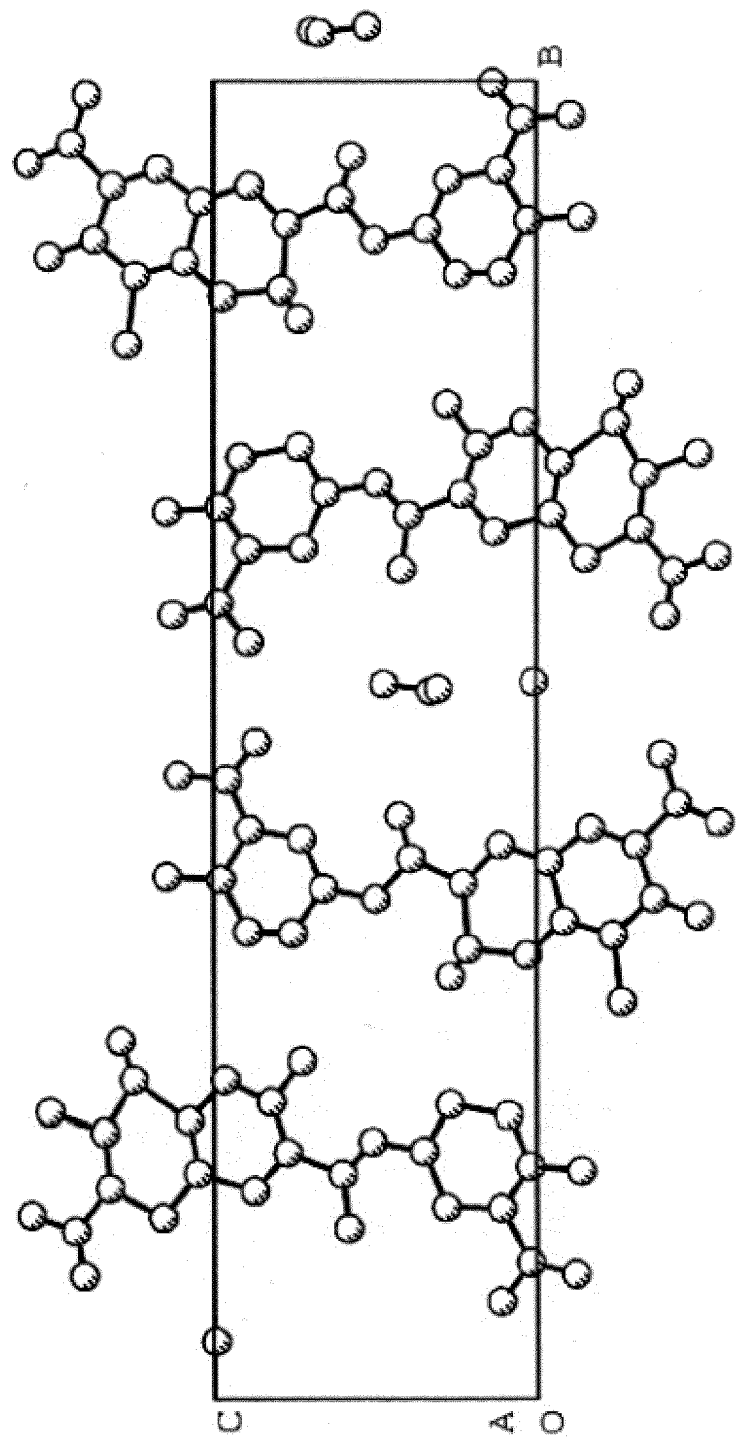

In the solid substance sample of crystalline form II, except the molecular of XLF-III-43, C$_{18}$H$_{12}$N$_2$O$_9$, the crystallized solvent molecular of dimethylamine and water also exists. In crystalline state, there are 2 molecular of XLF-III-43, 0.5 molecular of DMF and 0.5 molecular of crystallized water in one asymmetric unit. The proportion of the molecular of XLF-III-43, dimethylamine and crystallized water is 2.0:0.5:0.5. FIG. 7 shows the accumulation projection of the crystal unit of crystalline form II of XLF-III-43. Table 5 shows the non-hydrogen atomic coordinate parameters and the values of equivalent temperature factors of crystalline form II of XLF-III-43. Table 6 shows the bond length values of bonding atoms of crystalline form II of XLF-III-43. Table 7 shows bond angle values of bonding atoms of crystalline form II of XLF-III-43.

TABLE 5

Non-hydrogen atomic coordinate parameters of the sample of crystalline form II of XLF-III-43(relative coordinate)

| Atoms | x | y | z | Biso |
|---|---|---|---|---|
| O1 | .2478(20) | .2416(4) | .9643(16) | 3.9(7) |
| O2 | .3780(30) | .2559(6) | .7258(21) | 6.3(9) |
| O3 | −.0420(30) | .0950(5) | 1.4008(22) | 7.3(1) |
| O4 | −.0870(30) | .1409(6) | 1.5661(20) | 7.2(1) |
| O5 | −.0092(24) | .2183(5) | 1.5039(19) | 5.2(8) |

TABLE 5-continued

Non-hydrogen atomic coordinate parameters of the sample of crystalline form II of XLF-III-43 (relative coordinate)

| Atoms | x | y | z | Biso |
|---|---|---|---|---|
| O6 | .3760(30) | .1307 | .5816(18) | 5.8(9) |
| O7 | .5330(30) | .0755(5) | .1086(21) | 6.7(1) |
| O8 | .6720(30) | .0963(5) | −.1196(21) | 6.3(9) |
| O9 | .7530(20) | .1738(5) | −.1430(16) | 4.2(7) |
| N1 | −.0500(30) | .1275(6) | 1.4285(20) | 4.1(8) |
| N2 | .4710(30) | .1971(5) | .5073(21) | 4.0(8) |
| C1 | .3050(30) | .2247(6) | .8220(23) | 3.9(1) |
| C2 | .2980(30) | .1882(8) | .7715(23) | 4.9(1) |
| C3 | .2430(20) | .1591(7) | .8750(23) | 4.7(1) |
| C4 | .1700(30) | .1727(8) | 1.0515(24) | 4.9(1) |
| C5 | .0790(20) | .1400(8) | 1.1530(30) | 5.3(1) |
| C6 | .0450(20) | .1605(10) | 1.3230(27) | 6.0(1) |
| C7 | .0470(30) | .2029(8) | 1.3360(28) | 4.7(1) |
| C8 | .1140(40) | .2459(16) | 1.2530(24) | 9.5(2) |
| C9 | .1680(30) | .2118(8) | 1.0740(25) | 4.7(1) |
| C10 | .4040(40) | .1734(9) | .6030(32) | 5.5(1) |
| C11 | .1350(20) | .2733(8) | 1.2920(30) | 7.0(1) |
| C12 | .5430(30) | .1890(7) | .3484(25) | 3.9(9) |
| C13 | .5500(20) | .1458(7) | .2780(32) | 5.7(1) |
| C14 | .6080(30) | .1460(6) | .1010(30) | 3.6(9) |
| C15 | .6750(24) | .1791(8) | .0180(30) | 5.2(1) |
| C16 | .6740(30) | .2156(7) | .0869(24) | 4.1(1) |
| C17 | .6100(30) | .2243(10) | .2740(32) | 5.6(1) |
| C18 | .6280(24) | .1049(9) | .0250(30) | 6.3(1) |
| N1″ | .4860(20) | .5383(13) | .3320(27) | 4.2(1) |
| C1″ | .4080(26) | .5436(12) | .4770(24) | 3.5(1) |
| O1' | .7631(23) | .3379(5) | .0279(16) | 4.6(7) |
| O2' | .6073(23) | .3215(4) | .2638(18) | 4.9(7) |
| O3' | .9970(30) | .4901(6) | −.3987(23) | 7.4(1) |
| O4' | 1.0943(24) | .4377(6) | −.5695(20) | 5.7(9) |
| O5' | 1.0185(21) | .3669(4) | −.5061(17) | 3.9(6) |
| O6' | .6370(30) | .4429(5) | .4241(19) | 5.7(9) |
| O7' | .3950(25) | .4995(7) | .8690(23) | 9.8(1) |
| O8' | .3010(30) | .4741(6) | 1.1099(21) | 6.5(1) |
| O9' | .2502(19) | .3967(5) | 1.1412(19) | 4.4(7) |
| N1' | .9990(30) | .4529(8) | −.4411(22) | 5.8(1) |
| N2' | .5310(30) | .3802(5) | .4950(21) | 4.0(8) |
| C1' | .6780(30) | .3426(9) | .2070(23) | 5.3(1) |
| C2' | .6810(30) | .3930(6) | .2290(24) | 3.1(8) |
| C3' | .7690(30) | .4209(7) | .1130(23) | 4.4(1) |
| C4' | .8410(30) | .4094(6) | −.0332(24) | 3.2(8) |
| C5' | .8860(30) | .4341(6) | −.1677(23) | 3.2(8) |
| C6' | .9610(30) | .4215(7) | −.3127(24) | 4.0(1) |
| C7' | .9550(30) | .3800(6) | −.3644(22) | 3.1(8) |
| C8' | .8833(20) | .3517(5) | −.2386(21) | 1.7(7) |
| C9' | .8270(30) | .3648(8) | −.0880(23) | 4.7(1) |
| C10' | .6150(30) | .4112(6) | .3893(25) | 3.1(8) |
| C11' | .8800(40) | .3029(7) | −.2600(23) | 4.7(1) |
| C12' | .4570(30) | .3890(7) | .6600(24) | 4.2(1) |
| C13' | .4355(23) | .4253(6) | .7234(22) | 2.9(8) |
| C14' | .3580(30) | .4324(8) | .8910(25) | 4.4(1) |
| C15' | .3100(30) | .3947(7) | .9770(20) | 4.0(9) |
| C16' | .3310(30) | .3553(8) | .8980(23) | 4.9(1) |
| C17' | .4030(30) | .3540(7) | .7610(23) | 4.5(1) |
| C18' | .3710(20) | .4718(8) | .9630(26) | 6.8(1) |
| C2″ | .6270(20) | .5397(16) | .3010(25) | 6.0(5) |
| OW | .0120(20) | .0432(22) | .0050(24) | 9.6(9) |

TABLE 6

The bond length values of the sample of crystalline form II of XLF-III-43 (Å)

| Bonding atoms | Bond length |
|---|---|
| O(1)—C(1) | 1.33(4) |
| O(1)—C(9) | 1.43(4) |
| O(2)—C(1) | 1.37(4) |
| O(3)—N(1) | 1.13(4) |
| O(4)—N(1) | 1.19(3) |
| O(5)—C(7) | 1.50(4) |
| O(6)—C(10) | 1.37(4) |
| O(7)—C(18) | 1.36(5) |
| O(8)—C(18) | 1.22(4) |
| O(8)—Ho(8) | 1.15(7) |
| O(9)—C(15) | 1.42(4) |
| O(9)—Ho(9) | 1.05(7) |
| N(1)—C(6) | 1.52(5) |
| N(2)—C(10) | 1.21(4) |
| N(2)—C(12) | 1.39(4) |
| N(2)—Hn(2) | 1.17(8) |
| C(1)—C(2) | 1.29(5) |
| C(2)—C(3) | 1.32(5) |
| C(2)—C(10) | 1.59(5) |
| C(3)—C(4) | 1.56(4) |
| C(3)—H(3) | 1.11(9) |
| C(17')—H(17') | 1.08(9) |
| N(1″)—C(1″) | 1.25(6) |
| C(4)—C(5) | 1.53(5) |
| C(4)—C(9) | 1.30(6) |
| C(5)—C(6) | 1.54(5) |
| C(5)—H(5) | 1.06(9) |
| C(6)—C(7) | 1.37(5) |
| C(7)—C(8) | 1.53(5) |
| C(8)—C(9) | 1.76(5) |
| C(8)—C(11) | 1.02(5) |
| C(11)—H(11A) | 1.14(8) |
| C(11)—H(11B) | 1.19(8) |
| C(11)—H(11C) | 1.07(7) |
| C(12)—C(13) | 1.50(5) |
| C(12)—C(17) | 1.39(5) |
| C(13)—C(14) | 1.45(5) |
| C(13)—H(13) | 1.15(8) |
| C(14)—C(15) | 1.32(5) |
| C(14)—C(18) | 1.53(5) |
| C(15)—C(16) | 1.35(5) |
| C(16)—C(17) | 1.55(4) |
| C(16)—H(16) | 1.10(8) |
| C(17)—H(17) | 1.14(9) |
| N(1″)—C(2″) | 1.02(8) |
| C(1″)—H(1″C) | 1.08(5) |
| O(1')—C(1') | 1.56(4) |
| O(1')—C(9') | 1.33(4) |
| O(2')—C(1') | .97(4) |
| O(2')—Hn(2') | 1.67(7) |
| O(3')—N(1') | 1.28(4) |
| O(4')—N(1') | 1.30(4) |
| O(5')—C(7') | 1.27(4) |
| O(6')—C(10') | 1.11(4) |
| O(7')—C(18') | 1.19(5) |
| O(8')—C(18') | 1.30(4) |
| O(8')—Ho(8') | 1.09(7) |
| O(9')—C(15') | 1.39(4) |
| O(9')—Ho(9') | 1.17(7) |
| N(1')—C(6') | 1.50(4) |
| N(2')—C(10') | 1.46(4) |
| N(2')—C(12') | 1.42(4) |
| N(2')—Hn(2') | 1.16(8) |
| C(1')—C(2') | 1.63(5) |
| C(2')—C(3') | 1.47(4) |
| C(2')—C(10') | 1.53(4) |
| C(3')—C(4') | 1.35(4) |
| C(1″)—H(1″A) | 1.08(6) |
| C(3')—H(3') | 1.09(9) |
| C(4')—C(5') | 1.38(5) |
| C(4')—C(9') | 1.54(5) |
| C(5')—C(6') | 1.31(4) |
| C(5')—H(5') | 1.17(9) |
| C(6')—C(7') | 1.41(5) |
| C(7')—C(8') | 1.47(4) |
| C(8')—C(9') | 1.32(5) |
| C(8')—C(11') | 1.68(4) |
| C(11')—H(11'A) | 1.03(7) |
| C(11')—H(11'B) | 1.06(7) |
| C(11')—H(11'C) | 1.14(8) |

TABLE 6-continued

The bond length values of the sample of crystalline form II of XLF-III-43 (Å)

| Bonding atoms | Bond length |
|---|---|
| C(12')—C(13') | 1.35(5) |
| C(12')—C(17') | 1.42(5) |
| C(13')—C(14') | 1.42(4) |
| C(13')—H(13') | 1.11(8) |
| C(14')—C(15') | 1.47(5) |
| C(14')—C(18') | 1.37(6) |
| C(15')—C(16') | 1.47(5) |
| C(16')—C(17') | 1.20(5) |
| C(16')—H(16') | 1.12(8) |
| C(1")—H(1"B) | 1.08(6) |

TABLE 7

The bond angle values of the sample of crystalline form II of XLF-III-43 (°)

| Bonding atoms | Bond angle |
|---|---|
| C(1)—O(1)—C(9) | 110.7(24) |
| C(18)—O(8)—Ho(8) | 83.8(24) |
| C(15)—O(9)—Ho(9) | 88.5(21) |
| O(3)—N(1)—O(4) | 120.2(29) |
| O(3)—N(1)—C(6) | 125.1(27) |
| O(4)—N(1)—C(6) | 112.7(23) |
| C(10)—N(2)—C(12) | 127.1(30) |
| C(10)—N(2)—Hn(2) | 111.8(24) |
| C(12)—N(2)—Hn(2) | 118.3(18) |
| O(1)—C(1)—O(2) | 107.0(25) |
| O(1)—C(1)—C(2) | 131.1(32) |
| O(2)—C(1)—C(2) | 121.7(26) |
| C(1)—C(2)—C(3) | 119.5(29) |
| C(1)—C(2)—C(10) | 125.0(31) |
| C(3)—C(2)—C(10) | 114.2(27) |
| C(2)—C(3)—C(4) | 117.3(23) |
| C(2)—C(3)—H(3) | 124.7(24) |
| C(4)—C(3)—H(3) | 118.3(24) |
| C(3)—C(4)—C(5) | 115.7(23) |
| C(3)—C(4)—C(9) | 115.2(21) |
| C(5)—C(4)—C(9) | 128.9(23) |
| C(4)—C(5)—C(6) | 101.9(24) |
| C(4)—C(5)—H(5) | 124.0(25) |
| C(6)—C(5)—H(5) | 133.1(24) |
| N(1)—C(6)—C(5) | 102.9(30) |
| N(1)—C(6)—C(7) | 131.2(23) |
| C(5)—C(6)—C(7) | 123.4(27) |
| O(5)—C(7)—C(6) | 114.7(32) |
| O(5)—C(7)—C(8) | 102.8(29) |
| C(6)—C(7)—C(8) | 142.0(33) |
| C(7)—C(8)—C(9) | 87.8(23) |
| C(7)—C(8)—C(11) | 132.3(24) |
| C(9)—C(8)—C(11) | 138.1(24) |
| O(1)—C(9)—C(4) | 125.2(30) |
| O(1)—C(9)—C(8) | 100.9(31) |
| C(4)—C(9)—C(8) | 133.1(30) |
| O(6)—C(10)—N(2) | 128.4(23) |
| O(6)—C(10)—C(2) | 112.8(28) |
| N(2)—C(10)—C(2) | 118.9(26) |
| C(8)—C(11)—H(11A) | 129.2(25) |
| C(8)—C(11)—H(11B) | 124.0(26) |
| C(8)—C(11)—H(11C) | 106.8(26) |
| H(11A)—C(11)—H(11B) | 98.0(26) |
| H(11A)—C(11)—H(11C) | 95.9(26) |
| H(11B)—C(11)—H(11C) | 93.8(25) |
| N(2)—C(12)—C(13) | 120.2(23) |
| N(2)—C(12)—C(17) | 114.9(27) |
| C(13)—C(12)—C(14) | 125.2(23) |
| C(12)—C(13)—C(14) | 112.8(27) |
| C(12)—C(13)—H(13) | 125.0(24) |
| C(14)—C(13)—H(13) | 121.2(25) |
| C(13)—C(14)—C(15) | 125.4(21) |
| C(13)—C(14)—C(18) | 118.2(23) |

TABLE 7-continued

The bond angle values of the sample of crystalline form II of XLF-III-43 (°)

| Bonding atoms | Bond angle |
|---|---|
| C(15)—C(14)—C(18) | 116.1(28) |
| O(9)—C(15)—C(14) | 122.0(27) |
| O(9)—C(15)—C(16) | 115.7(30) |
| C(14)—C(15)—C(16) | 121.9(30) |
| C(15)—C(16)—C(17) | 121.2(30) |
| C(15)—C(16)—H(16) | 122.0(25) |
| C(17)—C(16)—H(16) | 116.9(25) |
| C(12)—C(17)—C(16) | 113.7(23) |
| C(12)—C(17)—H(17) | 121.0(24) |
| C(16)—C(17)—H(17) | 124.2(28) |
| O(7)—C(18)—O(8) | 116.3(29) |
| O(7)—C(18)—C(14) | 111.9(31) |
| O(8)—C(18)—C(14) | 131.1(30) |
| C(1')—O(1')—C(9') | 134.0(23) |
| C(18')—O(8')—Ho(8') | 87.7(25) |
| C(15')—O(9')—Ho(9') | 85.8(28) |
| O(3')—N(1')—O(4') | 126.2(23) |
| O(3')—N(1')—C(6') | 116.9(23) |
| O(4')—N(1')—C(6') | 112.8(30) |
| C(10')—N(2')—C(12') | 123.5(23) |
| C(10')—N(2')—Hn(2') | 107.9(24) |
| C(12')—N(2')—Hn(2') | 128.3(24) |
| O(1')—C(1')—O(2') | 122.0(30) |
| O(1')—C(1')—C(2') | 100.0(25) |
| O(2')—C(1')—C(2') | 132.1(30) |
| C(1')—C(2')—C(3') | 126.6(25) |
| C(1')—C(2')—C(10') | 118.3(24) |
| C(3')—C(2')—C(10') | 114.9(30) |
| C(2')—C(3')—C(4') | 120.0(30) |
| C(2')—C(3')—H(3') | 117.3(24) |
| C(4')—C(3')—H(3') | 121.9(24) |
| C(3')—C(4')—C(5') | 125.2(23) |
| C(3')—C(4')—C(9') | 119.2(27) |
| C(5')—C(4')—C(9') | 113.1(28) |
| C(4')—C(5')—C(6') | 124.8(26) |
| C(4')—C(5')—H(5') | 117.7(24) |
| C(6')—C(5')—H(5') | 117.3(24) |
| N(1')—C(6')—C(5') | 116.9(23) |
| N(1')—C(6')—C(7') | 116.6(24) |
| C(5')—C(6')—C(7') | 125.9(23) |
| O(5')—C(7')—C(6') | 126.0(26) |
| O(5')—C(7')—C(8') | 122.4(26) |
| C(6')—C(7')—C(8') | 111.8(25) |
| C(7')—C(8')—C(9') | 126.0(31) |
| C(7')—C(8')—C(11') | 121.3(24) |
| C(9')—C(8')—C(11') | 111.8(30) |
| O(1')—C(9')—C(4') | 116.2(30) |
| O(1')—C(9')—C(8') | 125.0(27) |
| C(4')—C(9')—C(8') | 117.2(32) |
| O(6')—C(10')—N(2') | 125.5(23) |
| O(6')—C(10')—C(2') | 123.7(24) |
| N(2')—C(10')—C(2') | 110.8(29) |
| C(8')—C(11')—H(11'A) | 108.5(24) |
| C(8')—C(11')—H(11'B) | 106.9(25) |
| C(8')—C(11')—H(11'C) | 101.8(27) |
| H(11'A)—C(11')—H(11'B) | 115.7(26) |
| H(11'A)—C(11')—H(11'C) | 112.9(29) |
| H(11'B)—C(11')—H(11'C) | 110.2(26) |
| N(2')—C(12')—C(13') | 124.0(23) |
| N(2')—C(12')—C(17') | 116.3(27) |
| C(13')—C(12')—C(17') | 118.7(26) |
| C(12')—C(13')—C(14') | 123.4(24) |
| C(12')—C(13')—H(13') | 118.1(25) |
| C(14')—C(13')—H(13') | 118.7(25) |
| C(13')—C(14')—C(15') | 112.3(23) |
| C(13')—C(14')—C(18') | 120.5(28) |
| C(15')—C(14')—C(18') | 126.2(25) |
| O(9')—C(15')—C(14') | 118.3(26) |
| O(9')—C(15')—C(16') | 120.4(27) |
| C(14')—C(15')—C(16') | 121.2(29) |
| C(15')—C(16')—C(17') | 118.8(23) |
| C(15')—C(16')—H(16') | 118.5(25) |
| C(17')—C(16')—H(16') | 122.0(25) |
| C(12')—C(17')—C(16') | 125.4(24) |
| C(12')—C(17')—H(17') | 116.9(26) |

TABLE 7-continued

The bond angle values of the sample of crystalline form II of XLF-III-43
(°)

| Bonding atoms | Bond angle |
|---|---|
| C(16')—C(17')—H(17') | 117.9(25) |
| O(7')—C(18')—O(8') | 124.3(30) |
| O(7')—C(18')—C(14') | 118.9(30) |
| O(8')—C(18')—C(14') | 115.2(30) |
| C(1")—N(1")—C(2") | 118.5(26) |
| N(1")—C(1")—H(1"C) | 109.3(25) |
| N(1")—C(1")—H(1"A) | 109.9(25) |
| N(1")—C(1")—H(1"B) | 109.4(26) |
| H(1"C)—C(1")—H(1"A) | 109.7(25) |
| H(1"C)—C(1")—H(1"B) | 109.8(25) |
| H(1"A)—C(1")—H(1"B) | 109.6(24) |

2. When taking X-ray powder diffraction analysis (CuK$_\alpha$ irradiation), the solid substance of crystalline form II of XLF-III-43 shows diffraction peak position: 2-Theta values (°) or d values (Å), and relative intensity of diffraction peak: values of peak height (Height %). Below is the characteristic peak values of solid substances in crystalline state (Table 4, FIG. 4).

TABLE 8

The characteristic peak values of X-ray powder diffraction of the sample of crystalline form II of XLF-III-43

| Peak | 2-Theta | d(Å) | Height % |
|---|---|---|---|
| 1 | 16.3615 | 5.40 | 9 |
| 2 | 8.1807 | 10.81 | 100 |
| 3 | 7.8397 | 11.29 | 5 |
| 4 | 7.1995 | 12.29 | 3 |
| 5 | 6.4900 | 13.64 | 6 |
| 6 | 6.0087 | 14.74 | 20 |
| 7 | 5.4807 | 16.17 | 32 |
| 8 | 5.0844 | 17.44 | 4 |
| 9 | 4.8428 | 18.32 | 6 |
| 10 | 4.3473 | 20.43 | 4 |
| 11 | 4.1060 | 21.64 | 5 |
| 12 | 4.0374 | 22.01 | 2 |
| 13 | 3.9199 | 22.68 | 6 |
| 14 | 3.8659 | 23.00 | 2 |
| 15 | 3.7908 | 23.47 | 8 |
| 16 | 3.5782 | 24.88 | 11 |
| 17 | 3.5157 | 25.33 | 4 |
| 18 | 3.4452 | 25.86 | 9 |
| 19 | 3.3153 | 26.89 | 3 |
| 20 | 3.2781 | 27.20 | 6 |
| 21 | 3.2413 | 27.52 | 91 |
| 22 | 3.1795 | 28.06 | 7 |
| 23 | 3.1070 | 28.73 | 8 |
| 24 | 3.0134 | 29.64 | 17 |
| 25 | 2.9046 | 30.78 | 6 |
| 26 | 2.7804 | 32.19 | 3 |
| 27 | 2.7018 | 33.16 | 2 |
| 28 | 2.5836 | 34.72 | 4 |
| 29 | 2.3789 | 37.82 | 3 |
| 30 | 2.3362 | 38.53 | 2 |
| 31 | 2.2874 | 39.39 | 2 |
| 32 | 2.1538 | 41.95 | 3 |
| 33 | 2.1219 | 42.61 | 2 |

3. In the DSC spectrum of the solid substance of crystalline form II of XLF-III-43 (FIG. 9), there are two peaks of heat emission with the transition values at about 307° C. and 345° C.

4. In the infrared absorption spectrum of the solid substance of crystalline form II of XLF-III-43 (FIG. 10), there are absorption peaks at 3299.0, 3138.1, 3068.8, 2786.8, 2448.4, 1911.8, 1720.0, 1662.8, 1621.6, 1547.9, 1486.1, 1471.4, 1442.0, 1376.1, 1351.7, 1312.4, 1286.3, 1240.5, 1193.4, 1147.4, 1117.4, 1070.7, 1018.8, 965.3, 954.1, 914.9, 850.5, 836.1, 790.2, 762.5, 747.0, 726.1, 716.4, 680.2, 621.7, 580.1, 564.0, 527.0, 508.5, 458.5 cm$^{-1}$ and the main characteristic absorption peaks of the solid substance of crystalline form II of XLF-III-43 are the peaks at 3299.0, 3138.1, 3068.8, 2786.8, 2448.4, 1911.8, 1720.0, 1662.8, 1547.9, 1376.1, 1351.7, 1240.5, 1193.4, 954.1, 914.9, 836.1, 716.4, 680.2, 564.0, 458.5 cm$^{-1}$.

According to crystalline form II of XLF-III-43 of the invention, optimize almost sterling of crystalline form II of XLF-III-43 as medicine active component (nearly don't include any other crystalline form of XLF-III-43. However, the invention also includes crystalline form II of XLF-III-43 which mixed with one or several other crystalline forms of XLF-III-43. If medicine active component is the mixture of crystalline form II of XLF-III-43 and other crystalline forms of XLF-III-43, the component should be optimized to include 50% of crystalline form II of XLF-III-43 at least, then optimize to include 70% of crystalline form II of XLF-III-43 at least, then 80%, 90%, 95%, at last greatest optimize to include 98% of crystalline form II of XLF-III-43 at least.

The invention also includes one pharmaceutical composition which contains crystalline form II of XLF-III-43 and vehicle which is acceptable in pharmacodynamics.

The invention also provides the preparation method of crystalline form II of XLF-III-43:

(a) Take the sample of XLF-III-43 into single or mixed solvent and heat to dissolve completely, then in the environment of in temperature scope of 75° C. to 85° C., relative humidity of below 90%, recryst completely and obtain the solid substance sample of crystalline form II.

(b) Separate the solid substance sample of crystalline form II of XLF-III-43 from the solution.

(c) Dry the solid substance until the surface solvent is removed.

Solvent system could be single or mixed solvents. For example, the solvents could be DMF or mixed solvents that can mixed with DMF. The single solvents that could be mixed with DMF are selected from methanol, ethanol, 95% ethanol, ammonia water, hydrochloric acid, and water. The optimized solvents are DMF, ethanol, 95% ethanol and DMF is the best.

Mixed solvents are selected from combinations of methanol, ethanol, 95% ethanol, DMF, ammonia water, hydrochloric acid, and water (combinations of two kinds of single solvents or more) with different matching proportions. The optimized mixed solvent is the mixture of DMF and water.

Temperature scope is 75° C. to 85° C., optimizing 77° C. to 84° C., greatest optimizing 78° C. to 82° C.

The relative humidity scope is below 90%, optimizing below 70%, preferably optimizing below 50%, greatest optimizing below 40%.

The crystalling time is from 24 to 120 hours, optimizing 36 to 96 hours, greatest optimizing 48 hours.

The Morphological Characteristics of Crystalline Form III of XLF-III-43:

1. When taking X-ray single crystal diffraction to analyze the structure, the solid substance of crystalline form III of XLF-III-43 obtained from the invention shows the symmetry of triclinic system, the space group is P1, and the cell parameters are, a=7.923 Å, b=10.313 Å, c=12.983 Å, α=90.43°, β=91.73°, γ=72.74°.

Figure 11:
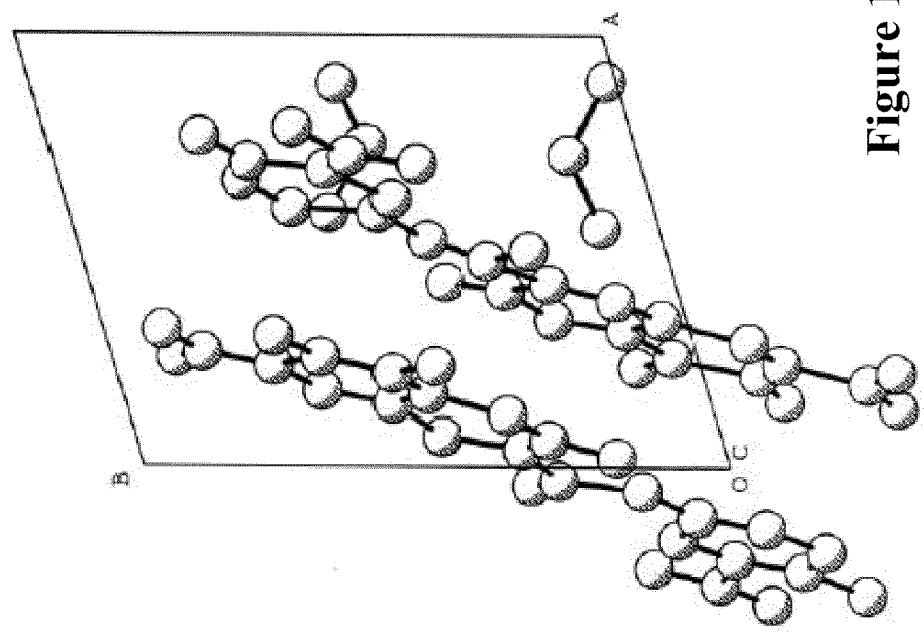

In solid substance sample of crystalline form III, except the molecular of XLF-III-43, $C_{18}H_{12}N_2O_9$, the crystallized solvent molecular of dimethylamine also exists. In crystalline state, the proportion of the molecular of XLF-III-43 and dimethylamine is 2:2. FIG. 11 shows the accumulation projection of the crystal unit of crystalline form III of XLF-III-43. Table 9 shows the non-hydrogen atomic coordinate parameters and the values of equivalent temperature factors of crystalline form III of XLF-III-43. Table 10 shows the bond length values of bonding atoms of crystalline form III of XLF-III-43. Table 11 shows bond angle values of bonding atoms of crystalline form III of XLF-III-43.

TABLE 9

Non-hydrogen atomic coordinate parameters of the sample of crystalline form III of XLF-III-43 (relative coordinate)

| Atoms | x | y | z | Biso |
|---|---|---|---|---|
| O1 | .1198 | .3529 | .6637 | 5.6(6) |
| O2 | .0220(19) | .1886(12) | .6020(8) | 7.7(8) |
| O3 | .2490(17) | .8899(12) | .5360(10) | 7.2(7) |
| O4 | .3149(19) | .9002(13) | .7013(10) | 8.8(8) |
| O5 | .2998(18) | .7096(13) | .8192(9) | 8.2(8) |
| O6 | −.0426(17) | .3476(12) | .3103(7) | 6.1(6) |
| O7 | −.2328(17) | .1811(12) | .0173(8) | 7.2(7) |
| O8 | −.3148(17) | −.0020(11) | .0003(8) | 6.7(7) |
| O9 | −.2911(17) | −.1680(11) | .1388(9) | 7.0(7) |
| N1 | .2628(18) | .8416(13) | .6246(8) | 5.5(7) |
| N2 | −.0542(19) | .1618(13) | .4048(9) | 5.8(8) |
| C1 | .0625(19) | .2954(14) | .5846(11) | 4.4(7) |
| C2 | .0403(20) | .3440(15) | .4914(12) | 4.6(8) |
| C3 | .0696(20) | .4766(15) | .4715(12) | 4.8(8) |
| C4 | .1471(18) | .5428(17) | .5596(12) | 4.7(8) |
| C5 | .1747(23) | .6529(15) | .5475(13) | 5.7(9) |
| C6 | .2320(21) | .7238(15) | .6339(11) | 4.7(8) |
| C7 | .2525(20) | .6389(19) | .7281(12) | 5.9(9) |
| C8 | .2164(22) | .5289(16) | .7391(9) | 5.4(9) |
| C9 | .1683(20) | .4804(14) | .6558(12) | 4.3(7) |
| C10 | −.0315(17) | .2984(11) | .3905(10) | 2.7(6) |
| C11 | .2320(30) | .4542(20) | .8495(13) | 8.2(9) |
| C12 | −.1137(20) | .0811(15) | .3449(10) | 4.3(7) |
| C13 | −.1655(21) | .1259(15) | .2319(12) | 5.0(8) |
| C14 | −.2116(22) | .0381(17) | .1746(11) | 5.4(8) |
| C15 | −.2364(18) | −.0737(14) | .2114(12) | 4.2(7) |
| C16 | −.1908(23) | −.1204(17) | .3052(11) | 6.5(9) |
| C17 | −.1386(23) | −.0308(14) | .3731(12) | 5.5(9) |
| C18 | −.2710(30) | .0769(19) | .0526(14) | 6.8(9) |
| N1D | .7508(20) | .4561(14) | .0202(10) | 6.3(8) |
| C1D | .8880(30) | .4749(20) | .0619(10) | 8.6(9) |
| C2D | .5900(30) | .5517(23) | .0473(16) | 8.9(9) |
| O1' | .3400(15) | .2260(11) | .1548(8) | 6.0(6) |
| O2' | .4279(16) | .3928(10) | .2090(8) | 5.9(6) |
| O3' | .2290(18) | −.3322(11) | .2871(9) | 7.6(8) |
| O4' | .1434(17) | −.3171(12) | .1305(10) | 7.4(7) |
| O5' | .1569(16) | −.1273(11) | .0094(8) | 6.8(6) |
| O6' | .5005(18) | .2335(13) | .5126(10) | 8.7(8) |
| O7' | .7036(17) | .3819(11) | .7980(8) | 6.8(7) |
| O8' | .7862(17) | .5718(12) | .8290(9) | 7.4(7) |
| O9' | .7635(17) | .7379(12) | .6826(9) | 6.9(7) |
| N1' | .2005(21) | −.2781(15) | .2107(12) | 7.2(8) |
| N2' | .5260(17) | .4031(13) | .4103(9) | 5.3(7) |
| C1' | .4072(23) | .2952(16) | .2285(12) | 5.4(9) |
| C2' | .4224(20) | .2158(16) | .3423(10) | 4.6(8) |
| C3' | .3814(23) | .1117(15) | .3484(11) | 5.1(9) |
| C4' | .3407(19) | .0423(15) | .2709(11) | 4.5(8) |
| C5' | .2949(23) | −.0963(17) | .2762(11) | 5.8(9) |
| C6' | .2444(22) | −.1404(15) | .1910(13) | 5.3(8) |
| C7' | .2167(22) | −.0965(15) | .0895(14) | 5.7(9) |
| C8' | .2532(24) | .0429(18) | .0760(13) | 6.6(9) |
| C9' | .3147(21) | .1112(19) | .1664(12) | 5.8(9) |
| C10' | .4779(22) | .3113(20) | .4233(13) | 6.1(9) |
| C11' | .2310(30) | .1074(17) | −.0233(12) | 6.0(9) |
| C12' | .5894(21) | .4716(14) | .5005(12) | 4.8(8) |
| C13' | .6203(19) | .4430(16) | .5903(10) | 4.5(8) |
| C14' | .6911(20) | .5353(15) | .6644(11) | 4.7(8) |
| C15' | .7073(22) | .6660(15) | .6292(12) | 5.1(8) |
| C16' | .6634(21) | .6880(16) | .5114(11) | 5.2(8) |
| C17' | .6002(20) | .6131(16) | .4547(12) | 4.8(8) |
| C18' | .7207(22) | .4909(16) | .7671(12) | 5.2(8) |
| N1D' | .7248(22) | .1173(15) | .8003(11) | 7.4(9) |
| C1D' | .5550(30) | .1005(22) | .7357(14) | 8.7(9) |
| C2D' | .8920(30) | .0186(20) | .7759(13) | 8.8(9) |

TABLE 10

The bond length values of the sample of crystalline form III of XLF-III-43 (Å)

| Bonding atoms | Bond length |
|---|---|
| O(1)—C(1) | 1.258(15) |
| O(1)—C(9) | 1.366(13) |
| O(2)—C(1) | 1.163(16) |
| O(2)—Hn(2) | 1.575(21) |
| O(3)—N(1) | 1.260(17) |
| O(4)—N(1) | 1.226(16) |
| O(5)—C(7) | 1.416(18) |
| O(5)—Ho(5) | .881(19) |
| O(6)—C(10) | 1.167(15) |
| O(7)—C(18) | 1.209(21) |
| O(7)—Ho(7) | 1.150(30) |
| O(8)—C(18) | 1.117(22) |
| O(9)—C(15) | 1.408(17) |
| N(1)—C(6) | 1.254(19) |
| N(2)—C(10) | 1.433(16) |
| N(2)—C(12) | 1.214(18) |
| N(2)—Hn(2) | 1.107(21) |
| C(1)—C(2) | 1.336(20) |
| C(2)—C(3) | 1.409(20) |
| C(2)—C(10) | 1.472(18) |
| C(3)—C(4) | 1.445(20) |
| C(3)—H(3) | 1.086(25) |
| C(4)—C(5) | 1.168(21) |
| C(4)—C(9) | 1.420(22) |
| C(5)—C(6) | 1.401(20) |
| C(5)—H(5) | 1.070(30) |
| C(6)—C(7) | 1.510(23) |
| C(7)—C(8) | 1.190(24) |
| C(8)—C(9) | 1.242(21) |
| C(8)—C(11) | 1.631(24) |
| C(11)—H(11A) | 1.100(30) |
| C(11)—H(11B) | 1.122(24) |
| C(11)—H(11C) | 1.070(30) |
| C(12)—C(13) | 1.583(19) |
| C(12)—C(17) | 1.231(20) |
| C(13)—C(14) | 1.208(21) |
| C(13)—H(13) | 1.125(24) |
| C(14)—C(15) | 1.277(22) |
| C(14)—C(18) | 1.684(24) |
| C(15)—C(16) | 1.355(23) |
| C(16)—C(17) | 1.334(23) |
| C(16)—H(16) | 1.150(30) |
| C(17)—H(17) | 1.040(24) |
| O(1')—C(1') | 1.294(17) |
| O(1')—C(9') | 1.229(21) |
| O(2')—C(1') | 1.065(19) |
| O(3')—N(1') | 1.163(20) |
| O(4')—N(1') | 1.193(19) |
| O(5')—C(7') | 1.182(19) |
| O(6')—C(10') | 1.411(22) |
| O(7')—C(18') | 1.207(18) |
| O(7')—Ho(7') | .990(30) |
| O(8')—C(18') | 1.247(18) |
| O(8')—Ho(9') | 1.562(22) |
| O(9')—C(15') | 1.107(17) |
| O(9')—Ho(9') | 1.090(23) |
| N(1')—C(6') | 1.484(20) |
| N(2')—C(10') | 1.044(22) |
| N(2')—C(12') | 1.448(18) |
| N(2')—Hn(2') | .956(19) |
| C(1')—C(2') | 1.683(21) |
| C(2')—C(3') | 1.122(21) |
| C(2')—C(10') | 1.495(23) |
| C(3')—C(4') | 1.274(21) |
| C(3')—H(3') | 1.068(22) |
| C(4')—C(5') | 1.471(22) |
| C(4')—C(9') | 1.533(22) |
| C(5')—C(6') | 1.246(23) |
| C(5')—H(5') | 1.097(25) |
| C(6')—C(7') | 1.399(25) |
| C(7')—C(8') | 1.480(23) |
| C(8')—C(9') | 1.439(23) |
| C(8')—C(11') | 1.468(24) |
| C(11')—H(11'A) | 1.080(30) |

TABLE 10-continued

The bond length values of the sample of crystalline form III of XLF-III-43 (Å)

| Bonding atoms | Bond length |
|---|---|
| C(11')—H(11'B) | 1.087(23) |
| C(11')—H(11'C) | 1.140(30) |
| C(12')—C(13') | 1.222(21) |
| C(12')—C(17') | 1.587(22) |
| C(13')—C(14') | 1.446(19) |
| C(13')—H(13') | 1.128(23) |
| C(14')—C(15') | 1.425(21) |
| C(14')—C(18') | 1.432(21) |
| C(15')—C(16') | 1.567(21) |
| C(16')—C(17') | 1.164(21) |
| C(16')—H(16') | 1.144(23) |
| C(17')—H(17') | 1.073(24) |
| N(1D)—C(1D) | 1.220(30) |
| N(1D)—C(2D) | 1.650(30) |
| N(1D)—Hn(1D) | 1.059(22) |
| C(1D)—Hc(1DA) | 1.118(23) |
| C(1D)—Hc(1DB) | 1.130(30) |
| C(1D)—Hc(1DC) | 1.040(30) |
| C(2D)—Hc(2DA) | 1.180(30) |
| C(2D)—Hc(2DB) | 1.050(30) |
| C(2D)—Hc(2DC) | 1.070(30) |
| N(1D')—C(1D') | 1.571(24) |
| N(1D')—C(2D') | 1.740(30) |
| N(1D')—Hn(1D') | .996(22) |
| C(1D')—Hc(1D'A) | 1.090(25) |
| C(1D')—Hc(1D'B) | 1.100(24) |
| C(1D')—Hc(1D'C) | 1.120(30) |
| C(2D')—Hc(2D'A) | 1.030(30) |
| C(2D')—Hc(2D'B) | 1.099(21) |
| C(2D')—Hc(2D'C) | 1.108(24) |

TABLE 11

The bond angle values of the sample of crystalline form III of XLF-III-43 (°)

| Bonding atoms | Bond angle |
|---|---|
| C(1)—O(1)—C(9) | 124.7(9) |
| C(7)—O(5)—Ho(5) | 115.0(16) |
| C(18)—O(7)—Ho(7) | 127.9(20) |
| C(15)—O(9)—Ho(9) | 103.8(13) |
| O(3)—N(1)—O(4) | 127.1(9) |
| O(3)—N(1)—C(6) | 109.6(10) |
| O(4)—N(1)—C(6) | 123.2(9) |
| C(10)—N(2)—C(12) | 125.3(9) |
| C(10)—N(2)—Hn(2) | 116.7(15) |
| C(12)—N(2)—Hn(2) | 118.0(13) |
| O(1)—C(1)—O(2) | 114.9(11) |
| O(1)—C(1)—C(2) | 126.8(10) |
| O(2)—C(1)—C(2) | 117.9(12) |
| C(1)—C(2)—C(3) | 110.1(11) |
| C(1)—C(2)—C(10) | 131.7(10) |
| C(3)—C(2)—C(10) | 118.0(9) |
| C(2)—C(3)—C(4) | 122.3(9) |
| C(2)—C(3)—H(3) | 120.6(15) |
| C(4)—C(3)—H(3) | 117.0(14) |
| C(3)—C(4)—C(5) | 124.7(10) |
| C(3)—C(4)—C(9) | 125.7(9) |
| C(5)—C(4)—C(9) | 109.6(11) |
| C(4)—C(5)—C(6) | 120.9(10) |
| C(4)—C(5)—H(5) | 121.9(16) |
| C(6)—C(5)—H(5) | 117.2(14) |
| N(1)—C(6)—C(5) | 121.0(9) |
| N(1)—C(6)—C(7) | 109.7(10) |
| C(5)—C(6)—C(7) | 129.1(9) |
| O(5)—C(7)—C(6) | 130.3(10) |
| O(5)—C(7)—C(8) | 119.2(10) |
| C(6)—C(7)—C(8) | 110.5(11) |
| C(7)—C(8)—C(9) | 120.1(10) |
| C(7)—C(8)—C(11) | 112.8(11) |

TABLE 11-continued

The bond angle values of the sample of crystalline form III of XLF-III-43 (°)

| Bonding atoms | Bond angle |
|---|---|
| C(9)—C(8)—C(11) | 127.1(10) |
| O(1)—C(9)—C(4) | 110.0(10) |
| O(1)—C(9)—C(8) | 120.1(9) |
| C(4)—C(9)—C(8) | 129.8(9) |
| O(6)—C(10)—N(2) | 112.3(11) |
| O(6)—C(10)—C(2) | 130.7(9) |
| N(2)—C(10)—C(2) | 116.0(9) |
| C(8)—C(11)—H(11A) | 112.2(14) |
| C(8)—C(11)—H(11B) | 111.8(13) |
| C(8)—C(11)—H(11C) | 103.4(15) |
| H(11A)—C(11)—H(11B) | 108.3(20) |
| H(11A)—C(11)—H(11C) | 109.6(18) |
| H(11B)—C(11)—H(11C) | 111.5(19) |
| N(2)—C(12)—C(13) | 136.6(9) |
| N(2)—C(12)—C(17) | 115.2(10) |
| C(13)—C(12)—C(17) | 108.1(10) |
| C(12)—C(13)—C(14) | 128.3(8) |
| C(12)—C(13)—H(13) | 117.7(16) |
| C(14)—C(13)—H(13) | 114.1(15) |
| C(13)—C(14)—C(15) | 122.6(10) |
| C(13)—C(14)—C(18) | 127.3(8) |
| C(15)—C(14)—C(18) | 110.1(10) |
| O(9)—C(15)—C(14) | 123.2(10) |
| O(9)—C(15)—C(16) | 129.1(8) |
| C(14)—C(15)—C(16) | 107.5(10) |
| C(15)—C(16)—C(17) | 133.4(9) |
| C(15)—C(16)—H(16) | 113.0(16) |
| C(17)—C(16)—H(16) | 113.6(16) |
| C(12)—C(17)—C(16) | 120.0(11) |
| C(12)—C(17)—H(17) | 118.4(16) |
| C(16)—C(17)—H(17) | 121.6(15) |
| O(7)—C(18)—O(8) | 127.2(10) |
| O(7)—C(18)—C(14) | 103.8(10) |
| O(8)—C(18)—C(14) | 128.5(9) |
| C(1')—O(1')—C(9') | 130.6(8) |
| C(7')—O(5')—Ho(5') | 113.3(13) |
| C(18')—O(7')—Ho(7') | 113.1(15) |
| C(15')—O(9')—Ho(9') | 121.9(14) |
| O(3')—N(1')—O(4') | 125.2(9) |
| O(3')—N(1')—C(6') | 108.7(10) |
| O(4')—N(1')—C(6') | 125.3(10) |
| C(10')—N(2')—C(12') | 130.7(9) |
| C(10')—N(2')—Hn(2') | 115.0(15) |
| C(12')—N(2')—Hn(2') | 114.2(14) |
| O(1')—C(1')—O(2') | 121.1(10) |
| O(1')—C(1')—C(2') | 123.2(9) |
| O(2')—C(1')—C(2') | 114.7(12) |
| C(1')—C(2')—C(3') | 113.0(11) |
| C(1')—C(2')—C(10') | 129.6(9) |
| C(3')—C(2')—C(10') | 117.4(9) |
| C(2')—C(3')—C(4') | 121.0(10) |
| C(2')—C(3')—H(3') | 120.8(16) |
| C(4')—C(3')—H(3') | 118.2(15) |
| C(3')—C(4')—C(5') | 128.1(10) |
| C(3')—C(4')—C(9') | 124.2(9) |
| C(5')—C(4')—C(9') | 107.5(10) |
| C(4')—C(5')—C(6') | 126.3(10) |
| C(4')—C(5')—H(5') | 117.7(16) |
| C(6')—C(5')—H(5') | 115.9(15) |
| N(1')—C(6')—C(5') | 124.9(10) |
| N(1')—C(6')—C(7') | 107.6(10) |
| C(5')—C(6')—C(7') | 127.4(9) |
| O(5')—C(7')—C(6') | 132.4(10) |
| O(5')—C(7')—C(8') | 118.2(11) |
| C(6')—C(7')—C(8') | 109.2(11) |
| C(7')—C(8')—C(9') | 123.6(10) |
| C(7')—C(8')—C(11') | 115.9(11) |
| C(9')—C(8')—C(11') | 120.1(9) |
| O(1')—C(9')—C(4') | 106.9(10) |
| O(1')—C(9')—C(8') | 127.5(9) |
| C(4')—C(9')—C(8') | 125.5(9) |
| O(6')—C(10')—N(2') | 114.0(11) |
| O(6')—C(10')—C(2') | 128.4(9) |
| N(2')—C(10')—C(2') | 117.6(9) |
| C(8')—C(11')—H(11'A) | 109.2(14) |

TABLE 11-continued

The bond angle values of the sample of crystalline form III of XLF-III-43 (°)

| Bonding atoms | Bond angle |
|---|---|
| C(8')—C(11')—H(11'B) | 106.7(14) |
| C(8')—C(11')—H(11'C) | 106.6(13) |
| H(11'A)—C(11')—H(11'B) | 106.0(18) |
| H(11'A)—C(11')—H(11'C) | 114.3(20) |
| H(11'B)—C(11')—H(11'C) | 113.8(20) |
| N(2')—C(12')—C(13') | 129.3(8) |
| N(2')—C(12')—C(17') | 120.5(11) |
| C(13')—C(12')—C(17') | 109.9(11) |
| C(12')—C(13')—C(14') | 126.5(9) |
| C(12')—C(13')—H(13') | 117.2(17) |
| C(14')—C(13')—H(13') | 116.1(16) |
| C(13')—C(14')—C(15') | 122.1(11) |
| C(13')—C(14')—C(18') | 127.2(10) |
| C(15')—C(14')—C(18') | 110.4(11) |
| O(9')—C(15')—C(14') | 123.6(12) |
| O(9')—C(15')—C(16') | 127.3(10) |
| C(14')—C(15')—C(16') | 109.1(12) |
| C(15')—C(16')—C(17') | 126.4(10) |
| C(15')—C(16')—H(16') | 115.9(16) |
| C(17')—C(16')—H(16') | 117.6(16) |
| C(12')—C(17')—C(16') | 125.8(12) |
| C(12')—C(17')—H(17') | 119.2(18) |
| C(16')—C(17')—H(17') | 114.8(15) |
| O(7')—C(18')—O(8') | 123.2(12) |
| O(7')—C(18')—C(14') | 106.1(11) |
| O(8')—C(18')—C(14') | 128.8(10) |
| C(1")—O(1")—C(9") | 124.1(8) |
| C(7")—O(5")—Ho(5") | 112.3(15) |
| C(18')—O(7')—Ho(7') | 77.4(14) |
| C(15")—O(9")—Ho(9") | 83.1(16) |
| O(3")—N(1")—O(4") | 127.1(10) |
| O(3")—N(1")—C(6") | 109.0(11) |
| O(4")—N(1")—C(6") | 122.9(10) |
| C(10")—N(2")—C(12") | 128.2(10) |
| C(10")—N(2")—Hn(2") | 114.3(15) |
| C(12")—N(2")—Hn(2") | 117.4(14) |
| O(1")—C(1")—O(2") | 114.7(10) |
| O(1")—C(1")—C(2") | 121.3(9) |
| O(2")—C(1")—C(2") | 123.2(11) |
| C(1")—C(2")—C(3") | 108.7(10) |
| C(1")—C(2")—C(10") | 123.6(9) |
| C(3")—C(2")—C(10") | 127.7(9) |
| C(2")—C(3")—C(4") | 129.6(10) |
| C(2")—C(3")—H(3") | 116.3(16) |
| C(4")—C(3")—H(3") | 114.1(15) |
| C(3")—C(4")—C(5") | 127.4(10) |
| C(3")—C(4")—C(9") | 125.4(9) |
| C(5")—C(4")—C(9") | 107.0(11) |
| C(4")—C(5")—C(6") | 120.8(10) |
| C(4")—C(5")—H(5") | 119.0(16) |
| C(6")—C(5")—H(5") | 120.1(15) |
| N(1")—C(6")—C(5") | 118.9(10) |
| N(1")—C(6")—C(7") | 112.2(11) |
| C(5")—C(6")—C(7") | 128.8(10) |
| O(5")—C(7")—C(6") | 126.1(10) |
| O(5")—C(7")—C(8") | 124.0(9) |
| C(6")—C(7")—C(8") | 109.9(11) |
| C(7")—C(8")—C(9") | 118.6(10) |
| C(7")—C(8")—C(11") | 108.8(11) |
| C(9")—C(8")—C(11") | 132.1(10) |
| O(1")—C(9")—C(4") | 110.7(10) |
| O(1")—C(9")—C(8") | 114.7(9) |
| C(4")—C(9")—C(8") | 134.7(10) |
| O(6")—C(10")—N(2") | 119.2(11) |
| O(6")—C(10")—C(2") | 121.3(10) |
| N(2")—C(10")—C(2") | 119.5(10) |
| C(8")—C(11")—H(11"A) | 114.3(12) |
| C(8")—C(11")—H(11"B) | 117.9(16) |
| C(8")—C(11")—H(11"C) | 105.1(15) |
| H(11"A)—C(11")—H(11"B) | 108.3(19) |
| H(11"A)—C(11")—H(11"C) | 104.2(19) |
| H(11"B)—C(11")—H(11"C) | 105.7(17) |
| N(2")—C(12")—C(13") | 131.3(9) |
| N(2")—C(12")—C(17") | 114.3(11) |
| C(13")—C(12")—C(17") | 114.4(12) |
| C(12")—C(13")—C(14") | 127.3(10) |
| C(12")—C(13")—H(13") | 117.4(15) |
| C(14")—C(13")—H(13") | 115.2(15) |
| C(13")—C(14")—C(15") | 118.8(11) |
| C(13")—C(14")—C(18") | 126.3(9) |
| C(15")—C(14")—C(18") | 114.7(12) |
| O(9")—C(15")—C(14") | 120.5(12) |
| O(9")—C(15")—C(16") | 125.2(10) |
| C(14")—C(15")—C(16") | 114.3(12) |
| C(15")—C(16")—C(17") | 128.6(10) |
| C(15")—C(16")—H(16") | 115.2(17) |
| C(17")—C(16")—H(16") | 116.0(17) |
| C(12")—C(17")—C(16") | 116.5(12) |
| C(12")—C(17")—H(17") | 119.0(16) |
| C(16")—C(17")—H(17") | 124.4(14) |
| O(7")—C(18")—O(8") | 126.0(12) |
| O(7")—C(18")—C(14") | 103.6(11) |
| O(8")—C(18")—C(14") | 129.0(11) |
| C(1''')—O(1''')—C(9''') | 128.4(8) |
| C(7''')—O(5''')—Ho(5''') | 111.2(17) |
| C(18''')—O(7''')—Ho(7''') | 118.2(17) |
| C(15''')—O(9''')—Ho(9''') | 108.4(15) |
| O(3''')—N(1''')—O(4''') | 128.1(9) |
| O(3''')—N(1''')—C(6''') | 109.6(10) |
| O(4''')—N(1''')—C(6''') | 122.1(10) |
| C(10''')—N(2''')—C(12''') | 135.2(9) |
| C(10''')—N(2''')—Hn(2''') | 113.5(15) |
| C(12''')—N(2''')—Hn(2''') | 111.3(14) |
| O(1''')—C(1''')—O(2''') | 119.3(10) |
| O(1''')—C(1''')—C(2''') | 121.7(8) |
| O(2''')—C(1''')—C(2''') | 118.9(11) |
| C(1''')—C(2''')—C(3''') | 108.9(10) |
| C(1''')—C(2''')—C(10''') | 122.6(8) |
| C(3''')—C(2''')—C(10''') | 128.2(9) |
| C(2''')—C(3''')—C(4''') | 129.6(10) |
| C(2''')—C(3''')—H(3''') | 114.7(16) |
| C(4''')—C(3''')—H(3''') | 115.7(15) |
| C(3''')—C(4''')—C(5''') | 130.5(10) |
| C(3''')—C(4''')—C(9''') | 123.2(9) |
| C(5''')—C(4''')—C(9''') | 106.0(10) |
| C(4''')—C(5''')—C(6''') | 126.9(9) |
| C(4''')—C(5''')—H(5''') | 116.5(16) |
| C(6''')—C(5''')—H(5''') | 116.6(15) |
| N(1''')—C(6''')—C(5''') | 123.0(10) |
| N(1''')—C(6''')—C(7''') | 112.0(11) |
| C(5''')—C(6''')—C(7''') | 125.0(10) |
| O(5''')—C(7''')—C(6''') | 128.5(10) |
| O(5''')—C(7''')—C(8''') | 122.9(9) |
| C(6''')—C(7''')—C(8''') | 108.6(11) |
| C(7''')—C(8''')—C(9''') | 124.1(9) |
| C(7''')—C(8''')—C(11''') | 107.5(10) |
| C(9''')—C(8''')—C(11''') | 128.5(9) |
| O(1''')—C(9''')—C(4''') | 108.1(10) |
| O(1''')—C(9''')—C(8''') | 122.7(9) |
| C(4''')—C(9''')—C(8''') | 129.2(9) |
| O(6''')—C(10''')—N(2''') | 115.7(11) |
| O(6''')—C(10''')—C(2''') | 117.2(9) |
| N(2''')—C(10''')—C(2''') | 125.8(9) |
| C(8''')—C(11''')—H(11'''A) | 115.6(15) |
| C(8''')—C(11''')—H(11'''B) | 113.6(12) |
| C(8''')—C(11''')—H(11'''C) | 105.8(15) |
| H(11'''A)—C(11''')—H(11'''B) | 107.7(20) |
| H(11'''A)—C(11''')—H(11'''C) | 106.6(17) |
| H(11'''B)—C(11''')—H(11'''C) | 107.0(19) |
| N(2''')—C(12''')—C(13''') | 125.6(9) |
| N(2''')—C(12''')—C(17''') | 119.0(10) |
| C(13''')—C(12''')—C(17''') | 115.3(11) |
| C(12''')—C(13''')—C(14''') | 125.3(9) |
| C(12''')—C(13''')—H(13''') | 115.0(15) |
| C(14''')—C(13''')—H(13''') | 119.8(14) |
| C(13''')—C(14''')—C(15''') | 118.9(11) |
| C(13''')—C(14''')—C(18''') | 126.8(12) |
| C(15''')—C(14''')—C(18''') | 114.3(11) |
| O(9''')—C(15''')—C(14''') | 122.6(11) |
| O(9''')—C(15''')—C(16''') | 120.3(9) |

TABLE 11-continued

The bond angle values of the sample of crystalline form III of XLF-III-43 (°)

| Bonding atoms | Bond angle |
|---|---|
| C(14''')—C(15''')—C(16''') | 116.7(11) |
| C(15''')—C(16''')—C(17''') | 121.8(9) |
| C(15''')—C(16''')—H(16''') | 119.5(17) |
| C(17''')—C(16''')—H(16''') | 118.8(16) |
| C(12''')—C(17''')—C(16''') | 121.9(11) |
| C(12''')—C(17''')—H(17''') | 117.5(16) |
| C(16''')—C(17''')—H(17''') | 120.5(14) |
| O(7''')—C(18''')—O(8''') | 120.8(11) |
| O(7''')—C(18''')—C(14''') | 109.6(11) |
| O(8''')—C(18''')—C(14''') | 128.7(11) |
| C(1A)—N(1A)—C(2A) | 113.8(12) |
| C(1A)—N(1A)—C(3A) | 119.3(11) |
| C(2A)—N(1A)—C(3A) | 126.4(10) |
| O(1A)—C(1A)—N(1A) | 121.3(12) |
| O(1A)—C(1A)—Hc(1A) | 118.8(15) |
| N(1A)—C(1A)—Hc(1A) | 119.8(17) |
| N(1A)—C(2A)—Hc(2AA) | 112.8(21) |
| N(1A)—C(2A)—Hc(2AB) | 110.4(18) |
| N(1A)—C(2A)—Hc(2AC) | 108.6(14) |
| Hc(2AA)—C(2A)—Hc(2AB) | 104.7(16) |
| Hc(2AA)—C(2A)—Hc(2AC) | 113.0(23) |
| Hc(2AB)—C(2A)—Hc(2AC) | 107.0(24) |
| N(1A)—C(3A)—Hc(3AA) | 112.1(17) |
| N(1A)—C(3A)—Hc(3AB) | 110.8(15) |
| N(1A)—C(3A)—Hc(3AC) | 105.8(17) |
| Hc(3AA)—C(3A)—Hc(3AB) | 103.9(19) |
| Hc(3AA)—C(3A)—Hc(3AC) | 110.8(18) |
| Hc(3AB)—C(3A)—Hc(3AC) | 113.6(21) |
| C(1B)—N(1B)—C(2B) | 127.7(12) |
| C(1B)—N(1B)—C(3B) | 112.2(13) |
| C(2B)—N(1B)—C(3B) | 119.4(11) |
| O(1B)—C(1B)—N(1B) | 131.4(13) |
| O(1B)—C(1B)—Hc(1B) | 116.6(17) |
| N(1B)—C(1B)—Hc(1B) | 111.7(18) |
| N(1B)—C(2B)—Hc(2BA) | 110.5(16) |
| N(1B)—C(2B)—Hc(2BB) | 113.3(18) |
| N(1B)—C(2B)—Hc(2BC) | 103.4(17) |
| Hc(2BA)—C(2B)—Hc(2BB) | 108.2(20) |
| Hc(2BA)—C(2B)—Hc(2BC) | 111.1(20) |
| Hc(2BB)—C(2B)—Hc(2BC) | 110.2(18) |
| N(1B)—C(3B)—Hc(3BA) | 107.1(19) |
| N(1B)—C(3B)—Hc(3BB) | 115.3(16) |
| N(1B)—C(3B)—Hc(3BC) | 113.6(20) |
| Hc(3BA)—C(3B)—Hc(3BB) | 101.2(21) |
| Hc(3BA)—C(3B)—Hc(3BC) | 105.8(20) |
| Hc(3BB)—C(3B)—Hc(3BC) | 112.4(24) |
| C(1C)—N(1C)—C(2C) | 124.6(11) |
| C(1C)—N(1C)—C(3C) | 115.1(13) |
| C(2C)—N(1C)—C(3C) | 120.0(13) |
| O(1C)—C(1C)—N(1C) | 131.5(11) |
| O(1C)—C(1C)—Hc(1C) | 117.1(16) |
| N(1C)—C(1C)—Hc(1C) | 111.4(17) |
| N(1C)—C(2C)—Hc(2CA) | 112.9(17) |
| N(1C)—C(2C)—Hc(2CB) | 111.4(17) |
| N(1C)—C(2C)—Hc(2CC) | 105.2(17) |
| Hc(2CA)—C(2C)—Hc(2CB) | 107.6(21) |
| Hc(2CA)—C(2C)—Hc(2CC) | 109.4(19) |
| Hc(2CB)—C(2C)—Hc(2CC) | 110.3(19) |
| N(1C)—C(3C)—Hc(3CA) | 111.8(20) |
| N(1C)—C(3C)—Hc(3CB) | 109.6(19) |
| N(1C)—C(3C)—Hc(3CC) | 109.5(15) |
| Hc(3CA)—C(3C)—Hc(3CB) | 111.2(19) |
| Hc(3CA)—C(3C)—Hc(3CC) | 106.3(22) |
| Hc(3CB)—C(3C)—Hc(3CC) | 108.3(23) |
| C(1D)—N(1D)—C(2D) | 95.2(15) |
| C(1D)—N(1D)—C(3D) | 147.9(13) |
| C(2D)—N(1D)—C(3D) | 114.0(14) |
| O(1D)—C(1D)—N(1D) | 150.2(14) |
| O(1D)—C(1D)—Hc(1D) | 107.6(21) |
| N(1D)—C(1D)—Hc(1D) | 102.0(21) |
| C(1E)—N(1E)—C(2E) | 124.8(20) |
| C(1E)—N(1E)—C(3E) | 110.1(13) |
| C(2E)—N(1E)—C(3E) | 125.1(19) |
| O(1E)—C(1E)—N(1E) | 119.9(14) |
| O(1E)—C(1E)—Hc(1E) | 123.2(18) |
| N(1E)—C(1E)—Hc(1E) | 116.8(20) |
| N(1E)—C(2E)—Hc(2EA) | 116.9(23) |
| N(1E)—C(2E)—Hc(2EB) | 112.5(24) |
| N(1E)—C(2E)—Hc(2EC) | 118.0(30) |
| Hc(2EA)—C(2E)—Hc(2EB) | 100.4(23) |
| Hc(2EA)—C(2E)—Hc(2EC) | 105.3(25) |
| Hc(2EB)—C(2E)—Hc(2EC) | 100.7(25) |
| N(1E)—C(3E)—Hc(3EA) | 113.6(17) |
| N(1E)—C(3E)—Hc(3EB) | 119.1(21) |
| N(1E)—C(3E)—Hc(3EC) | 102.0(18) |
| Hc(3EA)—C(3E)—Hc(3EB) | 108.6(23) |
| Hc(3EA)—C(3E)—Hc(3EC) | 103.6(22) |
| Hc(3EB)—C(3E)—Hc(3EC) | 108.4(20) |
| C(1F)—N(1F)—C(2F) | 135.2(11) |
| C(1F)—N(1F)—C(3F) | 114.7(13) |
| C(2F)—N(1F)—C(3F) | 109.7(13) |
| O(1F)—C(1F)—N(1F) | 133.5(11) |
| O(1F)—C(1F)—Hc(1F) | 112.9(16) |
| N(1F)—C(1F)—Hc(1F) | 113.6(17) |
| N(1F)—C(2F)—Hc(2FA) | 109.8(18) |
| N(1F)—C(2F)—Hc(2FB) | 108.1(16) |
| N(1F)—C(2F)—Hc(2FC) | 106.3(18) |
| Hc(2FA)—C(2F)—Hc(2FB) | 110.7(22) |
| Hc(2FA)—C(2F)—Hc(2FC) | 111.1(19) |
| Hc(2FB)—C(2F)—Hc(2FC) | 110.8(22) |
| N(1F)—C(3F)—Hc(3FA) | 115.4(18) |
| N(1F)—C(3F)—Hc(3FB) | 115.4(17) |
| N(1F)—C(3F)—Hc(3FC) | 106.7(17) |
| Hc(3FA)—C(3F)—Hc(3FB) | 104.8(22) |
| Hc(3FA)—C(3F)—Hc(3FC) | 106.4(21) |
| Hc(3FB)—C(3F)—Hc(3FC) | 107.5(22) |

2. When taking X-ray powder diffraction analysis ($CuK_\alpha$ irradiation), the solid substance of crystalline form III of XLF-III-43 shows diffraction peak position: 2-Theta values (°) or d values (Å), and relative intensity of diffraction peak: values of peak height (Height %). Below are the characteristic peak values of solid substances in crystalline state (Table 12, FIG. 12).

TABLE 12

The characteristic peak values of X-ray powder diffraction of the sample of crystalline form III of XLF-III-43

| Peak | 2-Theta | d (Å) | Height % |
|---|---|---|---|
| 1 | 13.3940 | 6.60 | 19 |
| 2 | 12.4622 | 7.09 | 11 |
| 3 | 11.8693 | 7.45 | 9 |
| 4 | 11.8162 | 7.48 | 8 |
| 5 | 10.6137 | 8.33 | 7 |
| 6 | 10.3712 | 8.53 | 69 |
| 7 | 7.0528 | 12.55 | 6 |
| 8 | 6.4666 | 13.69 | 42 |
| 9 | 6.3173 | 14.02 | 14 |
| 10 | 6.0474 | 14.65 | 7 |
| 11 | 5.9081 | 14.99 | 10 |
| 12 | 5.8471 | 15.15 | 3 |
| 13 | 5.7734 | 15.35 | 5 |
| 14 | 5.6435 | 15.70 | 19 |
| 15 | 5.3781 | 16.48 | 12 |
| 16 | 5.3446 | 16.59 | 12 |
| 17 | 5.3069 | 16.71 | 8 |
| 18 | 4.5269 | 19.61 | 13 |
| 19 | 4.4480 | 19.96 | 11 |
| 20 | 4.1832 | 21.24 | 16 |
| 21 | 4.0347 | 22.03 | 4 |
| 22 | 3.9313 | 22.62 | 4 |
| 23 | 3.8921 | 22.85 | 5 |
| 24 | 3.8448 | 23.13 | 3 |
| 25 | 3.8195 | 23.29 | 4 |

TABLE 12-continued

The characteristic peak values of X-ray powder diffraction
of the sample of crystalline form III of XLF-III-43

| Peak | 2-Theta | d (Å) | Height % |
|---|---|---|---|
| 26 | 3.6530 | 24.37 | 3 |
| 27 | 3.5837 | 24.84 | 11 |
| 28 | 3.5433 | 25.13 | 3 |
| 29 | 3.5379 | 25.17 | 30 |
| 30 | 3.5214 | 25.29 | 10 |
| 31 | 3.4694 | 25.68 | 3 |
| 32 | 3.3660 | 26.48 | 23 |
| 33 | 3.3338 | 26.74 | 3 |
| 34 | 3.3220 | 26.84 | 100 |
| 35 | 3.0567 | 29.21 | 18 |
| 36 | 2.9501 | 30.30 | 3 |

3. In the DSC spectrum of the solid substance of crystalline form III of XLF-III-43 (FIG. 13), there are a peak of heat absorption with the transition value at about 191° C., and a peak of heat emission with the transition value at about 293.5° C.

4. In the infrared absorption spectrum of the solid substance of crystalline form III of XLF-III-43 (FIG. 14), there are absorption peaks at 3238.6, 3081.4, 2787.8, 2469.8, 1728.7, 1670.1, 1621.1, 1557.1, 1529.8, 1488.3, 1472.0, 1443.3, 1361.5, 1346.3, 1314.6, 1284.3, 1234.4, 1195.6, 1117.9, 1071.0, 1022.7, 968.2, 916.6, 907.1, 893.4, 834.3, 825.1, 786.8, 763.0, 746.5, 727.1, 705.2, 673.9, 622.9, 578.7, 558.9, 529.2, 508.3, 461.0, 425.6 cm$^{-1}$, and the main characteristic absorption peaks of the solid substance of crystalline form III of XLF-III-43 are the peaks at 3081.4, 2469.8, 1728.7, 1529.8, 1284.3, 1234.4, 1195.6, 907.1, 825.1, 786.8, 705.2, 425.6 cm$^{-1}$.

According to crystalline form III of XLF-III-43 of the invention, optimize almost sterling of crystalline form III of XLF-III-43 as medicine active component (nearly don't include any other crystalline form of XLF-III-43. However, the invention also includes crystalline form III of XLF-III-43 which mixed with one or several other crystalline forms of XLF-III-43. If medicine active component is the mixture of crystalline form III of XLF-III-43 and other crystalline forms of XLF-III-43, the component should be optimized to include 50% of crystalline form III of XLF-III-43 at least, then optimize to include 70% of crystalline form III of XLF-III-43 at least, then 80%, 90%, 95%, at last greatest optimize to include 98% of crystalline form III of XLF-III-43 at least.

The invention also includes one pharmaceutical composition which contains crystalline form III of XLF-III-43 and vehicle which is acceptable in pharmacodynamics.

The invention also provides the preparation method of crystalline form III of XLF-III-43:

(a) Take the sample of XLF-III-43 into single or mixed solvent and heat to dissolve completely, then in the environment of in temperature scope of 65° C. to 75° C., relative humidity of below 90%, recryst for 100 to 240 hours, then obtain the solid substance sample of crystalline form III.
(b) Separate the solid substance sample of crystalline form III of XLF-III-43 from the solution.
(c) Dry the solid substance until the surface solvent is removed.

Solvent system could be single or mixed solvents. For example, the solvents could be DMF or mixed solvents that can mix with DMF. The single solvents that could be mixed with DMF are selected from methanol, ethanol, 95% ethanol, ammonia water, hydrochloric acid, and water. The optimized solvents are DMF, ethanol, 95% ethanol and DMF is the best.

Mixed solvents are selected from combinations of methanol, ethanol, 95% ethanol, DMF, ammonia water, hydrochloric acid, and water (combinations of two kinds of single solvents or more) with different matching proportions. The optimized mixed solvent is the mixture of DMF and water.

Temperature scope is 65° C. to 75° C., optimizing 67° C. to 74° C., greatest optimizing 68° C. to 72° C.

The relative humidity scope is below 90%, optimizing below 70%, preferably optimizing below 50%, greatest optimizing below 40%.

The crystalling time is from 100 to 240 hours, optimizing 110 to 180 hours, greatest optimizing 120 hours.

The Morphological Characteristics of Crystalline Form IV of XLF-III-43:

1. When taking X-ray single crystal diffraction to analyze the structure, the solid substance of crystalline form IV of XLF-III-43 shows the symmetry of triclinic system, the space group is P-1, and the cell parameters are, a=7.315 Å, b=8.074 Å, c=19.157 Å, α=98.91°, β=102.20°, γ=91.55°.

Figure 15:
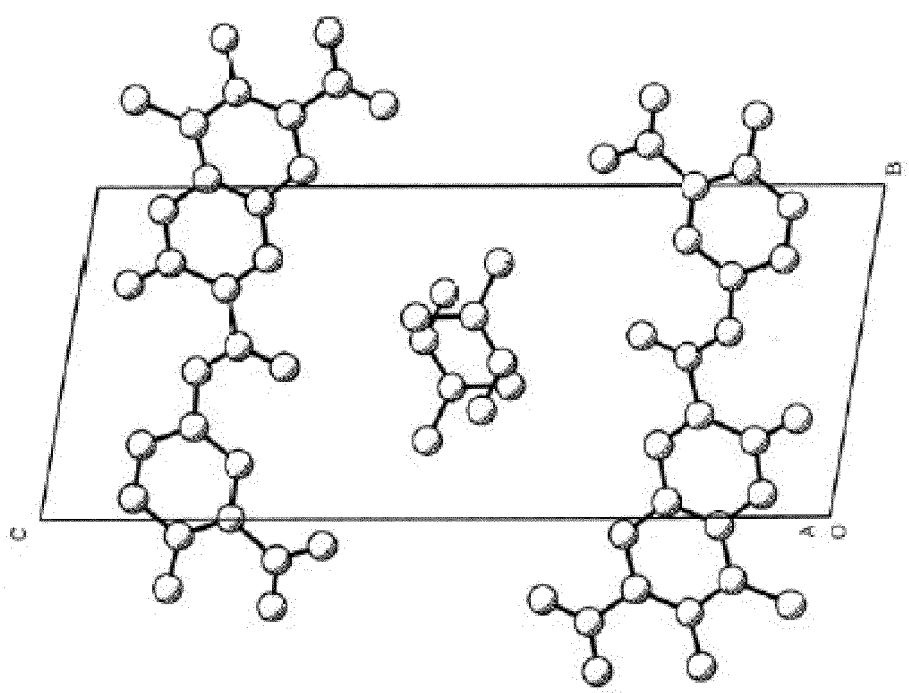

In solid substance sample of crystalline form IV, except the molecular of XLF-III-43, $C_{18}H_{12}N_2O_9$, the crystallized solvent molecular of N,N'-dimethyl formamide (DMF) also exists. In crystalline state, the proportion of the molecular of XLF-III-43 and N,N'-dimethyl formamide is 1:1. FIG. 15 shows the accumulation projection of the crystal unit of crystalline form IV of XLF-III-43. Table 13 shows the non-hydrogen atomic coordinate parameters of crystalline form IV of XLF-III-43. Table 14 shows the bond length values of bonding atoms of crystalline form IV of XLF-III-43. Table 15 shows bond angle values of bonding atoms of crystalline form IV of XLF-III-43.

TABLE 13

Non-hydrogen atomic coordinate parameters of the sample
of crystalline form IV of XLF-III-43(relative coordinate)

| Atoms | x | y | z | Biso |
|---|---|---|---|---|
| O1 | .2721(6) | .0695(5) | .0890(2) | 4.3(2) |
| O2 | .3969(7) | .2937(5) | .0609(2) | 5.6(3) |
| O3 | .0975(10) | −.2432(7) | .3464(3) | 8.5(4) |
| O4 | .0178(8) | −.4575(6) | .2639(3) | 7.4(3) |
| O5 | .0385(7) | −.4455(7) | .1316(3) | 5.8(2) |
| O6 | .4740(7) | .5463(5) | .2766(2) | 5.4(2) |
| O7 | .7007(7) | 1.0809(5) | .3614(2) | 6.2(3) |
| O8 | .8380(8) | 1.2618(6) | .3110(3) | 7.1(3) |
| O9 | .8301(7) | 1.2056(5) | .1743(3) | 5.4(2) |
| N1 | .0806(9) | −.3092(7) | .2840(3) | 5.9(3) |
| N2 | .5367(7) | .5567(6) | .1653(3) | 4.4(3) |
| C1 | .3569(9) | .2286(7) | .1095(3) | 4.4(3) |
| C2 | .3836(8) | .3062(7) | .1859(3) | 3.6(3) |
| C3 | .3282(9) | .2169(7) | .2328(3) | 3.8(3) |
| C4 | .2495(8) | .0472(7) | .2110(3) | 3.9(3) |
| C5 | .2002(9) | −.0491(7) | .2582(3) | 4.1(3) |
| C6 | .1303(9) | −.2133(7) | .2315(4) | 4.6(3) |
| C7 | .1106(9) | −.2844(8) | .1579(4) | 4.9(3) |
| C8 | .1564(9) | −.1879(7) | .1094(4) | 4.4(3) |
| C9 | .2279(9) | −.0247(7) | .1374(3) | 4.1(3) |
| C10 | .4712(9) | .4810(7) | .2136(3) | 4.1(3) |
| C11 | .1349(11) | −.2618(9) | .0301(4) | 6.1(4) |
| C12 | .6116(8) | .7234(7) | .1732(3) | 3.9(3) |
| C13 | .6504(9) | .8361(7) | .2387(3) | 3.9(3) |
| C14 | .7235(9) | .9969(7) | .2399(3) | 4.1(3) |
| C15 | .7571(9) | 1.0488(7) | .1773(4) | 4.5(3) |
| C16 | .7154(10) | .9357(8) | .1115(4) | 4.7(3) |
| C17 | .6449(9) | .7764(8) | .1106(3) | 4.3(3) |
| C18 | .7599(11) | 1.1228(8) | .3070(4) | 5.4(4) |
| OD | .7416(9) | .3228(7) | .4633(3) | 8.1(4) |
| ND | .7517(10) | .6072(8) | .4927(3) | 7.1(4) |
| CD1 | .7517(13) | .4652(10) | .4471(4) | 7.4(5) |
| CD2 | .7589(16) | .7670(12) | .4721(5) | 9.8(7) |
| CD3 | .7457(14) | .6035(12) | .5677(4) | 8.5(6) |

TABLE 14

The bond length values of the sample of crystalline form IV of XLF-III-43 (Å)

| Bonding atoms | Bond length |
|---|---|
| O(1)—C(1) | 1.388(7) |
| O(1)—C(9) | 1.373(7) |
| O(2)—C(1) | 1.223(7) |
| O(3)—N(1) | 1.218(8) |
| O(4)—N(1) | 1.258(7) |
| O(5)—C(7) | 1.380(7) |
| O(5)—Ho(5) | .975(9) |
| O(6)—C(10) | 1.234(7) |
| O(7)—C(18) | 1.298(8) |
| O(7)—Ho(7) | .979(9) |
| O(8)—C(18) | 1.245(8) |
| O(9)—C(15) | 1.389(7) |
| O(9)—Ho(9) | .978(9) |
| N(1)—C(6) | 1.462(8) |
| N(2)—C(10) | 1.349(8) |
| N(2)—C(12) | 1.428(7) |
| N(2)—Hn(2) | 1.034(9) |
| C(1)—C(2) | 1.471(8) |
| C(2)—C(3) | 1.357(8) |
| C(2)—C(10) | 1.521(8) |
| C(3)—C(4) | 1.451(8) |
| C(3)—H(3) | 1.096(9) |
| C(4)—C(5) | 1.381(8) |
| C(4)—C(9) | 1.413(8) |
| C(5)—C(6) | 1.400(8) |
| C(5)—H(5) | 1.102(9) |
| C(6)—C(7) | 1.413(9) |
| C(7)—C(8) | 1.389(9) |
| C(8)—C(9) | 1.403(8) |
| C(8)—C(11) | 1.519(9) |
| C(11)—H(11A) | 1.098(12) |
| C(11)—H(11B) | 1.089(12) |
| C(11)—H(11C) | 1.082(12) |
| C(12)—C(13) | 1.406(8) |
| C(12)—C(17) | 1.404(8) |
| C(13)—C(14) | 1.401(8) |
| C(13)—H(13) | 1.106(11) |
| C(14)—C(15) | 1.396(9) |
| C(14)—C(18) | 1.487(9) |
| C(15)—C(16) | 1.411(9) |
| C(16)—C(17) | 1.383(8) |
| C(16)—H(16) | 1.117(11) |
| C(17)—H(17) | 1.104(10) |
| Od—Cd(1) | 1.240(10) |
| Nd—Cd(1) | 1.331(9) |
| Nd—Cd(2) | 1.414(12) |
| Nd—Cd(3) | 1.449(10) |
| Cd(1)—Hcd(1) | 1.102(12) |
| Cd(2)—Hcd(2A) | 1.080(12) |
| Cd(2)—Hcd(2B) | 1.140(15) |
| Cd(2)—Hcd(2C) | 1.088(13) |
| Cd(3)—Hcd(3A) | 1.082(12) |
| Cd(3)—Hcd(3B) | 1.113(14) |
| Cd(3)—Hcd(3C) | 1.115(13) |

TABLE 15

The bond angle values of the sample of crystalline form IV of XLF-III-43 (°)

| Bonding atoms | Bond angle |
|---|---|
| O(1)—C(1) | 1.388(7) |
| O(1)—C(9) | 1.373(7) |
| O(2)—C(1) | 1.223(7) |
| O(3)—N(1) | 1.218(8) |
| O(4)—N(1) | 1.258(7) |
| O(5)—C(7) | 1.380(7) |
| O(5)—Ho(5) | .975(9) |
| O(6)—C(10) | 1.234(7) |
| O(7)—C(18) | 1.298(8) |
| O(7)—Ho(7) | .979(9) |
| O(8)—C(18) | 1.245(8) |
| O(9)—C(15) | 1.389(7) |
| O(9)—Ho(9) | .978(9) |
| N(1)—C(6) | 1.462(8) |
| N(2)—C(10) | 1.349(8) |
| N(2)—C(12) | 1.428(7) |
| N(2)—Hn(2) | 1.034(9) |
| C(1)—C(2) | 1.471(8) |
| C(2)—C(3) | 1.357(8) |
| C(2)—C(10) | 1.521(8) |
| C(3)—C(4) | 1.451(8) |
| C(3)—H(3) | 1.096(9) |
| C(4)—C(5) | 1.381(8) |
| C(4)—C(9) | 1.413(8) |
| C(5)—C(6) | 1.400(8) |
| C(5)—H(5) | 1.102(9) |
| C(6)—C(7) | 1.413(9) |
| C(7)—C(8) | 1.389(9) |
| C(8)—C(9) | 1.403(8) |
| C(8)—C(11) | 1.519(9) |
| C(11)—H(11A) | 1.098(12) |
| C(11)—H(11B) | 1.089(12) |
| C(11)—H(11C) | 1.082(12) |
| C(12)—C(13) | 1.406(8) |
| C(12)—C(17) | 1.404(8) |
| C(13)—C(14) | 1.401(8) |
| C(13)—H(13) | 1.106(11) |
| C(14)—C(15) | 1.396(9) |
| C(14)—C(18) | 1.487(9) |
| C(15)—C(16) | 1.411(9) |
| C(16)—C(17) | 1.383(8) |
| C(16)—H(16) | 1.117(11) |
| C(17)—H(17) | 1.104(10) |
| Od—Cd(1) | 1.240(10) |
| Nd—Cd(1) | 1.331(9) |
| Nd—Cd(2) | 1.414(12) |
| Nd—Cd(3) | 1.449(10) |
| Cd(1)—Hcd(1) | 1.102(12) |
| Cd(2)—Hcd(2A) | 1.080(12) |
| Cd(2)—Hcd(2B) | 1.140(15) |
| Cd(2)—Hcd(2C) | 1.088(13) |
| Cd(3)—Hcd(3A) | 1.082(12) |
| Cd(3)—Hcd(3B) | 1.113(14) |
| Cd(3)—Hcd(3C) | 1.115(13) |

2. When taking X-ray powder diffraction analysis (CuK$_\alpha$ irradiation), the solid substance of crystalline form IV crystal of XLF-III-43 shows diffraction peak position: 2-Theta values (°) or d values (Å), and relative intensity of diffraction peak: values of peak height (Height %). Below are the characteristic peak values of solid substances in crystalline state (Table 6, FIG. 16).

TABLE 6

The characteristic peak values of X-ray powder diffraction of the sample of crystalline form IV of XLF-III-43

| Peak | 2-Theta | d(Å) | Height % |
|---|---|---|---|
| 1 | 18.4697 | 4.78 | 67 |
| 2 | 9.2348 | 9.58 | 100 |
| 3 | 7.7913 | 11.36 | 7 |
| 4 | 6.9098 | 12.81 | 20 |
| 5 | 6.5893 | 13.44 | 14 |
| 6 | 6.1566 | 14.39 | 38 |
| 7 | 5.3469 | 16.58 | 21 |
| 8 | 5.1308 | 17.28 | 13 |
| 9 | 4.8331 | 18.36 | 7 |
| 10 | 4.6588 | 19.05 | 7 |
| 11 | 4.3138 | 20.59 | 8 |
| 12 | 4.2275 | 21.01 | 4 |

TABLE 6-continued

The characteristic peak values of X-ray powder diffraction of the sample of crystalline form IV of XLF-III-43

| Peak | 2-Theta | d(Å) | Height % |
|---|---|---|---|
| 13 | 3.9890 | 22.29 | 13 |
| 14 | 3.7659 | 23.62 | 3 |
| 15 | 3.6550 | 24.35 | 14 |
| 16 | 3.5680 | 24.95 | 16 |
| 17 | 3.4549 | 25.79 | 5 |
| 18 | 3.3339 | 26.74 | 90 |
| 19 | 3.2061 | 27.83 | 37 |
| 20 | 3.0087 | 29.69 | 27 |
| 21 | 2.5729 | 34.87 | 2 |
| 22 | 2.4460 | 36.74 | 2 |
| 23 | 2.4273 | 37.04 | 3 |
| 24 | 2.3809 | 37.78 | 7 |
| 25 | 2.2889 | 39.36 | 8 |
| 26 | 2.1545 | 41.93 | 6 |
| 27 | 2.1055 | 42.95 | 2 |
| 28 | 2.0689 | 43.75 | 4 |
| 29 | 2.0144 | 45.00 | 2 |
| 30 | 1.9903 | 45.58 | 2 |
| 31 | 1.9127 | 47.54 | 2 |
| 32 | 1.6670 | 55.09 | 4 |
| 33 | 1.6405 | 56.06 | 2 |

3. In the DSC spectrum of the solid substance of crystalline form IV of XLF-III-43 (FIG. 17), there are two peaks of heat absorption with the transition values at about 94° C. and 172° C., and a peak of heat emission with the transition value at about 342° C.
4. In the infrared absorption spectrum of the solid substance of crystalline form IV of XLF-III-43 (FIG. 18), there are absorption peaks at 3565.3, 3488.9, 3238.7, 3104.2, 1719.8, 1669.1, 1621.6, 1560.6, 1537.0, 1488.0, 1471.6, 1445.9, 1379.1, 1359.7, 1313.6, 1285.7, 1258.6, 1152.8, 1237.1, 1194.2, 1118.6, 1071.3, 1021.5, 968.3, 917.5, 893.2, 848.5, 835.4, 789.2, 763.4, 746.7, 727.2, 674.4, 623.1, 579.1, 559.4, 528.8, 506.1, 427.9 cm$^{-1}$, and the main characteristic absorption peaks of the solid substance of crystalline form IV of XLF-III-43 are the peaks at 3565.3, 3488.9, 3238.7, 1719.8, 1669.1, 1560.6, 1379.1, 1258.6, 1237.1, 1194.2, 835.4, 427.9 cm$^{-1}$.

According to crystalline form IV of XLF-III-43 of the invention, optimize almost sterling of crystalline form IV of XLF-III-43 as medicine active component (nearly don't include any other crystalline form of XLF-III-43. However, the invention also includes crystalline form IV of XLF-III-43 which mixed with one or several other crystalline forms of XLF-III-43. If medicine active component is the mixture of crystalline form IV of XLF-III-43 and other crystalline forms of XLF-III-43, the component should be optimized to include 50% of crystalline form IV of XLF-III-43 at least, then optimize to include 70% of crystalline form IV of XLF-III-43 at least, then 80%, 90%, 95%, at last greatest optimize to include 98% of crystalline form IV of XLF-III-43 at least.

The invention also includes one pharmaceutical composition which contains crystalline form IV of XLF-III-43 and vehicle which is acceptable in pharmacodynamics.

The invention also provides the preparation method of crystalline form IV of XLF-III-43:
(a) Take the sample of XLF-III-43 into single or mixed solvent and heat to dissolve completely, then in the environment of in temperature scope of 85° C. to 95° C., relative humidity of below 90%, recryst completely and obtain the solid substance sample of crystalline form IV.
(b) Separate the solid substance sample of crystalline form IV of XLF-III-43 from the solution.
(c) Dry the solid substance until the surface solvent is removed.

Solvent system could be single or mixed solvents. For example, the solvents could be DMF or mixed solvents that can mix with DMF. The single solvents that could be mixed with DMF are selected from methanol, ethanol, 95% ethanol, ammonia water, hydrochloric acid, and water. The optimized solvents are DMF, ethanol, 95% ethanol and DMF is the best.

Mixed solvents are selected from combinations of methanol, ethanol, 95% ethanol, DMF, ammonia water, hydrochloric acid, and water (combinations of two kinds of single solvents or more) with different matching proportions. The optimized mixed solvent is the mixture of DMF and water.

Temperature scope is 85° C. to 95° C., optimizing 87° C. to 94° C., greatest optimizing 88° C. to 92° C.

The relative humidity scope is below 90%, optimizing below 70%, preferably optimizing below 50%, greatest optimizing below 40%.

The crystalling time is from 24 to 120 hours, optimizing 36 to 96 hours, greatest optimizing 72 hours.

The Morphological Characteristics of Crystalline Form V (Amorphous Form) of XLF-III-43:
1. The solid substance of crystalline form V of XLF-III-43 is characterized with including associated water in the sample of amorphous form, but not other solvent molecular. When taking X-ray powder diffraction analysis (CuK$_\alpha$ irradiation), the solid substance of crystalline form V of XLF-III-43 shows diffraction peak position: 2-Theta values (°) or d values (Å), and relative intensity of diffraction peak: values of peak height (Height %). Below are the characteristic peak values of solid substances in crystalline state (Table 17, FIG. 19).

TABLE 17

The characteristic peak values of X-ray powder diffraction of the sample of type V crystal of XLF-III-43

| Peak | 2-Theta | d(Å) | Height % |
|---|---|---|---|
| 1 | 5.661 | 15.60 | 9 |
| 2 | 11.440 | 7.73 | 99 |
| 3 | 13.420 | 6.59 | 10 |
| 4 | 14.737 | 6.01 | 1 |
| 5 | 15.800 | 5.60 | 4 |
| 6 | 17.220 | 5.14 | 11 |
| 7 | 17.778 | 4.98 | 3 |
| 8 | 20.800 | 4.27 | 9 |
| 9 | 22.960 | 3.87 | 1 |
| 10 | 23.880 | 3.72 | 1 |
| 11 | 26.780 | 3.33 | 100 |
| 12 | 28.923 | 3.08 | 2 |
| 13 | 31.561 | 2.83 | 2 |
| 14 | 36.020 | 2.49 | 2 |
| 15 | 37.159 | 2.42 | 1 |
| 16 | 41.060 | 2.10 | 1 |
| 17 | 43.860 | 2.06 | 2 |
| 18 | 45.440 | 1.99 | 1 |
| 19 | 53.958 | 1.70 | 2 |

2. In the DSC spectrum of the solid substance of crystalline form V (amorphous form) of XLF-III-43 (FIG. 20), there are a peak of heat absorption with the transition value at about 169° C., and a peak of heat emission with the transition value at about 345° C.
3. In the infrared absorption spectrum of the solid substance of crystalline form V (amorphous form) of XLF-III-43 (FIG. 21), there are absorption peaks at 3565.3, 3488.9, 3238.7, 3104.2, 1719.8, 1669.1, 1621.6, 1560.6, 1537.0, 1488.0, 1471.6, 1445.9, 1379.1, 1359.7, 1313.6, 1285.7, 1258.6, 1152.8, 1237.1, 1194.2, 1118.6, 1071.3, 1021.5, 968.3, 917.5, 893.2, 848.5, 835.4, 789.2, 763.4, 746.7, 727.2, 674.4, 623.1, 579.1, 559.4, 528.8, 506.1, 427.9 cm$^{-1}$, and the main characteristic absorption peaks of the solid substance of crystalline form V of XLF-III-43 are the peaks at 3565.3, 3488.9, 3238.7, 1719.8, 1669.1, 1560.6, 1379.1, 1258.6, 1237.1, 1194.2, 835.4, 427.9 cm$^{-1}$.

According to crystalline form V of XLF-III-43 of the invention, optimize almost sterling of crystalline form V of XLF-III-43 as medicine active component (nearly don't include any other crystalline form of XLF-III-43. However, the invention also includes crystalline form V of XLF-III-43 which mixed with one or several other crystalline forms of XLF-III-43. If medicine active component is the mixture of crystalline form V of XLF-III-43 and other crystalline forms of XLF-III-43, the component should be optimized to include 50% of crystalline form V of XLF-III-43 at least, then optimize to include 70% of crystalline form V of XLF-III-43 at least, then 80%, 90%, 95%, at last greatest optimize to include 98% of crystalline form V of XLF-III-43 at least.

The invention also includes one pharmaceutical composition which contains crystalline form V of XLF-III-43 and vehicle which is acceptable in pharmacodynamics.

The invention also provides the preparation method of crystalline form V (amorphous form) of XLF-III-43:
(a) Take the sample of XLF-III-43 into single or mixed solvent and heat to dissolve completely, then in the environment of in temperature scope of 75° C. to 85° C., relative humidity of below 90%, recryst completely and obtain the solid substance sample of XLF-III-43.
(b) Separate the solid substance sample of XLF-III-43 from the solution.
(c) Transfer crystal in dilute hydrochloric acid for above 1 day, and obtain the solid substance sample of crystalline form V.
(d) Dry the solid substance until the surface solvent is removed.

Solvent system could be single or mixed solvents. For example, the solvents could be DMF or mixed solvents that can mix with DMF. The single solvents that could be mixed with DMF are selected from methanol, ethanol, 95% ethanol, ammonia water, hydrochloric acid, and water. The optimized solvents are DMF, ethanol, 95% ethanol and DMF is the most.

Mixed solvents are selected from combinations of methanol, ethanol, 95% ethanol, DMF, ammonia water, hydrochloric acid, and water (combinations of two kinds of single solvents or more) with different matching proportions. The optimized mixed solvent is the mixture of DMF and water.

Temperature scope is 75° C. to 85° C., optimizing 77° C. to 84° C., greatest optimizing 78° C. to 82° C.

The relative humidity scope is below 90%, optimizing below 70%, preferably optimizing below 50%, greatest optimizing below 40%.

The crystalling time is from 24 to 120 hours, optimizing 36 to 96 hours, greatest optimizing 48 hours.

The invention also refers to pharmaceutical compositions which take the solid substances of the five crystalline forms of XLF-III-43 as active components. The characteristic of preparing pharmaceutical composition is that several excipients are mixed with one sterling of crystalline forms of XLF-III-43, form I, form II, form III, form IV, form V, or mixed crystals mixed from different crystalline forms of XLF-III-43 with different proportions.

These compound medicines are prepared with public methods in medicine domain. The samples of crystalline forms of XLF-III-43 can be combined together with one or more kinds of solid or liquid excipients and/or adjuvants which are acceptable in pharmacy, then made into any preparations suitable for using by people or animals. The contents of the crystalline samples of XLF-III-43 in pharmaceutical compositions are usually about 0.1% to 95% in weight.

The crystalline sample of XLF-III-43 or its pharmaceutical compositions could be administered with unit dose. The routes of administration could be intestinal tract or non-intestinal tract, such as oral administration, intravenous injection, intramuscular injection, subcutaneous injection, nasal cavity, oral mucosa, eye, lung and respiratory tract, skin, vagina, rectum, and so on.

The dosage forms of administration could be liquid, solid or semisolid. Liquid dosage forms could be solution (including true solution and colloid solution), emulsion (including o/w, w/o and multiple emulsion), suspension, injection (including fluid acupuncture, injectable powder and transfusion), eye drop, nasal drop, lotion and liniment. Solid dosages could be tablet (including ordinary tablet, enteric coated tablet, buccal tablet, dispersible tablet, chewable tablet, effervescent tablet, disintegrated tablet in oral cavity), capsule (including hard capsule, elastic capsule, enteric capsule), granule, powder, small pill, drop pill, suppository, pellicle, coating, aerosol, nebula. Semisolid dosages could be ointment, gelata, pasta.

The crystalline sample of XLF-III-43 could be made into ordinary preparation, as well as sustained release system, controlled release system, targeting preparation and all kinds of particulate delivery system.

In order to make the crystalline sample of XLF-III-43 into tablet, various kinds of excipients known in medicine domain could be generally used, including diluent, adhesive, wetter, disintegrant, lubricant, glidant. Diluent could be starch, dextrin, sucrose, glucose, lactose, mannitol, sorbitol, xylitol, microcrystalline cellulose, calcium sulfate, calcium phosphate, calcium carbonate etc. Wetter could be water, ethanol, isopropanol etc. Adhesive could be starch paste, dextrin, syrup, honey, glucose solution, microcrystalline cellulose, acacia mucilage, gelatin mucilage, sodium carboxymethyl cellulose, methylcellulose, hydroxypropyl methylcellulose, ethylcellulose, acrylic resin, carbomer, polyvinylpyrrolidone, polyethylene glycol etc. Disintegrant could be dried starch, microcrystalline cellulose, oligo-substituted hydroxypropylcellulose, crospolyvinylpyrrolidine, croscarmellose sodium, sodium carboxymethyl starch, sodium bicarbonate and citric acid, polyoxyethylene sorbitol fatty acid ester, sodium dodecylsulphate etc. Lubricant and glidant could be talc powder, silica dioxide, stearate, tartrate, liquid paraffin, polyethylene glycol etc.

Further more, tablet could also be made into coated tablet, such as sugar coated tablet, film coated tablet, enteric-coated tablet, double layer tablet, multilayer tablet.

In order to make the dosage unit into capsule, as active component, the crystal sample of XLF-III-43 can be mixed with diluent and glidant, then take the mixture into hard capsule or elastic capsule. It also could be that after mix the active component, the crystalline samples of XLF-III-43, with diluent, adhesive, disintegrant and make into granules or small pills, take them into hard granule or elastic granule. Various kinds of diluent, adhesive, wetter, disintegrant and glidant used in making the tablets of the crystalline samples of XLF-III-43, can also used in making the capsules of the crystalline samples of XLF-III-43.

In order to make the crystalline sample of XLF-III-43 into injection, the solvents could be water, ethanol, isopropanol, propylene glycol or their mixtures. And solubilizer, solution adjuvant, pH regulator, osmotic pressure regulator commonly used in medicine domain should be added into the solvents moderately. Solubilizer or solution adjuvant could be poloxamer, lecithin, hydroxylpropyl-β-cyclodextrin etc. PH regulator could be phosphate, acetate, hydrochloric acid, sodium hydroxide etc. Osmotic pressure regulator could be sodium chloride, mannitol, glucose, phosphate, acetate etc. If make freeze-dried injectable powder, mannitol and glucose could be used as support agent.

Furthermore, requestedly, coloring agent, perservative, aromatizer, correctant or other additives could be added into pharmaceutical preparations.

In order to achieve the intention of administration and potentialize therapeutic effects, the medicines or pharmaceutical compositions of the invention could be administered by any known medication.

The dosages of the pharmaceutical compositions of the crystalline samples of XLF-III-43 could be varied in wide range, depending on the characteristics and severities of the diseases to prevent and treat, individual conditions of patient and animal, routes of administration and dosage forms. Generally speaking, the suitable dosage range of the crystal sample of XLF-III-43 per day is about 0.001 to 150 mg/Kg body weight, optimizing 0.1 to 100 mg/Kg body weight, preferably 1 to 60 mg/Kg body weight, greatest 2 to 30 mg/Kg body weight. The dosage above could be one dosage unit or divided into several dosage units, depending on doctor's clinical experience and dosage regimens in applying other therapeutic tools.

The compounds or assemblages of the invention could be taken uniquely, or be combined with other curatives or medicines used in symptomatic treatments. When the compounds are used to cooperate with other curatives, should adjust their dosages according to practical conditions.

The invention has discovered that XLF-III-43 has solid existence condition with five different crystalline forms, form I, form II, form III, form IV and form V. Provided herein are five different preparing technologies for the crystalline samples. It has also been discovered that different crystalline samples of XLF-III-43 have different blood drug levels in living bodies. Also provided herein are crude drugs and solid pharmaceutical compositions with different dosages in which the sterling of the five crystalline forms and the samples of mixed crystals with different proportions are taken as active components. Further disclosed herein is that the crystalline samples of XLF-III-43 could be taken as crude drugs in prevent and/or treating kidney dysfunction, cardiocerebral vessel diseases, hypertension, type II diabetic mellitus, complications of hypertension and diabetic mellitus, tumor, precancerosis and edema, especially in preventing and/or treating diabetic nephropathy, hypertension nephropathy. Also disclosed herein is that the crystalline forms can affect the blood drug levels of XLF-III-43 in living bodies, and the crystalline forms can enhance clinical therapeutic effects of medicines to bring preventive and therapeutic effects.

Nomenclatures or Abbreviations

N,N'-dimethyl formamide (or named DMF), molecular formula $(CH_3)_2NCHO$.

ILLUSTRATIONS OF ANNEX FIGURES

FIG. 1 The molecular structure of XLF-III-43

FIG. 2 The tereochemical structure projection of the molecular of XLF-III-43

FIG. 3 The accumulation projection of the crystal unit of crystalline form I of XLF-III-43

Figure 4:
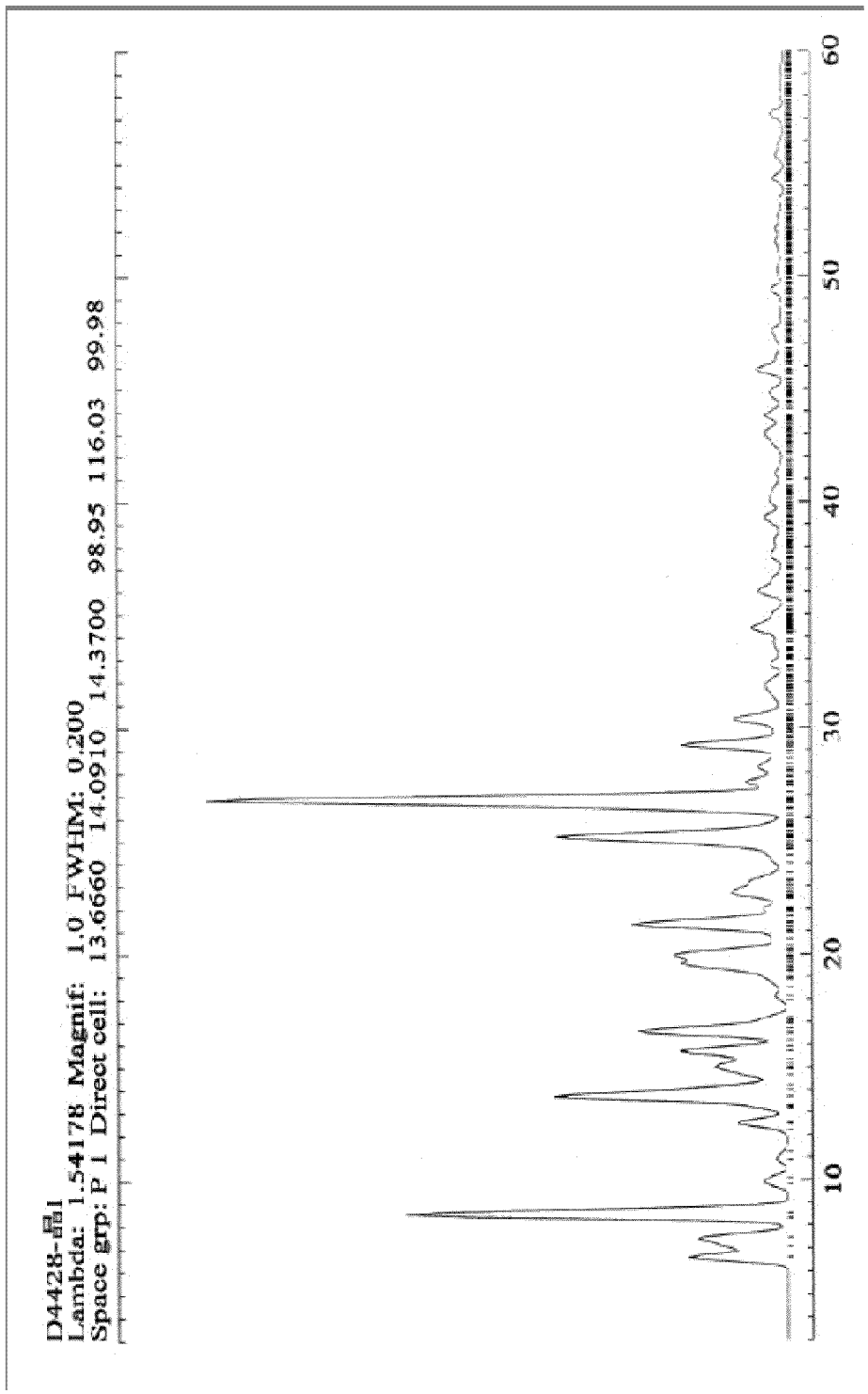

FIG. 4 The X-ray powder diffraction spectrum of crystalline form I sample of XLF-III-43

Figure 5:
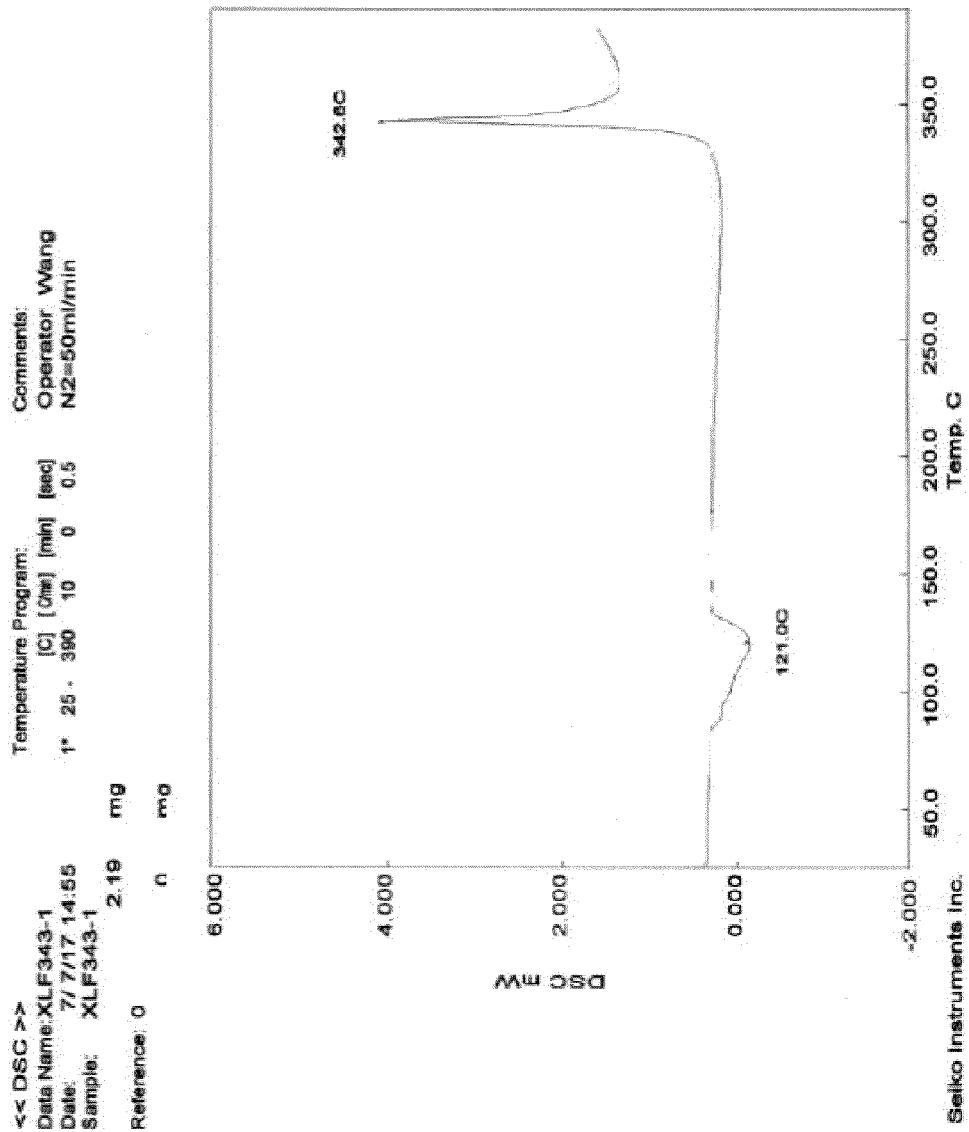

FIG. 5 The DSC spectrum of the crystalline form I sample of XLF-III-43

Figure 6:
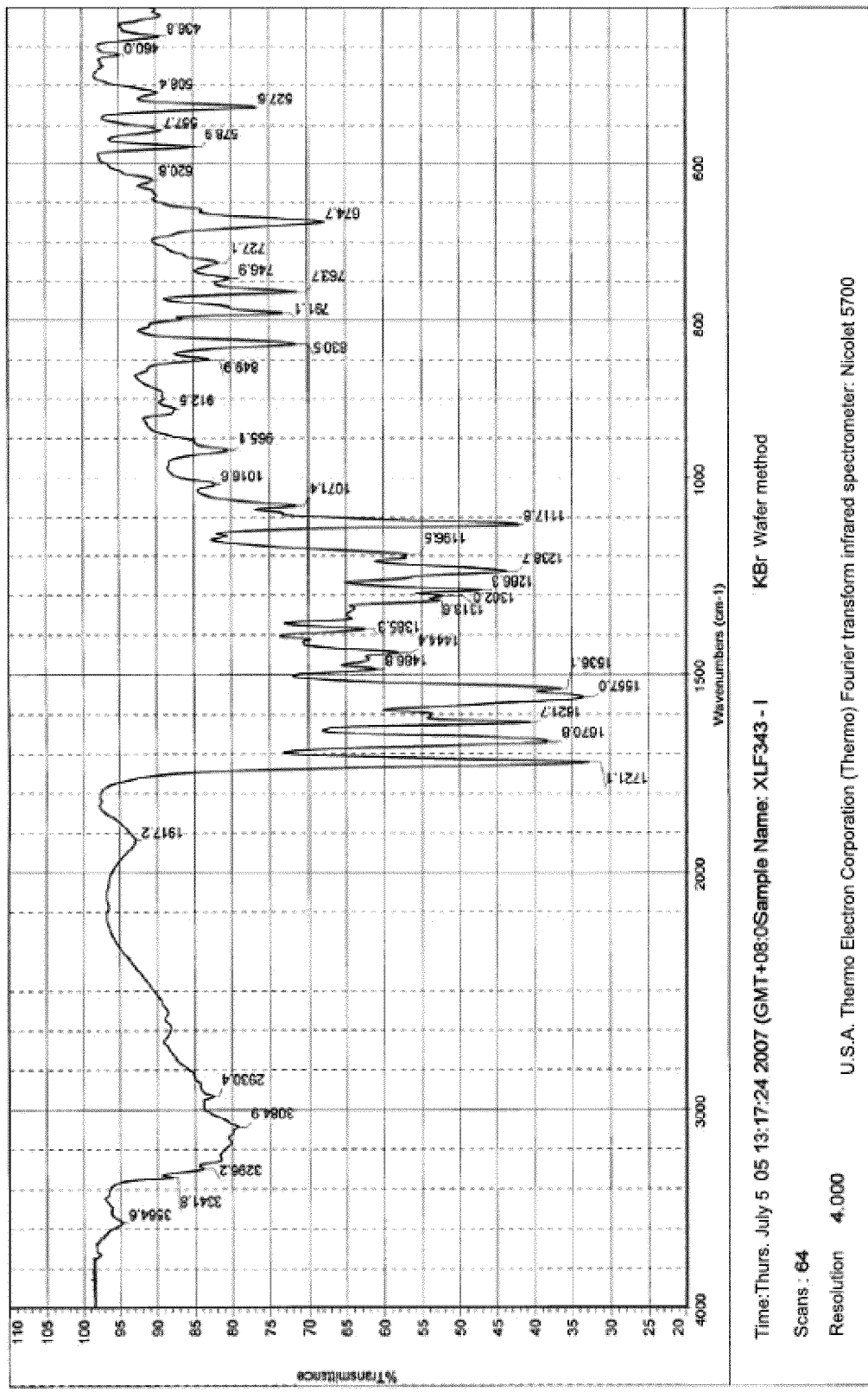

FIG. 6 The infrared absorption spectrum of the crystalline form I sample of XLF-III-43

FIG. 7 The accumulation projection of the crystal unit of crystalline form II of XLF-III-43

Figure 8:
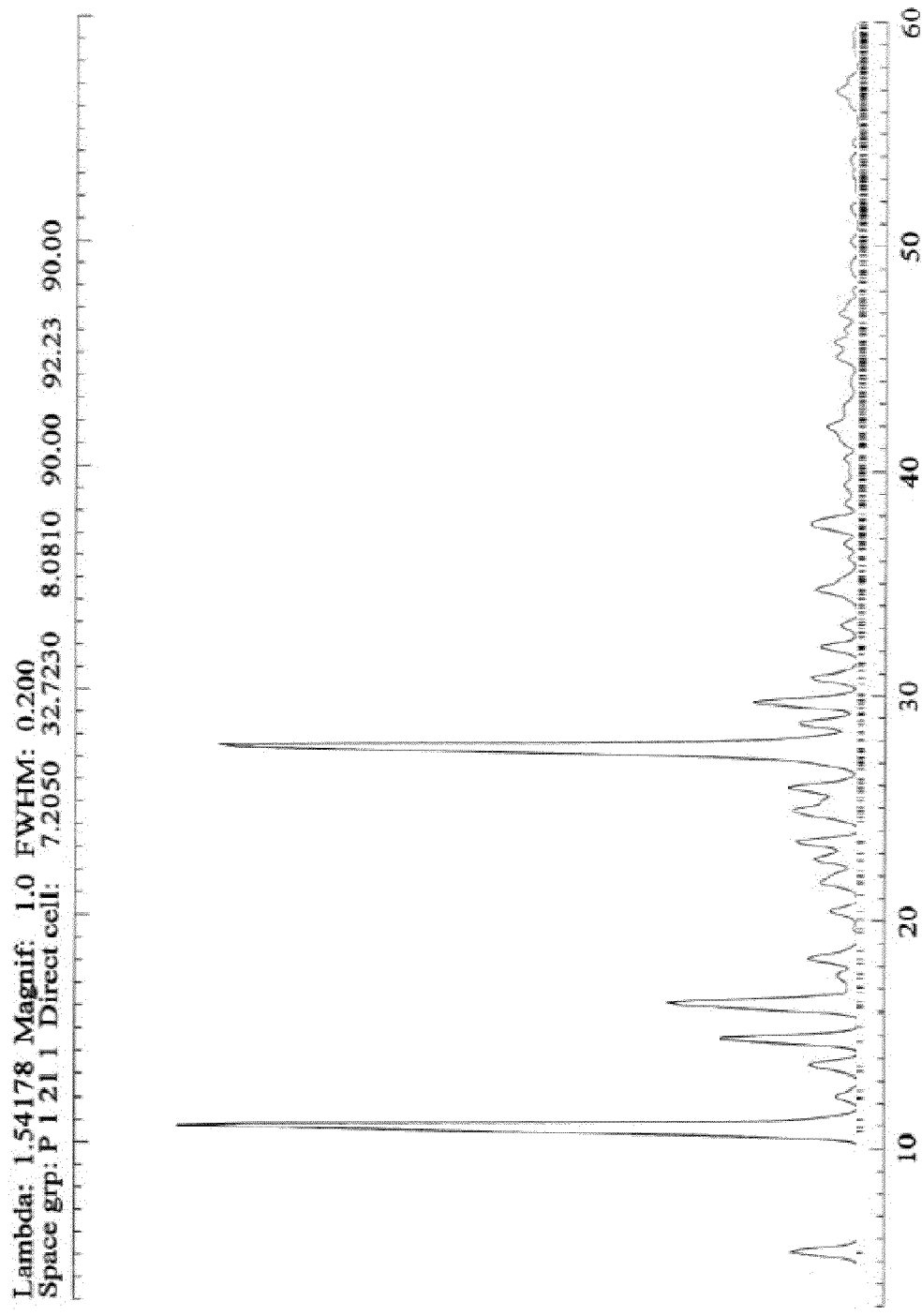

FIG. 8 The X-ray powder diffraction spectrum of crystalline form II sample of XLF-III-43

Figure 9:
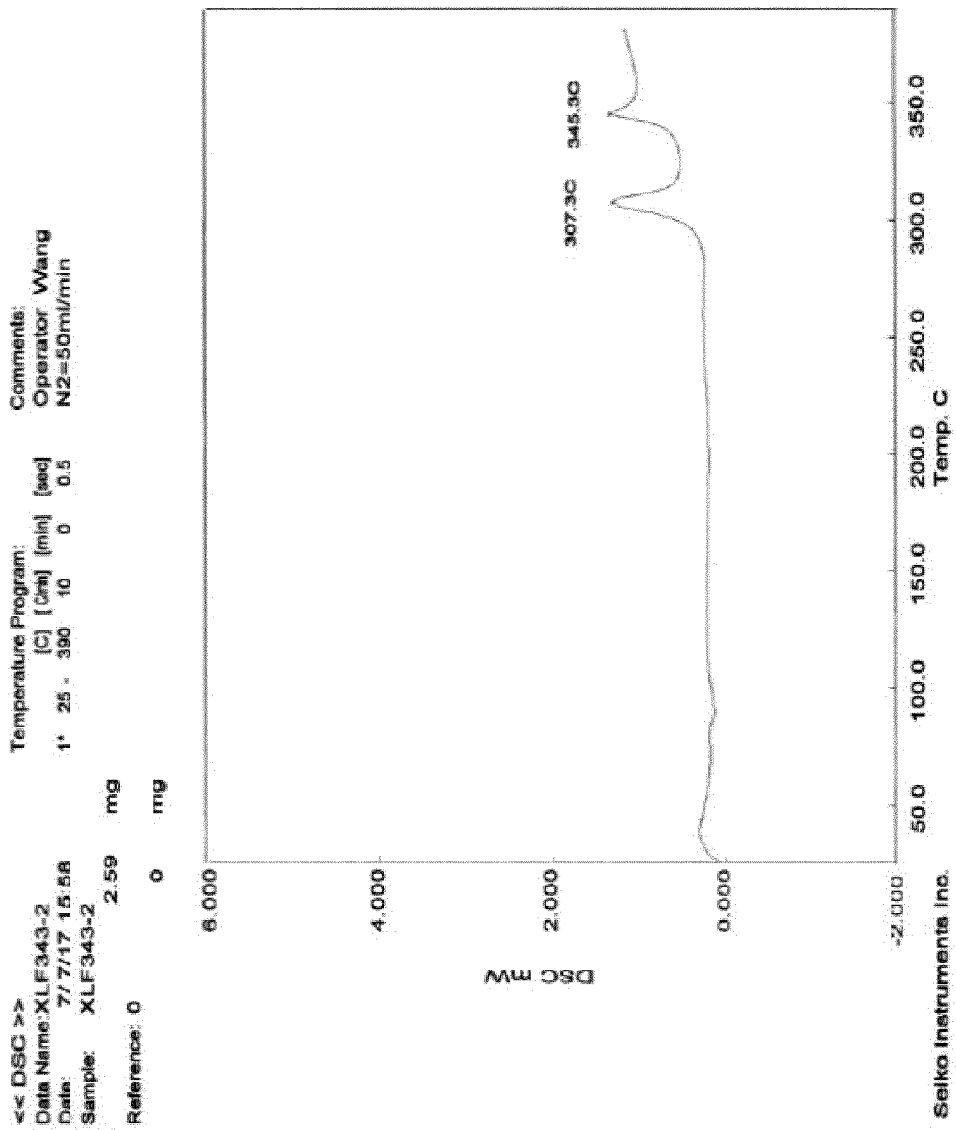

FIG. 9 The DSC spectrum of the crystalline form II sample of XLF-III-43

Figure 10:
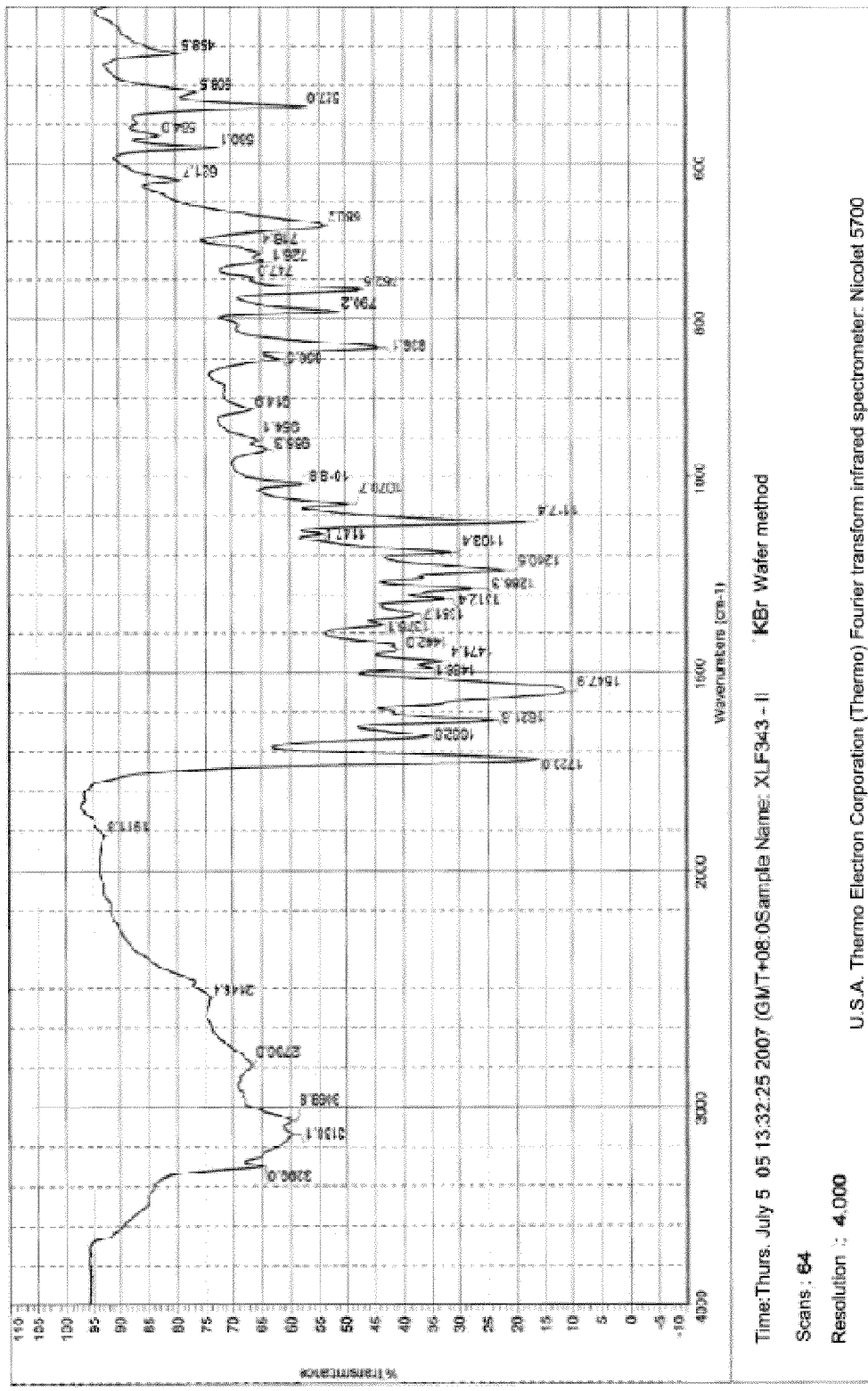

FIG. 10 The infrared absorption spectrum of the crystalline form II sample of XLF-III-43

FIG. 11 The accumulation projection of the crystal unit of crystalline form III of XLF-III-43

Figure 12:
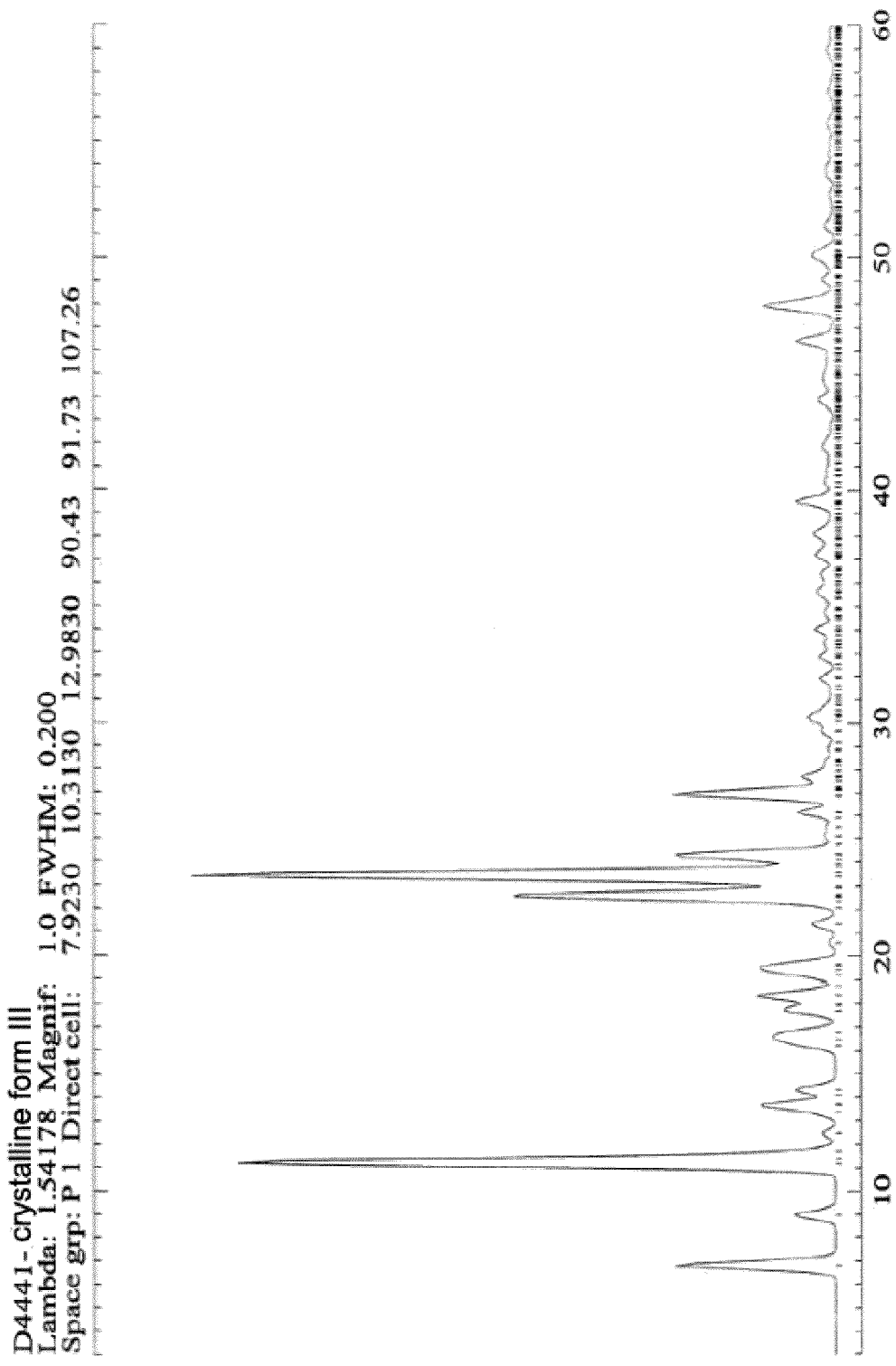

FIG. 12 The X-ray powder diffraction spectrum of crystalline form III sample of XLF-III-43

Figure 13:
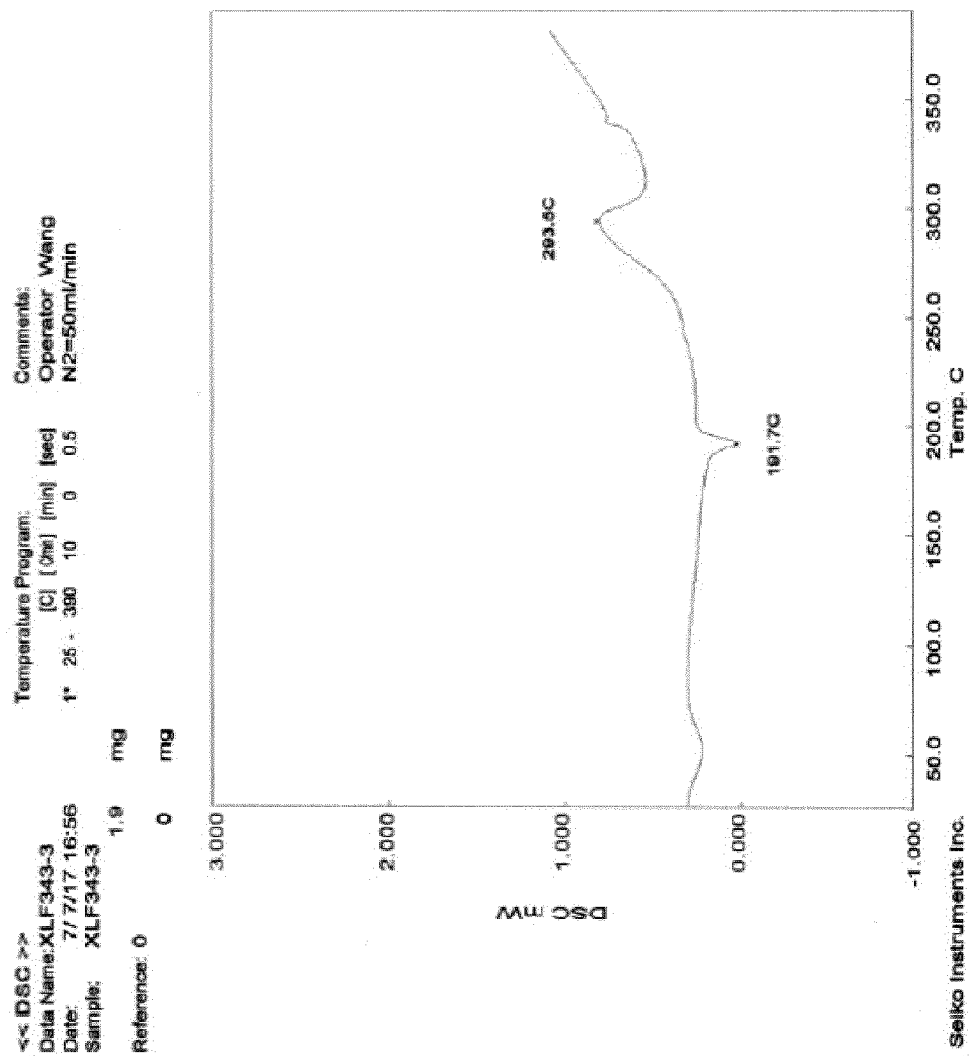

FIG. 13 The DSC spectrum of the crystalline form III sample of XLF-III-43

Figure 14:
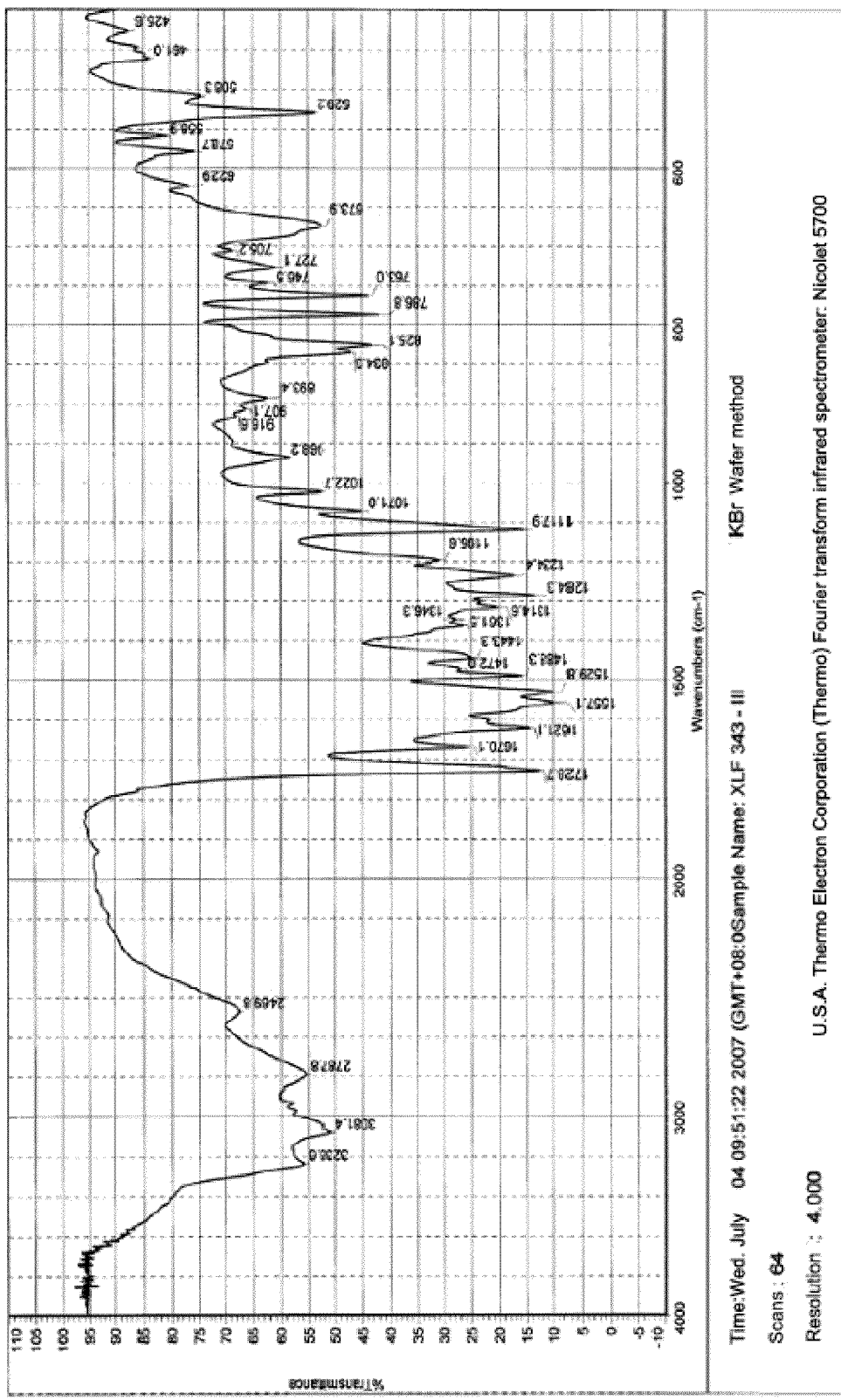

FIG. 14 The infrared absorption spectrum of the crystalline form III sample of XLF-III-43

FIG. 15 The accumulation projection of the crystal unit of crystalline form IV of XLF-III-43

Figure 16:
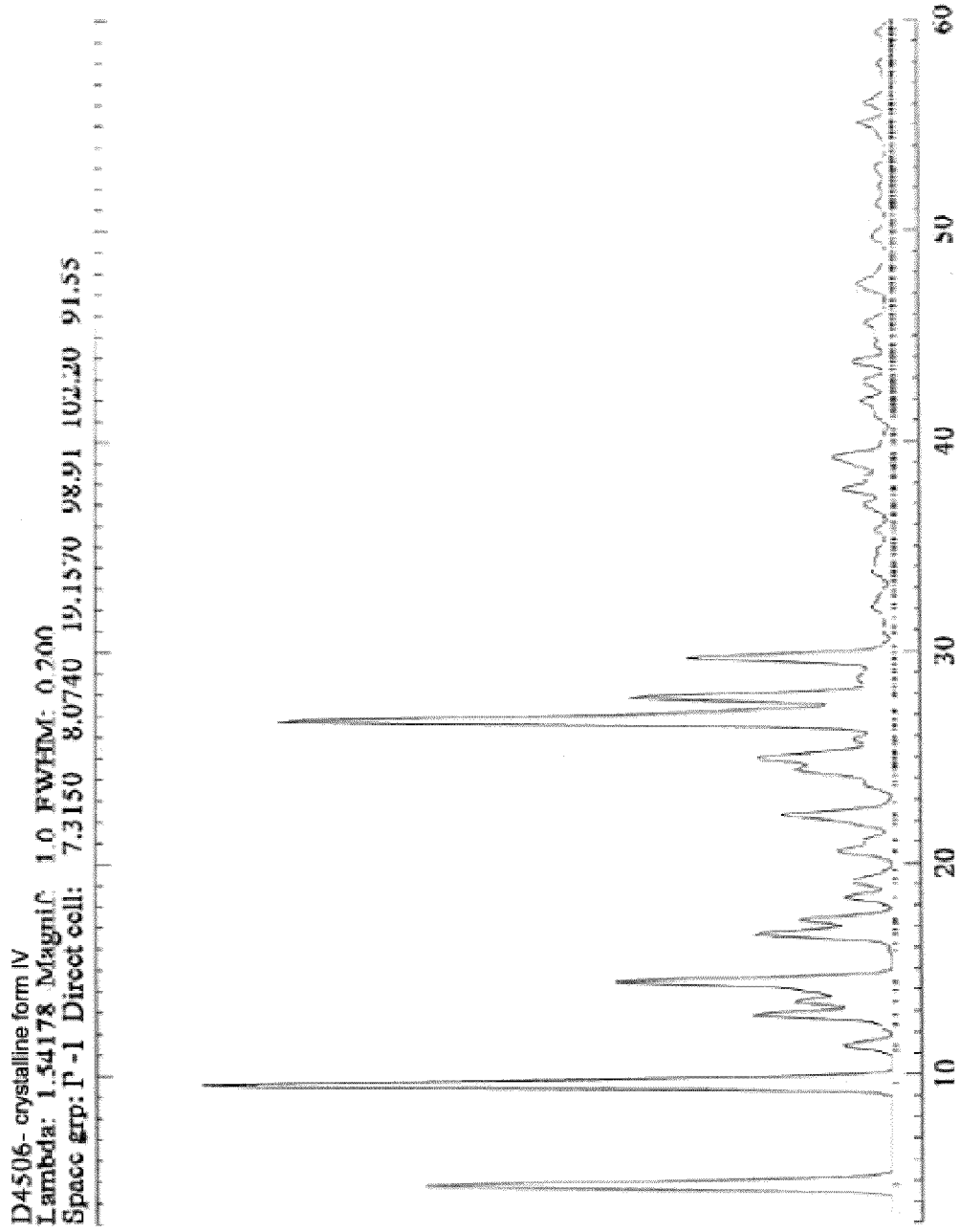

FIG. 16 The X-ray powder diffraction spectrum of crystalline form IV sample of XLF-III-43

Figure 17:
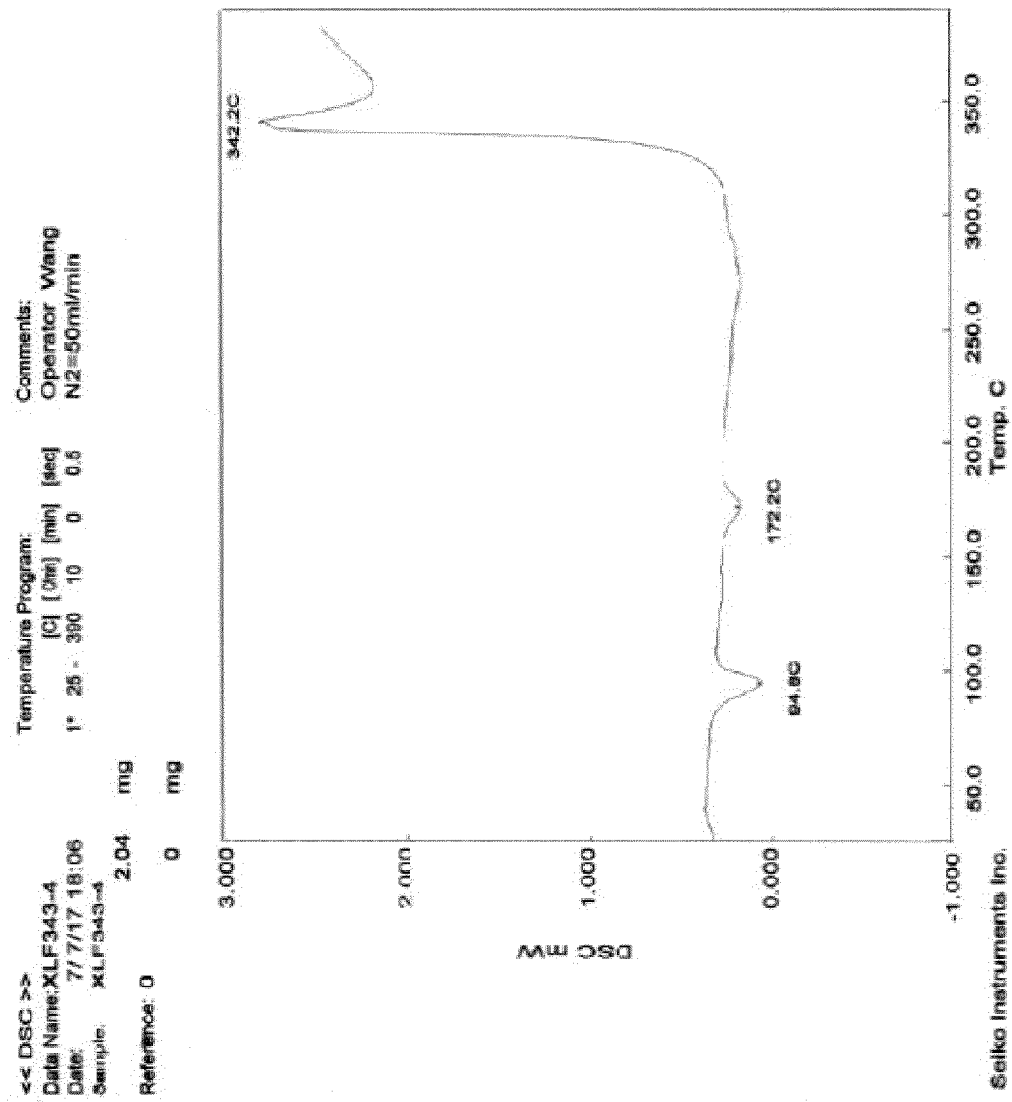

FIG. 17 The DSC spectrum of the crystalline form IV sample of XLF-III-43

Figure 18:
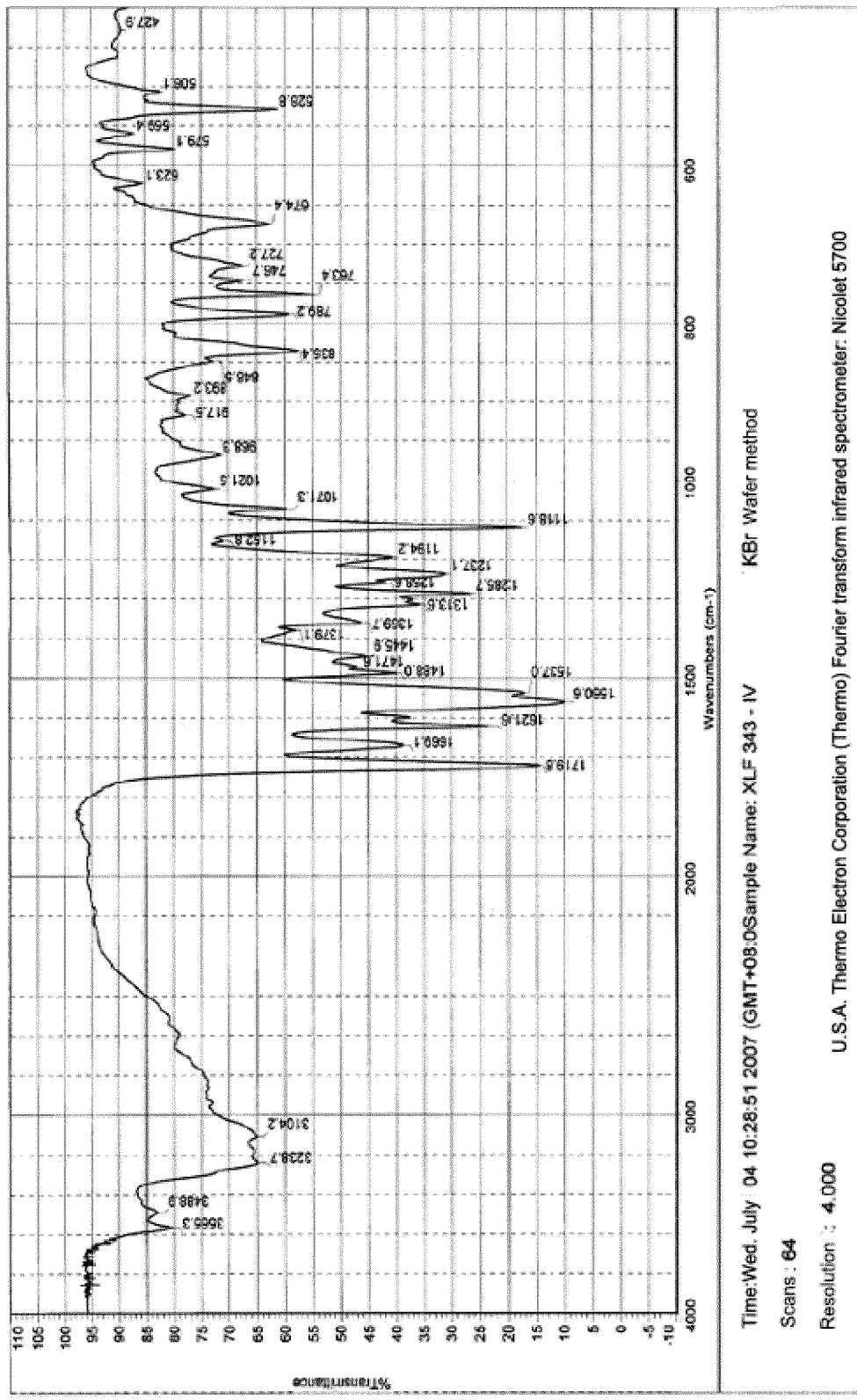

FIG. 18 The infrared absorption spectrum of the crystalline form IV sample of XLF-III-43

Figure 19:
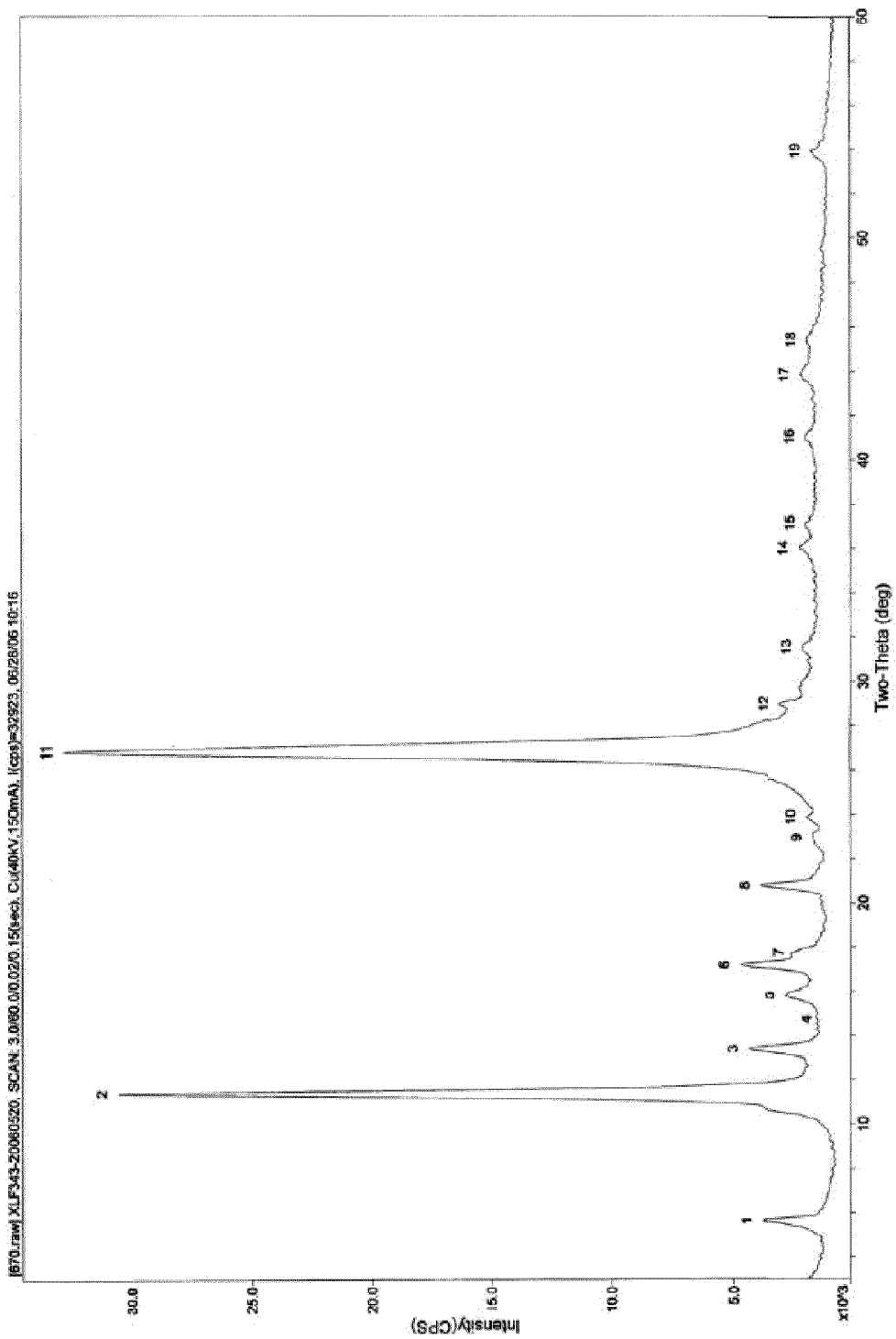

FIG. 19 The X-ray powder diffraction spectrum of crystalline form V sample (amorphous form) of XLF-III-43

Figure 20:
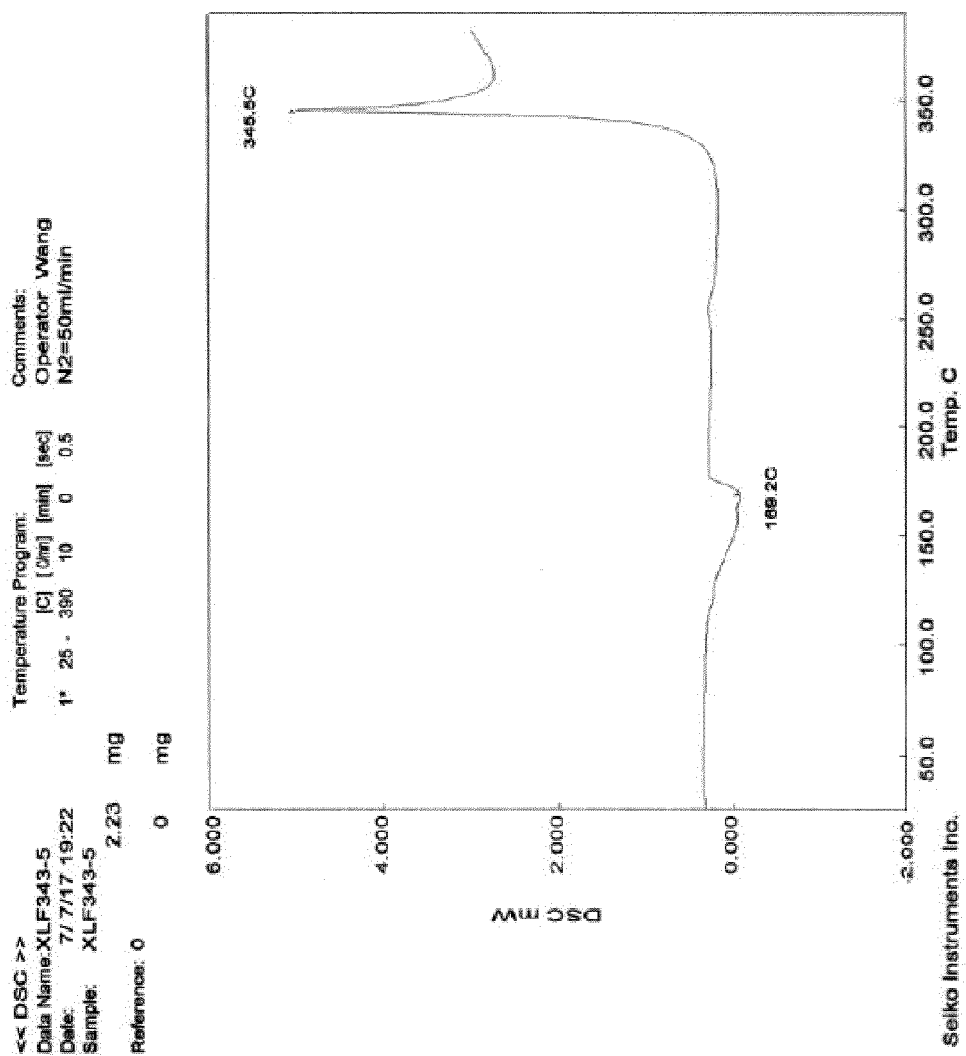

FIG. 20 The DSC spectrum of the crystalline form V sample (amorphous form 1) of XLF-III-43

Figure 21:
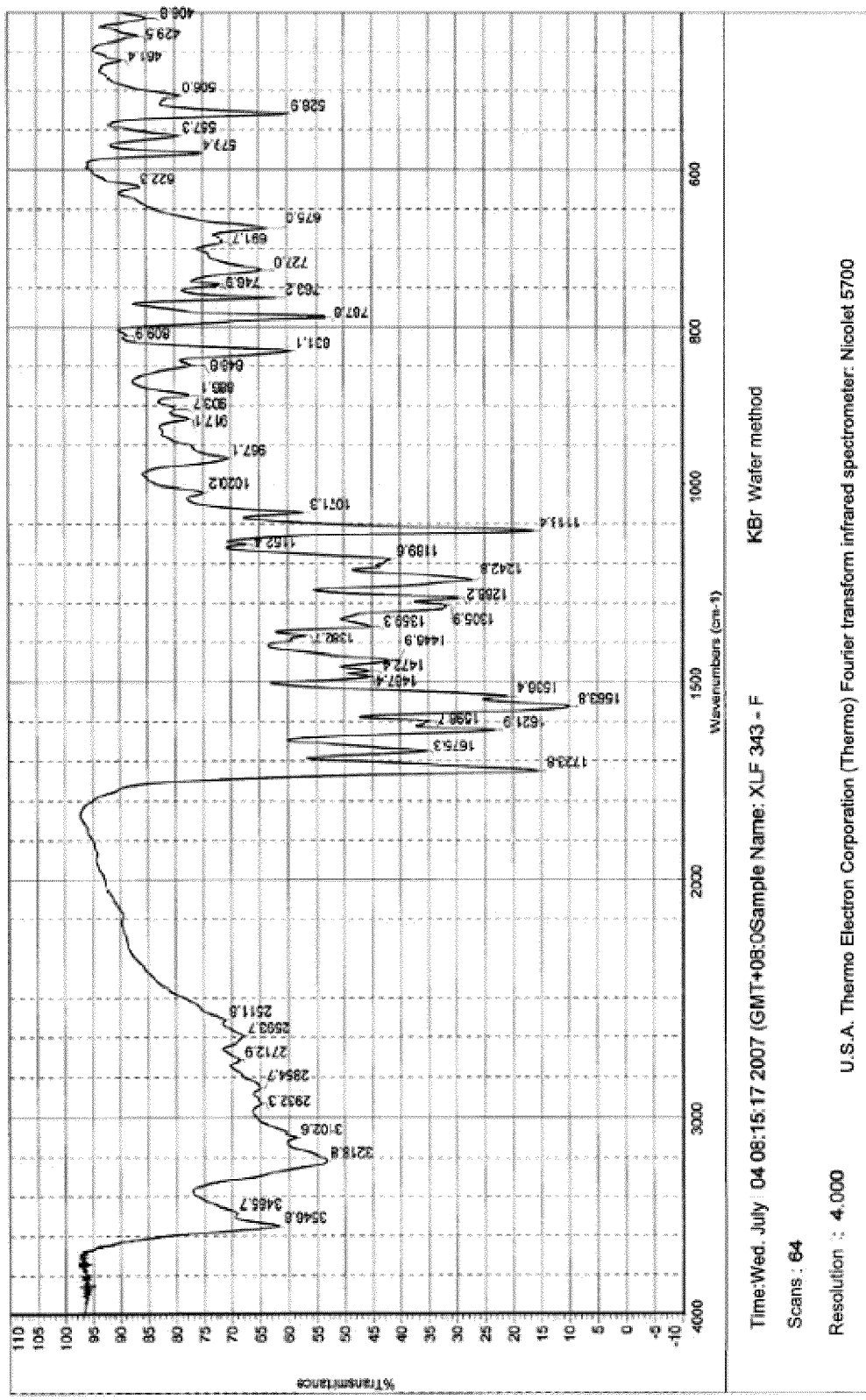

FIG. 21 The infrared absorption spectrum of the crystalline form V sample (amorphous material) of XLF-III-43

Figure 22:
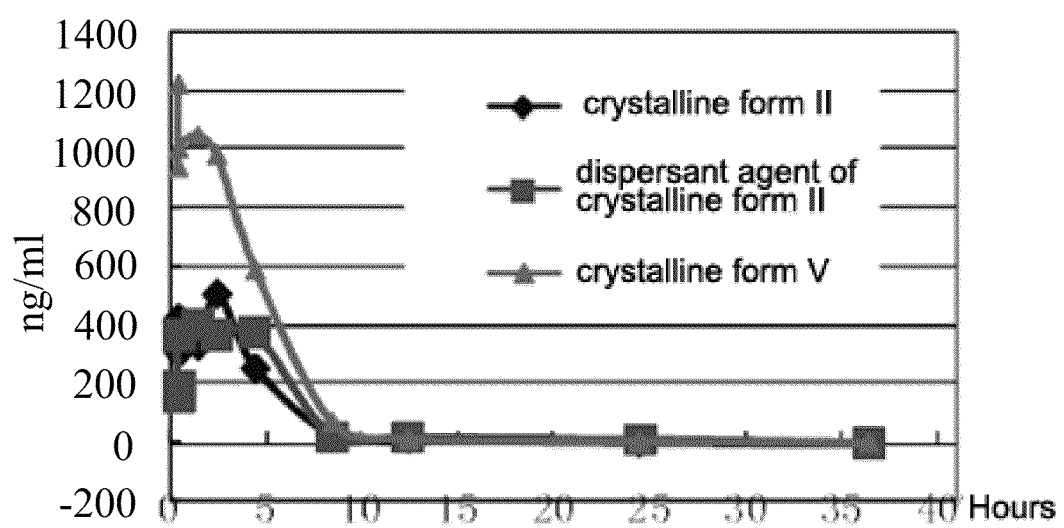

FIG. 22 The analysis of blood drug levels in rats of XLF-III-43 obtained from recrystallization with different solvents.

PRACTICAL PROTOCOLS

In order to illustrate the technical schedules in this invention better, provides these practical examples, but this invention is not restricted by them.

PREPARATION EXAMPLES

Synthesis of the Sample of XLF-III-43:

DMF (35 kg) and (5.2 kg) hydrolytic material were pumped into a 100 L reactor, and stirred the mixture to obtain a solution, and pumped pyridine (1.6 kg) into it. Oxalyl chloride (3.0 kg) was added to the reaction mixture slowly when it was stirred. After added oxalyl chloride to the reaction mixture, continued to stir it for 30 minutes, then 5-aminosalicylic acid (3.2 kg) and pyridine (3.2 kg) were charged in it one by one and stirred it for 5 hours at 50-60° C. After overnight aging, the reaction mixture was filtered and washed by DMF, diluted hydrochloric acid and water. The reaction mass was dried and the crude product (7.5 kg) of XLF-III-43 was obtained.

Refining by Recrystalization

Crude XLF-III-43 (7.5 kg), DMF (106 kg) and charcoal (0.2 kg) were charged in reactor and stirred the reaction mixture for 30 minutes at 150° C. Then the reaction mixture was filtered and the filtered liquid was placed overnight. Then the separated product was filtered, washed and dried. XLF-III-43 (5.3 kg) was obtained and the yielding rate is about 70.7%.

Described below are analytical apparatus used in practical examples and measuring conditions:

Single Crystal X-Ray Diffraction Analysis

Japanese MAC DIP-2030K Face Survey Meter.

Experiment conditions: MoK$_\alpha$ irradiation, graphite monochromator, the distance from crystal to IP board, d=100 mm, tube voltage was 50 kV, tube current was 90 mA, ω scanning, the most 2θ angle was 50°, scanning scope was 0~180°, back panning angle was 5°, interval was 5°, scanning speed was 1.5°/min, 2 times for each image scanning, uptake 36 pictures totally.

Powder X-Ray Diffraction Analysis

Japanese Rigaku D/max-2550 Powder X-Ray Diffractometer.

Experiment conditions: MoK$_\alpha$ irradiation, graphite monochromator, tube voltage was 40 kV, tube current was 150 mA, scanning scope of 2θ was 3-80°, scanning speed was 8°/min, step length was 0.02°, delivering slit DS=1°, receiving slit RS=0.15 mm, scattering slit SS=1°.

Infrared Spectrometer

American Thermoelectricity Company (Thermo), Fourier transformation infrared spectrometer Nicolet 5700.

Experiment condition: KBr sheeting.

Differential Scanning Calorimeter

Japanese Perfect Engineering Company, EXSTAR 6200 differential scanning calorimeter.

Experiment conditions: aluminum crucible, $Al_2O_3$ was used as reference substance, $N_2$=60 ml/min, rising speed of temperature was 10° C./min.

Example 1

The Preparing of the Crystalline Form I Sample of XLF-III-43

Crude XLF-III-43 (36 g) and DMF (540 ml) were charged in a 1 L round bottom flask. The mixture was heated to 150° C. by oil bath. After the crude XLF-III-43 dissolved completely, was put into environment of 72° C., relative humidity, 40%, and kept motionless for 72 hours. Then yellow crystal (26.5) was obtained.

The structure of the obtained crystal was analyzed by X-ray single crystal diffraction, and showed off the symmetry of triclinic system, the space group was P1, and the cell parameters were, a=13.666 Å, b=14.091 Å, c=14.370 Å, α=98.95°, β=116.03°, γ=99.98°.

In obtained crystal, except the molecular of XLF-III-43, $C_{18}H_{12}N_2O_9$, the crystallized solvent molecular of N,N'-dimethyl formamide (DMF, $(CH_3)_2NCHO$) also existed. In crystalline state, there were 4 molecular of XLF-III-43 and 5.5 molecular of DMF in one asymmetric unit. The proportion of the molecular of XLF-III-43 and N,N'-dimethyl formamide was 4.0:5.5. FIG. 1 shows the molecular structure of XLF-III-43. FIG. 2 shows the tereochemical structure projection of the molecular of XLF-III-43. FIG. 3 shows the accumulation projection of the crystal unit of the crystalline sample of XLF-III-43. Table 1 shows the non-hydrogen atomic coordinate parameters. Table 2 shows the bond length values of bonding atoms. Table 3 shows bond angle values of bonding atoms.

When taking X-ray powder diffraction analysis (CuK$_\alpha$ irradiation), the obtained crystal showed off diffraction peak position: 2-Theta values (°) or d values (Å), and relative intensity of diffraction peak: values of peak height (Height %). Table 4 shows the characteristic peak values of the obtained crystal and FIG. 4 shows the spectrum.

In the DSC spectrum of the obtained crystal (FIG. 5), there are a peak of heat absorption with the transition value at about 121° C., and a peak of heat emission with the transition value at about 342° C.

In the infrared absorption spectrum of the obtained crystal of XLF-III-43 (FIG. 6), there are absorption peaks at 3564.6, 3341.8, 3296.2, 3084.9, 2930.4, 1917.2, 1721.1, 1670.8, 1621.7, 1557.0, 1536.1, 1486.8, 1444.4, 1385.3, 1313.6, 1302.0, 1286.3, 1238.7, 1196.5, 1117.8, 1071.4, 1016.6, 965.1, 912.5, 849.9, 830.5, 791.1, 763.7, 746.9, 727.1, 674.7, 620.8, 578.9, 557.7, 527.6, 508.4, 460.0, 436.8 cm$^{-1}$, and the main characteristic absorption peaks of the obtained crystal of XLF-III-43 are the peaks at 3341.8, 3296.2, 2930.4, 1917.2, 1721.1, 1670.8, 1557.0, 1385.3, 1302.2, 1238.7, 1196.5, 912.5, 849.9, 791.1, 620.8, 436.8 cm$^{-1}$.

The spectrum data above shows the crystalline form of the obtained crystal is the crystalline form I of XLF-III-43.

Crude XLF-III-43 (5 g) was added to DMF (75 ml). The mixture was heated to 150° C. by oil bath. After the crude XLF-III-43 dissolved completely by stirring, was put into environment of different temperature and kept motionless for 72 hours. Then the crystal was obtained.

| No. | Temp ° C. | Relative Humidity | Product |
|---|---|---|---|
| 1 | 65 | 35% | yellow crystal |
| 2 | 66 | 35% | yellow crystal |
| 3 | 67 | 35% | yellow crystal |
| 4 | 68 | 35% | yellow crystal |
| 5 | 69 | 35% | yellow crystal |
| 6 | 70 | 35% | yellow crystal |
| 7 | 71 | 35% | yellow crystal |
| 8 | 72 | 35% | yellow crystal |
| 9 | 73 | 35% | yellow crystal |
| 10 | 74 | 35% | yellow crystal |
| 11 | 75 | 35% | yellow crystal |

The obtained crystal was analyzed by X-ray single crystal diffraction, X-ray powder diffraction, infrared spectrum and differential scanning thermometric analysis, and the data show off that it is crystalline form I of XLF-III-43.

Crude XLF-III-43 (5 g) was added to DMF (75 ml). The mixture was heated to 150° C. by oil bath. After the crude XLF-III-43 dissolved completely by stirring, was put into environment of different relative humidity and kept motionless for 72 hours. Then the crystal was obtained.

| No. | Temp ° C. | Relative Humidity | Product |
|---|---|---|---|
| 1 | 72 | 12% | yellow crystal |
| 2 | 72 | 18% | yellow crystal |
| 3 | 72 | 23% | yellow crystal |
| 4 | 72 | 33% | yellow crystal |
| 5 | 72 | 44% | yellow crystal |
| 6 | 72 | 50% | yellow crystal |
| 7 | 72 | 71% | yellow crystal |
| 8 | 72 | 83% | yellow crystal |
| 9 | 72 | 90% | yellow crystal |

The obtained crystal was analyzed by X-ray single crystal diffraction, X-ray powder diffraction, infrared spectrum and differential scanning thermometric analysis, and the data show off that it is crystalline form I of XLF-III-43.

Crude XLF-III-43 was put into different solvents, heated to dissolve, and kept motionless for 72 hours. Then the crystal was obtained.

| No. | Solvents | Temp ° C. | Relative Humidity | Product |
|---|---|---|---|---|
| 1 | DMF:water = 15:1 | 72 | 35% | yellow crystal |
| 2 | DMF:water = 10:1 | 72 | 35% | yellow crystal |
| 3 | DMF:water = 5:1 | 72 | 35% | yellow crystal |
| 4 | DMF:water = 1:1 | 72 | 35% | yellow crystal |
| 5 | DMF:water = 1:2 | 72 | 35% | yellow crystal |
| 6 | DMF:water = 1:3 | 72 | 35% | yellow crystal |
| 7 | DMF:water = 1:4 | 72 | 35% | yellow crystal |

The obtained crystal was analyzed by X-ray single crystal diffraction, X-ray powder diffraction, infrared spectrum and differential scanning thermometric analysis, and the data show off that it is crystalline form I of XLF-III-43.

The preparation of pharmaceutical compositions of crystalline form I of XLF-III-43 (tablet):

As active component, the sterling of the crystalline form I sample of XLF-III-43 was made into pharmaceutical compositions with several excipients. There was 5~60 mg medicine in every tablet. Table 18-1 gives the formulas of these tablets.

TABLE 18-1

The formulas of the tablets of XLF-III-43

| Raw Matirials | Formulations (g/1000 tablets) | | | | | | |
|---|---|---|---|---|---|---|---|
| | Formula 1 | Formula 2 | Formula 3 | Formula 4 | Formula 5 | Formula 6 | Formula 7 |
| Crystalline form I | 5.0 | 10.0 | 20.0 | 30.0 | 40.0 | 50.0 | 60.0 |
| Lactose | 100.0 | 100.0 | 100.0 | 100.0 | 100.0 | 100.0 | 100.0 |
| Starch | 35 | 30 | 20 | 10 | — | — | — |
| Low substituted hydroxypropyl cellulose | 3.0 | 3.0 | 3.0 | 3.0 | 3.0 | 3.0 | 3.0 |
| Microcrystalline cellulose | — | — | — | — | 3.0 | 3.0 | 3.0 |
| Talc | 6.0 | 6.0 | 6.0 | 6.0 | 6.0 | 6.0 | 6.0 |
| Magnesium stearate | 1.0 | 1.0 | 1.0 | 1.0 | 1.0 | 1.0 | 1.0 |
| 1% sodium hydroxymethyl cellulose | q.s | q.s | q.s | q.s | q.s | q.s | q.s |

The preparation method that making the crystalline form I of XLF-III-43, the active component, into pharmaceutical composition: mix crude drug with several excipients, add 1% sodium hydroxymethylcellulose solution to the mixture, make the mixture into soft material, granulate by sifting, dry wet granules, mend granules by sifting, add magnesium stearate and talc powder to the granules and tabletting Example 2

The Preparation of the Crystalline Form II Sample of XLF-III-43

Crude XLF-III-43 (36 g) and DMF (540 ml) was charged in a 1 L round bottom flask of. The mixture was heated to 150° C. by oil bath. After the crude XLF-III-43 dissolved completely, was put into environment of 82° C., relative humidity, 40%, and kept motionless for 48 hours. Then yellow crystal (25.5) was obtained.

The structure of the obtained crystal was analyzed by X-ray single crystal diffraction, and showed off the symmetry of monoclinic system, the space group was $P2_1$, and the cell parameters were, a=7.205 Å, b=32.723 Å, c=8.081 Å, α=90°, β=87.77°, γ=90°

In obtained crystal, except the molecular of XLF-III-43, $C_{18}H_{12}N_2O_9$, the crystallized solvent molecular of dimethylamine $(CH_3)_2NH$ and crystallized water also existed. In crystalline state, there were 2 same molecular of XLF-III-43, 0.5 molecular of dimethylamine and 0.5 molecular of crystallized water in one asymmetric unit. The proportion of the molecular of XLF-III-43, dimethylamine and crystalline water is 2.0:0.5:0.5. FIG. 7 shows the accumulation projection of the crystal unit of the obtained crystal of XLF-III-43. Table 5 shows the non-hydrogen atomic coordinate parameters and the values of equivalent temperature factors of the obtained crystal of XLF-III-43. Table 6 shows the bond length values of bonding atoms of the obtained crystal of XLF-III-43. Table 7 shows bond angle values of bonding atoms of the obtained crystal of XLF-III-43.

When taking X-ray powder diffraction analysis ($CuK_\alpha$ irradiation), the obtained crystal showed off diffraction peak position: 2-Theta values (°) or d values (Å), and relative intensity of diffraction peak: values of peak height (Height %). Table 8 shows the characteristic peak values of the obtained crystal and FIG. 8 shows the spectrum.

In the DSC spectrum of the obtained crystal (FIG. 9), there are two peaks of heat emission with the transition values at about 307° C. and 342° C.

In the infrared absorption spectrum of the obtained crystal of XLF-III-43 (FIG. 10), there are absorption peaks at 3299.0, 3138.1, 3068.8, 2786.8, 2448.4, 1911.8, 1720.0, 1662.8, 1621.6, 1547.9, 1486.1, 1471.4, 1442.0, 1376.1, 1351.7, 1312.4, 1286.3, 1240.5, 1193.4, 1147.4, 1117.4, 1070.7, 1018.8, 965.3, 954.1, 914.9, 850.5, 836.1, 790.2, 762.5, 747.0, 726.1, 716.4, 680.2, 621.7, 580.1, 564.0, 527.0, 508.5, 458.5 $cm^{-1}$, and the main characteristic absorption peaks of the obtained crystal of XLF-III-43 are the peaks at 3299.0, 3138.1, 3068.8, 2786.8, 2448.4, 1911.8, 1720.0, 1662.8, 1547.9, 1376.1, 1351.7, 1240.5, 1193.4, 954.1, 914.9, 836.1, 716.4, 680.2, 564.0, 458.5 $cm^{-1}$.

The spectrum data above shows that obtained crystal is the crystalline form II of XLF-III-43.

Crude XLF-III-43 (5 g) was added to DMF (75 ml). The mixture was heated to 150° C. by oil bath. After the crude XLF-III-43 dissolved completely by stirring, was put into environment of different temperature and kept motionless for 48 hours. Then the crystal was obtained.

| No. | Temp ° C. | Relative Humidity | Product |
|---|---|---|---|
| 1 | 75 | 40% | yellow crystal |
| 2 | 76 | 40% | yellow crystal |
| 3 | 77 | 40% | yellow crystal |
| 4 | 78 | 40% | yellow crystal |
| 5 | 79 | 40% | yellow crystal |
| 6 | 80 | 40% | yellow crystal |
| 7 | 81 | 40% | yellow crystal |
| 8 | 82 | 40% | yellow crystal |
| 9 | 83 | 40% | yellow crystal |

-continued

| No. | Temp ° C. | Relative Humidity | Product |
|---|---|---|---|
| 10 | 84 | 40% | yellow crystal |
| 11 | 85 | 40% | yellow crystal |

The obtained crystal was analyzed by X-ray single crystal diffraction, X-ray powder diffraction, infrared spectrum and differential scanning thermometric analysis, and the data show that it is crystalline form II of XLF-III-43.

Crude XLF-III-43 (5 g) was added to DMF (75 ml). The mixture was heated to 150° C. by oil bath. After the crude XLF-III-43 dissolved completely by stirring, was put into environment of different relative humidity and kept motionless for 48 hours. Then the crystal was obtained.

| No. | Temp ° C. | Relative Humidity | Product |
|---|---|---|---|
| 1 | 82 | 12% | yellow crystal |
| 2 | 82 | 18% | yellow crystal |
| 3 | 82 | 23% | yellow crystal |
| 4 | 82 | 33% | yellow crystal |
| 5 | 82 | 44% | yellow crystal |
| 6 | 82 | 50% | yellow crystal |
| 7 | 82 | 71% | yellow crystal |
| 8 | 82 | 83% | yellow crystal |
| 9 | 82 | 90% | yellow crystal |

The obtained crystal was analyzed by X-ray single crystal diffraction, X-ray powder diffraction, infrared spectrum and differential scanning thermometric analysis, and the data show off that it is crystalline form II of XLF-III-43.

Crude XLF-III-43 was put into different solvents, heated to dissolve, and kept motionless for 48 hours. Then the crystal was obtained.

| No. | Solvents | Temp ° C. | Relative Humidity | Product |
|---|---|---|---|---|
| 1 | DMF:water = 15:1 | 82 | 45% | yellow crystal |
| 2 | DMF:water = 10:1 | 82 | 45% | yellow crystal |
| 3 | DMF:water = 5:1 | 82 | 45% | yellow crystal |
| 4 | DMF:water = 1:1 | 82 | 45% | yellow crystal |
| 5 | DMF:water = 1:2 | 82 | 45% | yellow crystal |
| 6 | DMF:water = 1:3 | 82 | 45% | yellow crystal |
| 7 | DMF:water = 1:4 | 82 | 45% | yellow crystal |

The obtained crystal was analyzed by X-ray single crystal diffraction, X-ray powder diffraction, infrared spectrum and differential scanning thermometric analysis, and the data show off that it is crystalline form II of XLF-III-43.

The preparation of pharmaceutical compositions of crystalline form II of XLF-III-43 (tablet):

As active component, the sterling of the crystalline form II sample of XLF-III-43 was made into pharmaceutical compositions with several excipients. There was 5~60 mg medicine in every tablet. Table 18-2 gives the formulas of these tablets.

TABLE 18-2

The formulas of the tablets of XLF-III-43

| Raw Matirials | Formulations (g/1000 tablets) | | | | | | |
|---|---|---|---|---|---|---|---|
| | Formula 1 | Formula 2 | Formula 3 | Formula 4 | Formula 5 | Formula 6 | Formula 7 |
| Crystalline form II | 5.0 | 10.0 | 20.0 | 30.0 | 40.0 | 50.0 | 60.0 |
| Lactose | 100.0 | 100.0 | 100.0 | 100.0 | 100.0 | 100.0 | 100.0 |
| Starch | 35 | 30 | 20 | 10 | — | — | — |
| Low substituted hydroxypropyl cellulose | 3.0 | 3.0 | 3.0 | 3.0 | 3.0 | 3.0 | 3.0 |
| Microcrystalline cellulose | — | — | — | — | 3.0 | 3.0 | 3.0 |
| Talc | 6.0 | 6.0 | 6.0 | 6.0 | 6.0 | 6.0 | 6.0 |
| Magnesium stearate | 1.0 | 1.0 | 1.0 | 1.0 | 1.0 | 1.0 | 1.0 |
| 1% sodium hydroxymethyl cellulose | q.s | q.s | q.s | q.s | q.s | q.s | q.s |

The preparation method that making the crystalline form II of XLF-III-43, the active component, into pharmaceutical compositions: mix crude drug with several excipients, add 1% sodium hydroxymethylcellulose solution to the mixture, make the mixture into soft material, granulate by sifting, dry wet granules, mend granules by sifting, add magnesium stearate and talc powder to the granules and tabletting Example 3

The Preparation of the Crystalline Form III Sample of XLF-III-43

Crude XLF-III-43 (36 g) and DMF (540 ml) was charged in a 1 L round bottom flask. The mixture was heated to 150° C. by oil bath. After the crude XLF-III-43 dissolved completely, was put into environment of 72° C., relative humidity, 40%, and kept motionless for 5 days. Then yellow crystal (26.7) was obtained.

The structure of the obtained crystal was analyzed by X-ray single crystal diffraction, and showed off the symmetry of triclinic system, the space group is P1, and the cell parameters are, a=7.923 Å, b=10.313 Å, c=12.983 Å, α=90.43°, β=91.73°, γ=72.24°.

In obtained crystal, except the molecular of XLF-III-43, $C_{18}H_{12}N_2O_9$, the crystallized solvent molecular of dimethylamine $((CH_3)_2NH)$ also existed. In crystalline state, the proportion of the molecular of XLF-III-43, and dimethylamine was 2:2 in one asymmetry unit. FIG. 11 shows the accumulation projection of the crystal unit of the obtained crystal of XLF-III-43. Table 9 shows the non-hydrogen atomic coordinate parameters and the values of equivalent temperature factors of the obtained crystal of XLF-III-43. Table 10 shows the bond length values of bonding atoms of the obtained crystal of XLF-III-43. Table 11 shows bond angle values of bonding atoms of the obtained crystal of XLF-III-43.

When taking X-ray powder diffraction analysis ($CuK_\alpha$ irradiation), the obtained crystal showed off diffraction peak position: 2-Theta values (°) or d values (Å), and relative intensity of diffraction peak: values of peak height (Height %). Table 12 shows the characteristic peak values of the obtained crystal and FIG. 12 shows the spectrum.

In the DSC spectrum of the obtained crystal (FIG. 13), there are a peak of heat absorption with the transition value at about 191° C., and a peak of heat emission with the transition values at 293.5° C.

In the infrared absorption spectrum of the obtained crystal of XLF-III-43 (FIG. 14), there are absorption peaks at 3238.6, 3081.4, 2787.8, 2469.8, 1728.7, 1670.1, 1621.1, 1557.1, 1529.8, 1488.3, 1472.0, 1443.3, 1361.5, 1346.3, 1314.6, 1284.3, 1234.4, 1195.6, 1117.9, 1071.0, 1022.7, 968.2, 916.6, 907.1, 893.4, 834.3, 825.1, 786.8, 763.0, 746.5, 727.1, 705.2, 673.9, 622.9, 578.7, 558.9, 529.2, 508.3, 461.0, 425.6 cm$^{-1}$, and the main characteristic absorption peaks of the obtained crystal of XLF-III-43 are the peaks at 3299.0, 3138.1, 3068.8, 2786.8, 2448.4, 1911.8, 1720.0, 1662.8, 1547.9, 1376.1, 1351.7, 1240.5, 1193.4, 954.1, 914.9, 836.1, 716.4, 680.2, 564.0, 458.5 cm$^{-1}$.

The spectrum data above shows the obtained crystal is the crystalline form III of XLF-III-43.

Crude XLF-III-43 (5 g) was added to DMF (75 ml). The mixture was heated to 150° C. by oil bath. After the crude XLF-III-43 dissolved completely by stirring, was put into environment of different temperature and kept motionless for 5 days. Then the crystal was obtained.

| No. | Temp ° C. | Relative Humidity | Product |
|---|---|---|---|
| 1 | 65 | 35% | yellow crystal |
| 2 | 66 | 35% | yellow crystal |
| 3 | 67 | 35% | yellow crystal |
| 4 | 68 | 35% | yellow crystal |
| 5 | 69 | 35% | yellow crystal |
| 6 | 70 | 35% | yellow crystal |
| 7 | 71 | 35% | yellow crystal |
| 8 | 72 | 35% | yellow crystal |
| 9 | 73 | 35% | yellow crystal |
| 10 | 74 | 35% | yellow crystal |
| 11 | 75 | 35% | yellow crystal |

The obtained crystal was analyzed by X-ray single crystal diffraction, X-ray powder diffraction, infrared spectrum and differential scanning thermometric analysis, and the data show off that it is crystalline form III of XLF-III-43.

Crude XLF-III-43 (5 g) was added to DMF (75 ml). The mixture was heated to 150° C. by oil bath. After the crude XLF-III-43 dissolved completely by stirring, was put into environment of different relative humidity and kept motionless for 5 days. Then the crystal was obtained.

| No. | Temp ° C. | Relative Humidity | Product |
|---|---|---|---|
| 1 | 72 | 12% | yellow crystal |
| 2 | 72 | 18% | yellow crystal |
| 3 | 72 | 23% | yellow crystal |
| 4 | 72 | 33% | yellow crystal |
| 5 | 72 | 44% | yellow crystal |
| 6 | 72 | 50% | yellow crystal |
| 7 | 72 | 71% | yellow crystal |
| 8 | 72 | 83% | yellow crystal |
| 9 | 72 | 90% | yellow crystal |

The obtained crystal was analyzed by X-ray single crystal diffraction, X-ray powder diffraction, infrared spectrum and differential scanning thermometric analysis, and the data show off that it is crystalline form III of XLF-III-43.

Crude XLF-III-43 was put into different solvents, heated to dissolve, and kept motionless for 5 days. Then the crystal was obtained.

| No. | Solvents | Temp ° C. | Relative Humidity | Product |
|---|---|---|---|---|
| 1 | DMF:water = 15:1 | 72 | 35% | yellow crystal |
| 2 | DMF:water = 10:1 | 72 | 35% | yellow crystal |
| 3 | DMF:water = 5:1 | 72 | 35% | yellow crystal |
| 4 | DMF:water = 1:1 | 72 | 35% | yellow crystal |
| 5 | DMF:water = 1:2 | 72 | 35% | yellow crystal |
| 6 | DMF:water = 1:3 | 72 | 35% | yellow crystal |
| 7 | DMF:water = 1:4 | 72 | 35% | yellow crystal |

The obtained crystal was analyzed by X-ray single crystal diffraction, X-ray powder diffraction, infrared spectrum and differential scanning thermometric analysis, and the data show off that it is crystalline form III of XLF-III-43.

The preparing of pharmaceutical compositions of crystalline form III of XLF-III-43 (tablet):

As active component, the sterling of the crystalline form III sample of XLF-III-43 was made into pharmaceutical compositions with several excipients. There was 5~60 mg medicine in every tablet. Table 18-3 gives the formulas of these tablets.

TABLE 18-3

The formulas of the tablets of XLF-III-43

| Raw Material | Formulations (g/1000 tablets) | | | | | | |
|---|---|---|---|---|---|---|---|
| | Formula 1 | Formula 2 | Formula 3 | Formula 4 | Formula 5 | Formula 6 | Formula 7 |
| Crystalline form III | 5.0 | 10.0 | 20.0 | 30.0 | 40.0 | 50.0 | 60.0 |
| Lactose | 100.0 | 100.0 | 100.0 | 100.0 | 100.0 | 100.0 | 100.0 |
| Starch | 35 | 30 | 20 | 10 | — | — | — |
| Low substituted hydroxypropyl cellulose | 3.0 | 3.0 | 3.0 | 3.0 | 3.0 | 3.0 | 3.0 |
| Microcrystalline cellulose | — | — | — | — | 3.0 | 3.0 | 3.0 |
| Talc | 6.0 | 6.0 | 6.0 | 6.0 | 6.0 | 6.0 | 6.0 |
| Magnesium stearate | 1.0 | 1.0 | 1.0 | 1.0 | 1.0 | 1.0 | 1.0 |
| 1% sodium hydroxymethyl cellulose | q.s | q.s | q.s | q.s | q.s | q.s | q.s |

The preparation method that making the crystalline form III of XLF-III-43, the active component, into pharmaceutical compositions: mix crude drug with several excipients, add 1% sodium hydroxymethylcellulose solution to the mixture, make the mixture into soft material, granulate by sifting, dry wet granules, mend granules by sifting, add magnesium stearate and talc powder to the granules and tabletting.

Example 4

The Preparation of Crystalline Form IV Sample of XLF-III-43

Crude XLF-III-43 (36 g) and DMF (540 ml) was charged in 1 L round bottom flask. The mixture was heated to 150° C. by oil bath. After the crude XLF-III-43 dissolved completely, was put into environment of 82° C., relative humidity, 40%, and kept motionless for 3 days. Then yellow crystal (25.3) was obtained.

The structure of the obtained crystal was analyzed by single X-ray diffraction, and showed off the symmetry of triclinic system, the space group is P-1, and the cell parameters are, a=7.315 Å, b=8.074 Å, c=19.157 Å, α=98.91°, β=102.20°, γ=91.55°.

In obtained crystal, except the molecular of XLF-III-43, $C_{18}H_{12}N_2O_9$, the crystallized solvent molecular of N,N'-dimethyl formamide (DMF, $(CH_3)_2NCHO$) also existed. In crystalline state, the proportion of the molecular of XLF-III-43, and DMF was 1:1 in one asymmetry unit. FIG. 15 shows the accumulation projection of the crystal unit of the obtained crystal of XLF-III-43. Table 13 shows the non-hydrogen atomic coordinate parameters and the values of equivalent temperature factors of the obtained crystal of XLF-III-43. Table 14 shows the bond length values of bonding atoms of the obtained crystal of XLF-III-43. Table 15 shows bond angle values of bonding atoms of the obtained crystal of XLF-III-43.

When taking powder X-ray diffraction analysis ($CuK_\alpha$ irradiation), the obtained crystal showed off diffraction peak position: 2-Theta values (°) or d values (Å), and relative intensity of diffraction peak: values of peak height (Height %). Table 16 shows the characteristic peak values of the obtained crystal and FIG. 16 shows the spectrum.

In the DSC spectrum of the obtained crystal (FIG. 17), there are two peaks of heat absorption with the transition value at about 94° C. and 172° C., and a peak of heat emission with the transition value at 342° C.

In the infrared absorption spectrum of the obtained crystal of XLF-III-43 (FIG. 18), there are absorption peaks at 3565.3, 3488.9, 3238.7, 3104.2, 1719.8, 1669.1, 1621.6, 1560.6, 1537.0, 1488.0, 1471.6, 1445.9, 1379.1, 1359.7, 1313.6, 1285.7, 1258.6, 1152.8, 1237.1, 1194.2, 1118.6, 1071.3, 1021.5, 968.3, 917.5, 893.2, 848.5, 835.4, 789.2, 763.4, 746.7, 727.2, 674.4, 623.1, 579.1, 559.4, 528.8, 506.1, 427.9 cm$^{-1}$, and the main characteristic absorption peaks of the obtained crystal of XLF-III-43 are the peaks at 3565.3, 3488.9, 3238.7, 1719.8, 1669.1, 1560.6, 1379.1, 1258.6, 1237.1, 1194.2, 835.4, 427.9 cm$^{-1}$.

The spectrum data above shows the obtained crystal is the crystalline form IV of XLF-III-43.

Crude XLF-III-43 (5 g) was added to DMF (75 ml). The mixture was heated to 150° C. by oil bath. After the crude XLF-III-43 dissolved completely by stirring, was put into environment of different temperature and kept motionless for 72 hours. Then the crystal was obtained.

| No. | Temp ° C. | Relative Humidity | Product |
|---|---|---|---|
| 1 | 75 | 40% | yellow crystal |
| 2 | 76 | 40% | yellow crystal |
| 3 | 77 | 40% | yellow crystal |
| 4 | 78 | 40% | yellow crystal |
| 5 | 79 | 40% | yellow crystal |
| 6 | 80 | 40% | yellow crystal |
| 7 | 81 | 40% | yellow crystal |
| 8 | 82 | 40% | yellow crystal |
| 9 | 83 | 40% | yellow crystal |
| 10 | 84 | 40% | yellow crystal |
| 11 | 85 | 40% | yellow crystal |

The obtained crystal was analyzed by X-ray single crystal diffraction, X-ray powder diffraction, infrared spectrum and differential scanning thermometric analysis, and the data show off that it is crystalline form IV of XLF-III-43.

Crude XLF-III-43 (5 g) was added to DMF (75 ml). The mixture was heated to 150° C. by oil bath. After the crude XLF-III-43 dissolved completely by stirring, was put into environment of different relative humidity and kept motionless for 72 hours. Then the crystal was obtained.

| No. | Temp ° C. | Relative Humidity | Product |
|---|---|---|---|
| 1 | 82 | 12% | yellow crystal |
| 2 | 82 | 18% | yellow crystal |
| 3 | 82 | 23% | yellow crystal |
| 4 | 82 | 33% | yellow crystal |
| 5 | 82 | 44% | yellow crystal |
| 6 | 82 | 50% | yellow crystal |
| 7 | 82 | 71% | yellow crystal |
| 8 | 82 | 83% | yellow crystal |
| 9 | 82 | 90% | yellow crystal |

The obtained crystal was analyzed by X-ray single crystal diffraction, X-ray powder diffraction, infrared spectrum and differential scanning thermometric analysis, and the data show off that it is crystalline form IV of XLF-III-43.

Crude XLF-III-43 was put into different solvents, heated to dissolve, and kept motionless for 72 hours. Then the crystal was obtained.

| No. | Solvents | Temp ° C. | Relative Humidity | Product |
|---|---|---|---|---|
| 1 | DMF:water = 15:1 | 82 | 45% | yellow crystal |
| 2 | DMF:water = 10:1 | 82 | 45% | yellow crystal |
| 3 | DMF:water = 5:1 | 82 | 45% | yellow crystal |
| 4 | DMF:water = 1:1 | 82 | 45% | yellow crystal |
| 5 | DMF:water = 1:2 | 82 | 45% | yellow crystal |
| 6 | DMF:water = 1:3 | 82 | 45% | yellow crystal |
| 7 | DMF:water = 1:4 | 82 | 45% | yellow crystal |

The obtained crystal was analyzed by X-ray single crystal diffraction, X-ray powder diffraction, infrared spectrum and differential scanning thermometric analysis, and the data show off that it is crystalline form IV of XLF-III-43.

The preparations of pharmaceutical compositions of crystalline form IV of XLF-III-43 (tablet):

As active component, the sterling of the crystalline form IV sample of XLF-III-43 was made into pharmaceutical compositions with several excipients. There was 5~60 mg medicine in every tablet. Table 18-4 gives the formulas of these tablets.

TABLE 18-4

The formulas of the tablets of XLF-III-43

| Raw Materials | Formulations (g/1000 tablets) | | | | | | |
|---|---|---|---|---|---|---|---|
| | Formula 1 | Formula 2 | Formula 3 | Formula 4 | Formula 5 | Formula 6 | Formula 7 |
| Crystalline form IV | 5.0 | 10.0 | 20.0 | 30.0 | 40.0 | 50.0 | 60.0 |
| Lactose | 100.0 | 100.0 | 100.0 | 100.0 | 100.0 | 100.0 | 100.0 |
| Starch | 35 | 30 | 20 | 10 | — | — | — |
| Low substituted hydroxypropyl cellulose | 3.0 | 3.0 | 3.0 | 3.0 | 3.0 | 3.0 | 3.0 |
| Microcrystalline cellulose | — | — | — | — | 3.0 | 3.0 | 3.0 |
| Talc | 6.0 | 6.0 | 6.0 | 6.0 | 6.0 | 6.0 | 6.0 |
| Magnesium stearate | 1.0 | 1.0 | 1.0 | 1.0 | 1.0 | 1.0 | 1.0 |
| 1% sodium hydroxymethyl cellulose | q.s | q.s | q.s | q.s | q.s | q.s | q.s |

The preparation method that making the crystalline form IV of XLF-III-43, the active component, into pharmaceutical composition: mix crude drug with several excipients, add 1% sodium hydroxymethylcellulose solution to the mixture, make the mixture into soft material, granulate by sifting, dry wet granules, mend granules by sifting, add magnesium stearate and talc powder to the granules and tabletting Example 5

The Preparation of the Crystalline Form V Sample of XLF-III-43

Step a: crude XLF-III-43 (36 g) and DMF (540 ml) was charged in 1 L round bottom flask. The mixture was heated to 150° C. by oil bath. After the crude XLF-III-43 dissolved completely, was put into environment of 82° C., relative humidity, 40%, and kept motionless for 48 hours. Then yellow crystal (25.5) was obtained.

Step b: the yellow crystal (25 g) above and 0.2N HCl (500 ml) were charged in flask of 1 liter with three orifices, and stirred for 48 hours at 50° C. Then the reaction mixture was filtered, washed with 150 ml water, pumped, dried for 12 hours under vacuum at 80° C. The amorphous crude drug was obtained and the yielding rate was 92%.

When taking powder X-ray diffraction analysis (CuK$_\alpha$ irradiation), the obtained amorphous solid substance showed off diffraction peak position: 2-Theta values (°) or d values (Å), and relative intensity of diffraction peak: values of peak height (Height %). Table 17 shows the characteristic peak values of the obtained crystal and FIG. 19 shows the spectrum. There was only one molecular of associated water but not other solvent molecular in thy amorphous solid substance.

In the DSC spectrum of the obtained amorphous solid substance (FIG. 20), there are a peak of heat absorption with the transition value at about 169° C., and a peak of heat emission with the transition value at 345° C.

In the infrared absorption spectrum of the obtained amorphous solid substance (FIG. 21), there are absorption peaks at 3565.3, 3488.9, 3238.7, 3104.2, 1719.8, 1669.1, 1621.6, 1560.6, 1537.0, 1488.0, 1471.6, 1445.9, 1379.1, 1359.7, 1313.6, 1285.7, 1258.6, 1152.8, 1237.1, 1194.2, 1118.6, 1071.3, 1021.5, 968.3, 917.5, 893.2, 848.5, 835.4, 789.2, 763.4, 746.7, 727.2, 674.4, 623.1, 579.1, 559.4, 528.8, 506.1, 427.9 cm$^{-1}$, and the main characteristic absorption peaks of the obtained amorphous solid substance are the peaks at 3565.3, 3488.9, 3238.7, 1719.8, 1669.1, 1560.6, 1379.1, 1258.6, 1237.1, 1194.2, 835.4, 427.9 cm$^{-1}$.

The spectrum data above shows the acquired amorphous solid substance is crystalline form V of XLF-III-43 (amorphous form).

In step b, the yellow crystal (25 g) and 0.2N HCl (500 ml) were charged in a 1 L flask with three orifices, and stirred for 48 hours under different temperatures. Then the reaction mixture was filtered, washed with 150 ml water, pumped, dried for 12 hours under vacuum at 80° C. The amorphous crude drug was obtained.

| No. | Temp ° C. | Relative Humidity | Product |
|---|---|---|---|
| 1 | 40 | 40% | amorphous yellow powder |
| 2 | 45 | 40% | amorphous yellow powder |
| 3 | 55 | 40% | amorphous yellow powder |
| 4 | 60 | 40% | amorphous yellow powder |
| 5 | 65 | 40% | amorphous yellow powder |
| 6 | 70 | 40% | amorphous yellow powder |
| 7 | 75 | 40% | amorphous yellow powder |
| 8 | 80 | 40% | amorphous yellow powder |
| 9 | 85 | 40% | amorphous yellow powder |

The acquired amorphous solid substance was analyzed by single crystal X-ray diffraction, powder X-ray diffraction, infrared spectrum and differential scanning thermometric analysis, and the data show off that it is crystalline form V of XLF-III-43.

In step b, the yellow crystal (25 g) and different concentrations of HCl (500 ml) were charged in a 1 L flask with three orifices, and stirred for 48 hours at 82° C. Then the reaction mixture was filtered, washed with 150 ml water, pumped, dried for 12 hours under vacuum at 80° C. The amorphous crude drug was obtained.

| No. | Concentration of HCl | Relative Humidity | Product |
|---|---|---|---|
| 1 | 0.1N | 40% | amorphous yellow powder |
| 2 | 0.2N | 40% | amorphous yellow powder |
| 3 | 0.3N | 40% | amorphous yellow powder |
| 4 | 0.4N | 40% | amorphous yellow powder |
| 5 | 0.5N | 40% | amorphous yellow powder |
| 6 | 0.6N | 40% | amorphous yellow powder |

-continued

| No. | Concentration of HCl | Relative Humidity | Product |
|---|---|---|---|
| 7 | 0.7N | 40% | amorphous yellow powder |
| 8 | 0.8N | 40% | amorphous yellow powder |

The obtained amorphous solid substance was analyzed by X-ray single crystal diffraction, X-ray powder diffraction, infrared spectrum and differential scanning thermometric analysis, and the data show off that it is crystalline form V of XLF-III-43.

In step a, XLF-III-43 was put into different solvents, heated to dissolve, and kept motionless for 48 hours. Then the crystal was obtained.

| No. | Solvents | Temp ° C. | Relative Humidity | Product |
|---|---|---|---|---|
| 1 | DMF:water = 15:1 | 82 | 45% | yellow crystal |
| 2 | DMF:water = 10:1 | 82 | 45% | yellow crystal |
| 3 | DMF:water = 5:1 | 82 | 45% | yellow crystal |
| 4 | DMF:water = 1:1 | 82 | 45% | yellow crystal |
| 5 | DMF:water = 1:2 | 82 | 45% | yellow crystal |
| 6 | DMF:water = 1:3 | 82 | 45% | yellow crystal |
| 7 | DMF:water = 1:4 | 82 | 45% | yellow crystal |

In step b, the yellow crystal (5 g) and different concentrations of HCl (100 ml) were charged in flask of 500 ml with three orifices, and stirred for 48 hours at 82° C. Then the reaction mixture was filtered, washed with 150 ml water, pumped, dried for 12 hours under vacuum at 80° C. The amorphous yellow powder was obtained.

The obtained amorphous solid substance was analyzed by X-ray single crystal diffraction, X-ray powder diffraction, infrared spectrum and differential scanning thermometric analysis, and the data show off that it is crystalline form V of XLF-III-43.

The preparations of pharmaceutical compositions of crystalline form V of XLF-III-43 (tablet):

As active component, the sterling of the crystalline form V sample of XLF-III-43 was made into pharmaceutical compositions with several excipients. There was 5~60 mg medicine in every tablet. Table 18-5 gives the formulas of these tablets.

The preparation method that making the crystalline form V of XLF-III-43, the active component, into pharmaceutical compositions: mix crude drug with several excipients, add 1% sodium hydroxymethylcellulose solution to the mixture, make the mixture into soft material, granulate by sifting, dry wet granules, mend granules by sifting, add magnesium stearate and talc powder to the granules and tabletting

Example 6

The Preparation of the Mixed Crystal Solid Samples of the Five Crystalline Forms of XLF-III-43 with Different Proportions 6.1 Preparation methods of mixed crystal solid samples of the crystalline form I, II, III, IV, V of XLF-III-43 with weight proportion 1:1:1:1:1.

Weighed the samples of the crystalline form I, II, III, IV, V of XLF-III-43, 10 grams respectively, put them into well closed container with opening, sealed up the container, shook these solid substances and made them mixed completely, then obtained the mixed crystal of the crystalline form I, II, III, IV, V of XLF-III-43 with weight proportion 1:1:1:1:1.

| Proportion by weight | Crystalline forms of XLF-III-43 | | | | |
|---|---|---|---|---|---|
| | I | II | III | IV | V |
| 6.2 | 0 | 1 | 1 | 1 | 2 |
| 6.3 | 0 | 1 | 1 | 2 | 1 |
| 6.4 | 1 | 0 | 2 | 1 | 1 |
| 6.5 | 2 | 0 | 1 | 0 | 2 |
| 6.6 | 1 | 2 | 0 | 2 | 0 |
| 6.7 | 2 | 0 | 0 | 0 | 3 |
| 6.8 | 1 | 2 | 2 | 0 | 0 |
| 6.9 | 1 | 1 | 1 | 0 | 2 |
| 6.10 | 1 | 1 | 1 | 2 | 0 |

According to the table above, weighed the samples of the crystalline form I, II, III, IV, V of XLF-III-43, 10 grams per weight part, put them into well closed container with opening, sealed up the container, shook these solid substances and made them mixed completely, then obtained several groups of mixed crystals of XLF-III-43.

The preparation methods of the mixed crystal pharmaceutics of XLF-III-43 (tablet): As active component, the mixed crystals of XLF-III-43 obtained from 6.2, 6.5 and 6.7, was made into tablets, 5~60 mg medicine in every tablet. Table 18-6 gives the formulas of these tablets.

TABLE 18-5

The formulas of the tablets of XLF-III-43

| Raw Materials | Formulations (g/1000 tablets) | | | | | | |
|---|---|---|---|---|---|---|---|
| | Formula 1 | Formula 2 | Formula 3 | Formula 4 | Formula 5 | Formula 6 | Formula 7 |
| Crystalline form V | 5.0 | 10.0 | 20.0 | 30.0 | 40.0 | 50.0 | 60.0 |
| Lactose | 100.0 | 100.0 | 100.0 | 100.0 | 100.0 | 100.0 | 100.0 |
| Starch | 35 | 30 | 20 | 10 | — | — | — |
| Low substituted hydroxypropyl cellulose | 3.0 | 3.0 | 3.0 | 3.0 | 3.0 | 3.0 | 3.0 |
| Microcrystalline cellulose | — | — | — | — | 3.0 | 3.0 | 3.0 |
| Talc | 6.0 | 6.0 | 6.0 | 6.0 | 6.0 | 6.0 | 6.0 |
| Magnesium stearate | 1.0 | 1.0 | 1.0 | 1.0 | 1.0 | 1.0 | 1.0 |
| 1% sodium hydroxymethyl cellulose | q.s | q.s | q.s | q.s | q.s | q.s | q.s |

TABLE 18-6

The formulas of the tablets of XLF-III-43

| Raw Materials | Formulations (g/1000 tablets) | | | | | | |
|---|---|---|---|---|---|---|---|
| | Formula 1 | Formula 2 | Formula 3 | Formula 4 | Formula 5 | Formula 6 | Formula 7 |
| XLF-III-43 | 5.0 | 10.0 | 20.0 | 30.0 | 40.0 | 50.0 | 60.0 |
| Lactose | 100.0 | 100.0 | 100.0 | 100.0 | 100.0 | 100.0 | 100.0 |
| Starch | 35 | 30 | 20 | 10 | — | — | — |
| Low substituted hydroxypropyl cellulose | 3.0 | 3.0 | 3.0 | 3.0 | 3.0 | 3.0 | 3.0 |
| Microcrystalline cellulose | — | — | — | — | 3.0 | 3.0 | 3.0 |
| Talc | 6.0 | 6.0 | 6.0 | 6.0 | 6.0 | 6.0 | 6.0 |
| Magnesium stearate | 1.0 | 1.0 | 1.0 | 1.0 | 1.0 | 1.0 | 1.0 |
| 1% sodium hydroxymethyl cellulose | q.s | q.s | q.s | q.s | q.s | q.s | q.s |

The preparation method that making the mixed crystals of XLF-III-43, the active component, into pharmaceutical compositions: mix crude drug with several excipients, add 1% sodium hydroxymethylcellulose solution to the mixture, make the mixture into soft material, granulate by sifting, dry wet granules, mend granules by sifting, add magnesium stearate and talc powder to the granules and tabletting Practical Example 7

Influences of Different Crystalline Forms on Blood Drug Levels in Rats

1. Crystal Samples: crystalline form II and V of XLF-III-43, dispersant agent of crystalline form II (obtained by comminuting crystalline form II and V of XLF-III-43).
2. Methodology study of detecting blood drug level
(1) Experimental Conditions:
Instrument:
HPLC: waters 2690 chromatography system, 2487 UV detector, Milnicousamidem 32 chromatography management system. Column: 4.6×250 mm Spherisorb C18 5 μm; flow rate: 1.0 ml/min; column temperature: 25° C.; detection wavelength: 330 nm. After treated by solid phase extraction, plasma samples were directly injected and analyzed.
(2) Specificity study: the experiment results showed that, endogenous substances and metabolites in the blood did not interfere with the analysis.
(3) Standard curve and linear range: within concentration range 5-200 ng/ml, XLF-III-43 showed a good linear relationship (correlation coefficient, r=0.9999).
(4) Recovery experiment: extraction recoveries (greater than 75%) meet the requests that SFDA issued on methods of pharmacokinetic study.
(5) Sensitivity: minimum detectable amount was 2 ng/ml, the minimum limit of quantification was 5 ng/ml.
3. Pharmacokinetic study
The results of preliminary pharmacokinetic of crystalline forms and amorphous form of XLF-III-43 indicated that (FIG. 22), after one-time orally administered of XLF-III-43 at 30 mg/kg, the maximum plasma concentration Cmax was 2 μg/ml, peak time (Tmax) was 0.5 hour, and half-life could be detected within 36 hours, but could not be detected at 48 h. Within a certain period of time, crystalline form V of XLF-III-43 obtained higher blood concentration than crystalline form II of XLF-III-43. There was not significant difference between the plasma concentration of crystalline form II of XLF-III-43 and the dispersant agent of crystalline form II of XLF-III-43. Example 8

Effects of Different Crystalline Forms of XLF-III-43 on Acute Renal Function Injury in Mice Induced by Cisplatin Objective: To observe the effects of different crystal forms of XLF-III-43 on acute renal function injury in mice induced by Cisplatin Materials:
Reagents: crystalline form I, II and V of XLF-III-43, all were prepared into suspensions with 0.5% sodium carboxymethylcellulose. Positive control: Losartan potassium, ATIRA Hangzhou Merck Sharp & Dohme Pharmaceutics Company, lot number: S1241. Crude drug of Cisplatin (DDP): Supplied by Shandong Qilu Pharmaceutics Company.
Animal: Male Kunming mice weighing 16 to 22 g were purchased from Institute of Laboratory Animal Sciences, Chinese Academy of Medical Sciences (Type II, Certificate No: SCXK-Jing 2000-0006). All the mice were feeded in standard breeding boxes, 5 per box, kept these boxes dry and clean, ventilate and sterilize animal room at fixed time, lightening time: 8:00-20:00, room temperature: 20-26° C., humidity: 40-70%, forage: clean breeding forage, bought from Animal Center of Academy of Military Medical Sciences, Certificate No: SCXX-(army) 2002-001.
Serum biochemistry kit: Beijing Beihua Refined Chemical Limited-liability Company
Apparatus: WELLSCAN MK3 Scanner, Germent SIGMA3K 15 Centrifuge, TGL-16G Freezing Centrifuge, Shanghai Anting Scientific Instrument Factory, Votex, American Bohemia N.Y Company.
Methods:
Animal grouping: According to body weights, male Kunming mice weighing 18 to 22 grams were randomly divided into 9 groups: control group, Cisplatin group (model group), Losartan potassium group, groups of three crystal forms of XLF-III-43, n=8 for each group.
Modeling and administrating: XLF-III-43 were dissolved in 0.5% sodium carboxymethylcellulose, Losartan potassium and Cisplatin were dissolved in physiological saline. Since two days before giving Cisplatin by peritoneal injection, Losartan potassium group and groups of three crystal forms of XLF-III-43 were intraperitoneally administered respectively. Control animals received an equal volume of physiological saline.

Serum parameters detecting: Blood samples were collected from the orbital venous plexus at day 3, 5, and 7 after injecting Cisplatin. Serum BUN and Scr were detected by serum biochemistry kit.

Results: In model group, serum Scr and BUN levels increased significantly, showed that animal model was made successfully. And in treated groups, group of amorphous form of XLF-III-43 showed the best renal function protective effect, with good dose-effect relationship.

characterized by peaks in powder X-ray diffraction analysis (CuK$_\alpha$ irradiation) which are identified by the following 2-Theta values (°), d values (Å), and relative intensity of diffraction peaks (Height %):

| Peak | 2-Theta | d(Å) | Height % |
|---|---|---|---|
| 1 | 5.661 | 15.60 | 9 |
| 2 | 11.440 | 7.73 | 99 |
| 3 | 13.420 | 6.59 | 10 |

TABLE 19-A

| Groups | Dose (mg/kg) | Scr (mg/dL) | reduction (%) | BUN (mg/dL) | reduction (%) |
|---|---|---|---|---|---|
| Protective effects of different crystalline forms of XLF-III-43 on acute renal function injury in mice induced by Cisplatin. (3 days after injecting Cisplatin) | | | | | |
| Control | — | 1.14 ± 0.67 | — | 24.89 ± 3.97 | — |
| Model | 7 | 1.81 ± 1.30 | −59.1 | 30.02 ± 16.11 | −20.8 |
| Losartan | 25.0 × 3 | 1.41 ± 1.00 | 22.4 | 30.58 ± 4.19 | −1.9 |
| Crystalline form I | 12.5 × 7 | 1.28 ± 1.03 | 29.3 | 26.52 ± 4.03 | 11.7 |
|  | 25.0 × 7 | 1.18 ± 0.65 | 35.0 | 38.21 ± 8.43 | −27.3 |
| Crystalline form II | 12.5 × 7 | 1.82 ± 0.96 | 0.0 | 28.85 ± 9.46 | 3.9 |
|  | 25.0 × 7 | 1.72 ± 0.92 | 4.9 | 45.77 ± 16.59 | −52.5 |
| Crystalline form V | 12.5 × 7 | 1.04 ± 0.91 | 42.8 | 28.62 ± 6.05 | 4.7 |
|  | 25.0 × 7 | 0.84 ± 0.68 | 53.7 | 26.09 ± 2.82 | 13.1 |
| Protective effects of different crystalline forms of XLF-III-43 on acute renal function injury in mice induced by Cisplatin. (5 days after injecting Cisplatin) | | | | | |
| Control | — | 0.70 ± 0.32 | — | 19.92 ± 2.94 | — |
| Model | 7 | 1.90 ± 0.62 | −171.8 | 42.11 ± 11.14 | −111.4 |
| Losartan | 25.0 × 3 | 1.16 ± 0.48 | 39.3 | 31.75 ± 9.32 | 24.6 |
| Crystalline form I | 12.5 × 7 | 0.65 ± 0.34 | 65.8 | 22.49 ± 3.05 | 46.6 |
|  | 25.0 × 7 | 0.96 ± 0.28 | 49.5 | 26.47 ± 6.11 | 37.1 |
| Crystalline form II | 12.5 × 7 | 2.08 ± 0.79 | −9.3 | 25.10 ± 12.01 | 40.4 |
|  | 25.0 × 7 | 2.16 ± 1.72 | −13.5 | 80.73 ± 69.25 | −91.7 |
| Crystalline form V | 12.5 × 7 | 1.60 ± 0.56 | 15.9 | 22.62 ± 4.41 | 46.3 |
|  | 25.0 × 7 | 1.35 ± 0.32 | 28.8 | 23.13 ± 4.15 | 45.1 |
| Protective effects of different crystalline forms of XLF-III-43 on acute renal function injury in mice induced by Cisplatin. (7 days after injecting Cisplatin) | | | | | |
| Control | — | 2.05 ± 0.46 | — | 28.16 ± 4.00 | — |
| Model | 7 | 2.67 ± 1.05 | −30.3 | 39.80 ± 6.02 | −41.3 |
| Losartan | 25.0 × 3 | 1.74 ± 0.31 | 34.7 | 30.32 ± 2.89 | 23.8 |
| Cristal-I | 12.5 × 7 | 2.29 ± 0.47 | 14.3 | 41.21 ± 9.95 | −3.5 |
|  | 25.0 × 7 | 2.08 ± 0.75 | 22.0 | 43.37 ± 18.02 | −9.0 |
| Cristal-II | 12.5 × 7 | 2.52 ± 0.68 | 5.8 | 43.25 ± 11.66 | −8.7 |
|  | 25.0 × 7 | 2.14 ± 1.39 | 20.0 | 33.90 ± 3.69 | 14.8 |
| Cristal-V | 12.5 × 7 | 1.80 ± 0.50 | 32.5 | 36.83 ± 8.05 | 7.5 |
|  | 25.0 × 7 | 1.74 ± 0.34 | 34.7 | 33.84 ± 8.57 | 15.0 |

What is claimed is:

1. Solid form V of XLF-III-43 of Formula (I),

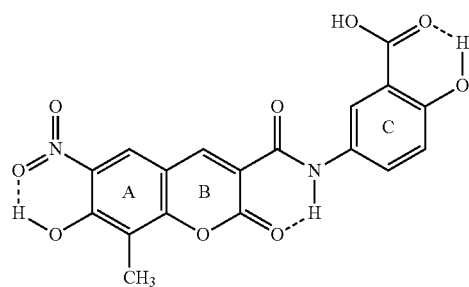

| Peak | 2-Theta | d(Å) | Height % |
|---|---|---|---|
| 4 | 14.737 | 6.01 | 1 |
| 5 | 15.800 | 5.60 | 4 |
| 6 | 17.220 | 5.14 | 11 |
| 7 | 17.778 | 4.98 | 3 |
| 8 | 20.800 | 4.27 | 9 |
| 9 | 22.960 | 3.87 | 1 |
| 10 | 23.880 | 3.72 | 1 |
| 11 | 26.780 | 3.33 | 100 |
| 12 | 28.923 | 3.08 | 2 |
| 13 | 31.561 | 2.83 | 2 |
| 14 | 36.020 | 2.49 | 2 |
| 15 | 37.159 | 2.42 | 1 |
| 16 | 41.060 | 2.10 | 1 |
| 17 | 43.860 | 2.06 | 2 |
| 18 | 45.440 | 1.99 | 1 |
| 19 | 53.958 | 1.70 | 2 |

2. The solid form V of XLF-III-43 of claim 1, characterized in that in the DSC spectrum there are a heat absorption peak with the transition value at about 169° C., and a peak of heat emission with the transition value at about 345° C.

3. The solid form V of XLF-III-43 of claim 1, characterized in that in the infrared absorption spectrum there are absorption peaks at 3565.3, 3488.9, 3238.7, 3104.2, 1719.8, 1669.1, 1621.6, 1560.6, 1537.0, 1488.0, 1471.6, 1445.9, 1379.1, 1359.7, 1313.6, 1285.7, 1258.6, 1152.8, 1237.1, 1194.2, 1118.6, 1071.3, 1021.5, 968.3, 917.5, 893.2, 848.5, 835.4, 789.2, 763.4, 746.7, 727.2, 674.4, 623.1, 579.1, 559.4, 528.8, 506.1, 427.9 $cm^{-1}$, and the main characteristic absorption peaks are the peaks at 3565.3, 3488.9, 3238.7, 1719.8, 1669.1, 1560.6, 1379.1, 1258.6, 1237.1, 1194.2, 835.4, 427.9 $cm^{-1}$.

4. A pharmaceutical composition comprising a therapeutic dose of solid form V of XLF-III-43 according to any of claims 1 to 3 and pharmacodynamic acceptable vehicle.

5. The pharmaceutical composition according to claim 4, in a form selected from the group consisting of tablet, capsule, pill, an injection formulation, a sustained release system, and a controlled release system.

6. A method for treating kidney dysfunction, wherein the kidney dysfunction is diabetic nephropathy or hypertension nephropathy, comprising administering a therapeutic dosage of solid form V of XLF-III-43 according to any of claims 1 to 3.

7. A method of preparing solid form V of XLF-III-43:
   (a) bringing a sample of XLF-III-43 into single or mixed solvent and heating to dissolve completely, then in the environment of at a temperature in the range of 75° C. to 85° C., relative humidity of below 90%, recrystallizing completely and obtaining a solid substance sample of XLF-III-43;
   (b) separating the solid substance sample of XLF-III-43 of step (a) from the solution;
   (c) transferring the separated solid substance sample of XLF-III-43 obtained in step (b) in dilute hydrochloric acid for above 1 day, and obtaining solid form V; and
   (d) drying the obtained solid form V until the surface solvent is removed.

* * * * *